US012173062B2

(12) United States Patent
Kreft et al.

(10) Patent No.: US 12,173,062 B2
(45) Date of Patent: Dec. 24, 2024

(54) MODIFIED TNF-α ANTIBODIES AND USES THEREOF

(71) Applicant: Bright Peak Therapeutics AG, Basel (CH)

(72) Inventors: Bertolt Kreft, Kleinmachnow (DE); Vijaya Raghavan Pattabiraman, Volketswil (CH); Rubén Alvarez Sanchez, Rosenau (FR); Magali Muller, Pulversheim (FR); Jean-Philippe Carralot, Saint-Louis (FR)

(73) Assignee: Bright Peak Therapeutics AG, Basel (CH)

( * ) Notice: Subject to any disclaimer, the term of this patent is extended or adjusted under 35 U.S.C. 154(b) by 268 days.

(21) Appl. No.: 17/861,178

(22) Filed: Jul. 9, 2022

(65) Prior Publication Data

US 2023/0183331 A1    Jun. 15, 2023

Related U.S. Application Data

(60) Provisional application No. 63/219,989, filed on Jul. 9, 2021, provisional application No. 63/219,995, filed on Jul. 9, 2021.

(51) Int. Cl.
*C07K 16/24* (2006.01)
*C07K 14/55* (2006.01)

(52) U.S. Cl.
CPC ............ *C07K 16/241* (2013.01); *C07K 14/55* (2013.01); *C07K 2317/52* (2013.01); *C07K 2319/33* (2013.01)

(58) Field of Classification Search
CPC .............................. C07K 16/241; C07K 14/55
See application file for complete search history.

(56) References Cited

U.S. PATENT DOCUMENTS

| | | | |
|---|---|---|---|
| 5,206,344 A | 4/1993 | Nandini et al. |
| 7,507,406 B2 | 3/2009 | Gilles et al. |
| 7,517,526 B2 | 4/2009 | Gilles et al. |
| 7,951,360 B2 | 5/2011 | Wittrup et al. |
| 8,815,247 B2 | 8/2014 | Govindappa et al. |
| 9,427,478 B2 | 8/2016 | Bregeon et al. |
| 9,616,105 B2 | 4/2017 | Paulson et al. |
| 9,717,803 B2 | 8/2017 | Bregeon et al. |
| 9,732,134 B2 | 8/2017 | Gavin et al. |
| 9,764,038 B2 | 9/2017 | Dennler et al. |
| 10,010,587 B2 | 7/2018 | Krishna et al. |
| 10,434,180 B2 | 10/2019 | Bregeon et al. |
| 10,610,571 B2 | 4/2020 | Ptacin et al. |
| 10,675,359 B2 | 6/2020 | Dennler et al. |
| 11,384,131 B2 | 7/2022 | Garcia et al. |
| 2010/0036097 A1 | 2/2010 | Dane et al. |
| 2016/0375149 A1 | 12/2016 | Irvine et al. |
| 2017/0216403 A1 | 8/2017 | Wittrup et al. |
| 2017/0313753 A1 | 11/2017 | Gavin et al. |
| 2019/0023760 A1 | 1/2019 | Bode et al. |
| 2019/0194641 A1 | 6/2019 | Spycher et al. |
| 2020/0190165 A1 | 6/2020 | Yamada et al. |
| 2020/0231644 A1 | 7/2020 | Ptacin et al. |
| 2020/0299349 A1 | 9/2020 | Garcia et al. |
| 2020/0317787 A1 | 10/2020 | Zhongdao et al. |
| 2021/0024601 A1 | 1/2021 | Carlson et al. |
| 2021/0101953 A1 | 4/2021 | Sun et al. |
| 2021/0128743 A1 | 5/2021 | Spycher et al. |
| 2021/0187027 A1 | 6/2021 | Wu et al. |
| 2021/0196796 A1 | 7/2021 | Penaflor-Aspuria et al. |
| 2021/0252157 A1 | 8/2021 | Pattabiraman et al. |
| 2021/0260163 A1 | 8/2021 | Yu et al. |
| 2021/0269497 A1 | 9/2021 | Li et al. |
| 2021/0275641 A1 | 9/2021 | Emmerich et al. |
| 2021/0292386 A1 | 9/2021 | Ugur et al. |
| 2021/0340207 A1 | 11/2021 | Abrahams et al. |
| 2021/0340208 A1 | 11/2021 | Ye et al. |
| 2022/0056094 A1 | 2/2022 | Chen et al. |
| 2022/0133904 A1 | 5/2022 | Schibli et al. |

FOREIGN PATENT DOCUMENTS

| | | |
|---|---|---|
| EP | 2970486 B1 | 5/2018 |
| EP | 3606946 A1 | 6/2019 |
| EP | 3630163 A1 | 4/2020 |
| EP | 2382228 B1 | 8/2020 |
| EP | 3808760 A1 | 4/2021 |
| EP | 3811978 A1 | 4/2021 |
| EP | 3720871 A1 | 9/2021 |
| WO | WO-2002085923 A2 | 10/2002 |
| WO | WO-2005003294 A2 | 1/2005 |
| WO | WO-2005016969 A2 | 2/2005 |

(Continued)

OTHER PUBLICATIONS

Cassell, Delanie J., et al., "Therapeutic Enhancment of IL-2 Through Molecular Design," *Current Pharmaceutical Design*, vol. 8, 2002, pp. 2171-2183.
Levin, Aron M., et al., "Exploiting a natural conformational switch to engineer an interleukin-2 'superkine'," *Nature*, vol. 484, Apr. 26, 2012, pp. 529-535.
Matsuda, Yutaka, et al., "Chemical Site-Specific Conjugation Platform to Improve the Pharmacokinetics and Therapeutic Index of Antibody-Drug Conjugates," *Molecular Pharmaceutics*, vol. 18, 2021, pp. 4058-4066.
Mitra, Suman, et al., "Interleukin-2 Activity Can Be Fine Tuned with Engineered Receptor Signaling Clamps," *Immunity*, vol. 42, May 19, 2015, pp. 826-838.
Rao, Balaji M., et al., "High-Affinity CD25-Binding IL-2 Mutants Potently Stimulate Persistent T Cell Growth," *Biochemistry*, vol. 44.31, 2005, pp. 10696-10701.

(Continued)

*Primary Examiner* — Prema M Mertz
(74) *Attorney, Agent, or Firm* — WILSON SONSINI GOODRICH & ROSATI

(57) ABSTRACT

The present disclosure relates to modified anti-TNFα polypeptides, compositions comprising modified anti-TNFα polypeptides, methods of making the same, and methods of using the modified anti-TNFα polypeptides for treatment of diseases. In one aspect, the disclosure relates to the treatment of inflammatory disorders using the modified anti-TNFα polypeptides.

18 Claims, 19 Drawing Sheets

Specification includes a Sequence Listing.

(56) References Cited

FOREIGN PATENT DOCUMENTS

| | | | |
|---|---|---|---|
| WO | WO-2005019415 A2 | 3/2005 |
| WO | WO-2006069246 A2 | 6/2006 |
| WO | WO-2007079130 A2 | 7/2007 |
| WO | WO-2013074598 A1 | 5/2013 |
| WO | WO-2014036492 A1 | 3/2014 |
| WO | WO-2015054658 A1 | 4/2015 |
| WO | WO-2016115168 A1 | 7/2016 |
| WO | WO-2017210471 A1 | 12/2017 |
| WO | WO-2018189220 A1 | 10/2018 |
| WO | WO-2018199337 A1 | 11/2018 |
| WO | WO-2018215938 A1 | 11/2018 |
| WO | WO-2019125732 A1 | 6/2019 |
| WO | WO-2019129053 A1 | 7/2019 |
| WO | WO-2019144945 A1 | 8/2019 |
| WO | WO-2019173773 A1 | 9/2019 |
| WO | WO-2019173832 A2 | 10/2019 |
| WO | WO-2019185792 A1 | 10/2019 |
| WO | WO-2019240287 A1 | 12/2019 |
| WO | WO-2019240288 A1 | 12/2019 |
| WO | WO-2019246404 A1 | 12/2019 |
| WO | WO-2020061142 A1 | 3/2020 |
| WO | WO-2020088459 A1 | 5/2020 |
| WO | WO-2020090979 A1 | 5/2020 |
| WO | WO-2020188061 A1 | 9/2020 |
| WO | WO-2020233515 A1 | 11/2020 |
| WO | WO-2020252421 A2 | 12/2020 |
| WO | WO-2021030374 A1 | 2/2021 |
| WO | WO-2021030483 A1 | 2/2021 |
| WO | WO-2021093633 A1 | 5/2021 |
| WO | WO-2021119516 A1 | 6/2021 |
| WO | WO-2021122866 A1 | 6/2021 |
| WO | WO-2021133839 A1 | 7/2021 |
| WO | WO-2021140416 A2 | 7/2021 |
| WO | WO-2021201615 A1 | 10/2021 |
| WO | WO-2021209402 A2 | 10/2021 |
| WO | WO-2022129512 A1 | 6/2022 |
| WO | WO-2022140797 A1 | 6/2022 |
| WO | WO-2022159771 A1 | 7/2022 |

OTHER PUBLICATIONS

Rao, Balaji M., et al., "Interleukin-2 mutants with enhanced α-receptor subunit binding affinity." *Protein Engineering* 16.12, 2003, pp. 1081-1087.

Klein, Christian, et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines." Oncoimmunology 6.3 (2017): e1277306.

Gillies, Stephen D., et al., "An anti-CD20-IL-2 immunocytokine is highly efficacious in a SCID mouse model of established human B lymphoma." Blood 105.10 (2005): 3972-3978.

Wang, Xingxing, et al., "T Cell-Signaling-Responsive Conjugate of Antibody with siRNA to Overcome Acquired Resistance to anti-PD-1 Immunotherapy." Advanced Therapeutics 5.1 (2022).

Dougan, Michael, and Stephanie K. Dougan. "Targeting immunotherapy to the tumor microenvironment." Journal of cellular biochemistry, 118.10, Nov. 2016: 3049-3054.

Chen, Xi, et al. "Therapeutic efficacy of an anti-PD-L1 antibody based immunocytokine in a metastatic mouse model of colorectal cancer." Biochemical and biophysical research communications, vol. 480, No. 2, Oct. 5, 2016: 160-165.

Marusic, Carla, et al. "N-glycan engineering of a plant-produced anti-CD20-hIL-2 immunocytokine significantly enhances its effector functions." Biotechnology and bioengineering 115.3, Nov. 20, 2017: 565-576.

Singh, Harjeet, et al. "Combining adoptive cellular and immunocytokine therapies to improve treatment of B-lineage malignancy." Cancer Research, 67.6, Mar. 15, 2007: 2872-2880.

Morello, Aurore, et al., "A novel bifunctional anti-PD-1 IL-7 fusion protein to reinvigorate exhausted T cell and disarms Treg suppressive activity." Cancer Research 80.16_Supplement (2020): 910-910.

PCT International Search Report for PCT/IB2022/056365, mailed Nov. 11, 2022, 6 pages. (English).

Pattabiraman, Vijaya R., et al., "Creating next-generation biologics using a novel chemistry platform technology." *Cancer Research* 82.12_Supplement (2022): 2138-2138.

Figure 9A                                  Figure 9B

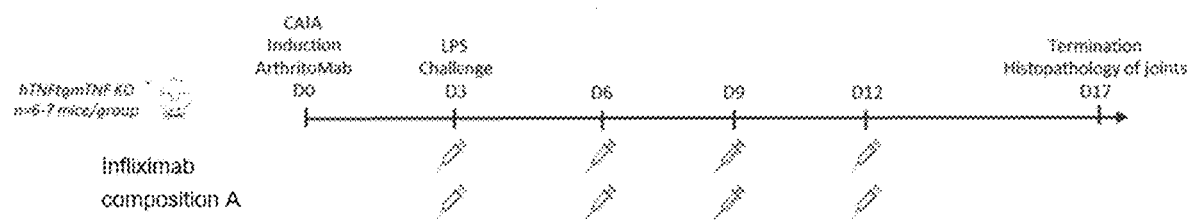
Figure 11A
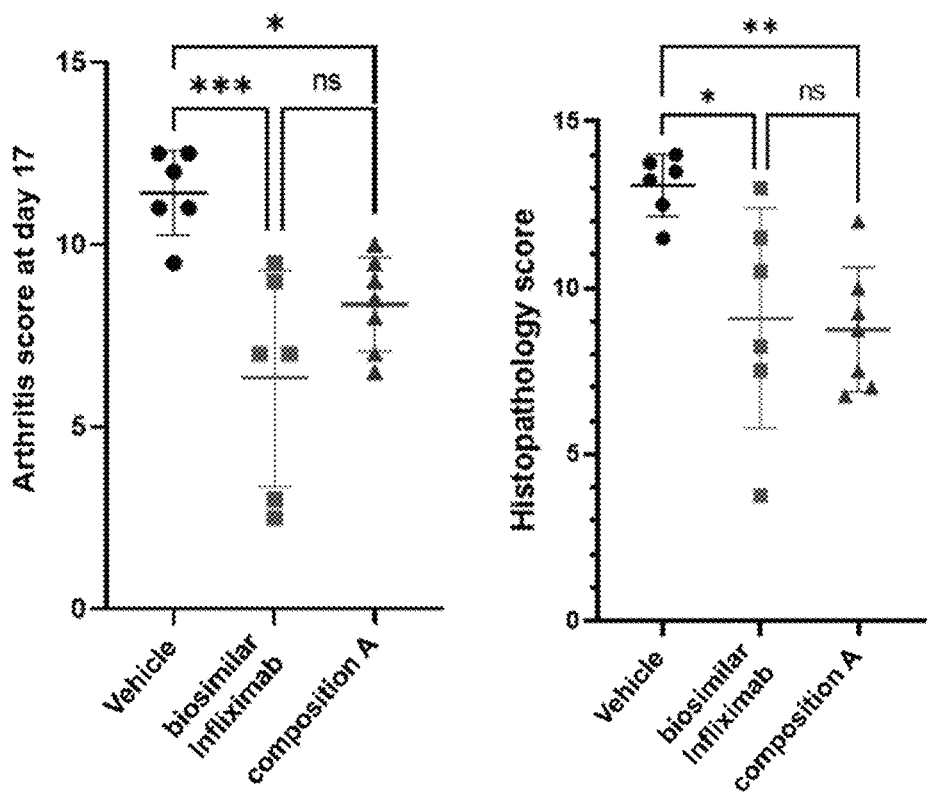
Figure 11B
Figure 11C

MODIFIED TNF-α ANTIBODIES AND USES THEREOF

CROSS REFERENCE

This application claims the benefit of U.S. Provisional Application No. 63/219,995 filed Jul. 9, 2021, and of U.S. Provisional Application No. 63/219,989 filed Jul. 9, 2021, which applications are incorporated herein by reference in their entirety.

SEQUENCE LISTING

The instant application contains a Sequence Listing which has been submitted electronically in XML file format and is hereby incorporated by reference in its entirety. Said XML copy, created on Aug. 17, 2022, is named 94917-0034_718201US_SL.xml and is 114,362 bytes in size.

BACKGROUND

Immunotherapies utilize the immune system of a subject to aid in the treatment of ailments. Immunotherapies can be designed to either activate or suppress the immune system depending on the nature of the disease being treated. A goal of various immunotherapies is to stimulate the immune system so that it recognizes and treats inflammatory diseases.

Tumor necrosis factor alpha (TNFα) is a cytokine released by certain macrophages as part of the inflammatory response. TNF's primary role is in the regulation of immune cells. While TNFα is generally associated with activation of the immune system in response to an infection, in some instances TNFα has been observed to have immunosuppressive characteristics as well, possible through its positive effects on regulatory T cells. For his reason, anti-TNF antibodies (and other therapies) have been investigated as an immunotherapy in the treatment of inflammatory diseases. However, in many cases, this single mechanism therapy alone is insufficient for treating a desired disease. Thus, improved anti-TNFα therapies are needed.

BRIEF SUMMARY

Described herein are anti-TNFα-interleukin 2 (IL-2) immunoconjugates and uses thereof.

In one aspect, described herein is a composition comprising: a polypeptide which selectively binds to tumor necrosis factor α (TNFα); a modified IL-2 polypeptide; and a linker, wherein the linker comprises: a first point of attachment covalently attached to the modified IL-2 polypeptide; and a second point of attachment covalently attached to the polypeptide which selectively binds to TNFα.

In another aspect, described herein is a composition comprising: an IL-2 polypeptide, wherein the IL-2 polypeptide comprises: a first polymer attached at amino acid residue 1, wherein amino acid residue position numbering of the modified IL-2 polypeptide is based on SEQ ID NO: 1 as a reference sequence; and a polypeptide which selectively binds to tumor necrosis factor α (TNFα).

In another aspect, described herein is a composition comprising: (a) an antibody or an antigen binding fragment which selectively binds to tumor necrosis factor α (TNFα) and that comprises an Fc region, the Fc region comprising an amino acid sequence with 90% or more identity to SEQ ID NO: 136; (b) one or more linkers covalently attached to the Fc region at an amino acid residue selected from the group consisting of: (i) positions 30 to 32 of SEQ ID NO: 136; (ii) positions 72 to 74 of SEQ ID NO: 136; and (iii) position 101 of SEQ ID NO: 136; and (c) one or more cytokines covalently attached to the linker.

Any of the antibodies or the antigen binding fragments described herein which selectively bind to tumor necrosis factor α (TNFα) can be a recombinant protein or a synthetic protein.

The polypeptide which selectively binds to TNFα can be, for example, a recombinant protein or a synthetic protein.

In another aspect, described herein is a pharmaceutical composition that comprises: a) a composition described herein; and b) one or more pharmaceutically acceptable carriers or excipients.

In another aspect, described herein is a method of treating an inflammatory disorder in a subject in need thereof, comprising administering to the subject an effective amount of a composition described herein or a pharmaceutical composition described herein.

In another aspect, described herein is a method of making a composition described herein, comprising: a) covalently attaching a reactive group to a specific residue of a polypeptide which selectively binds TNFα; b) contacting the reactive group with a complementary reactive group attached to a cytokine; and c) forming the composition.

In another aspect, described herein is a method of creating a composition comprising: a polypeptide which selectively binds to tumor necrosis factor α (TNFα); a modified IL-2 polypeptide; and a linker, wherein the linker comprises: a first point of attachment covalently attached to a non-terminal residue of the modified IL-2 polypeptide; and a second point of attachment covalently attached to the polypeptide which selectively binds to TNFα, the method comprising: a) providing polypeptide which selectively binds to TNFα having at least one acceptor amino acid residue that is reactive with a linker in the presence of a coupling enzyme; and b) reacting said polypeptide which selectively binds to TNFα with a linker comprising a primary amine, wherein the linker comprises a reactive group (R), in the presence of an enzyme capable of causing the formation of a covalent bond between the at least one acceptor amino acid residue and the linker, wherein the covalent bond is not at the R moiety, and wherein the method is performed under conditions sufficient to cause the at least one acceptor amino acid residue to form a covalent bond to the reactive group via the linker, wherein the covalent bond comprises the second point of attachment of the linker.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

FIG. 9A shows a time-profile of $T_{reg}$ count (as fold change vs baseline) in mice after subcutaneous administration of Composition A or Composition B at 1 mg/kg.

FIG. 9B shows a time-profile of CD8+ T effector cells ($T_{eff}$) count (as fold change vs baseline) in mice after subcutaneous administration of Composition A or Composition B at 1 mg/kg.

FIG. 11A shows a schematic of an experimental design testing the therapeutic effect of Composition A in a mouse model of collagen antibody-induced arthritic inflammation (CAIA).

FIG. 11B shows the arthritic score for individual animals at day 17 of the study described in FIG. 11A.

FIG. 11C shows joint histopathology scores for individual animals at day 17 of the study described in FIG. 11A.

DETAILED DESCRIPTION

Figure 1:
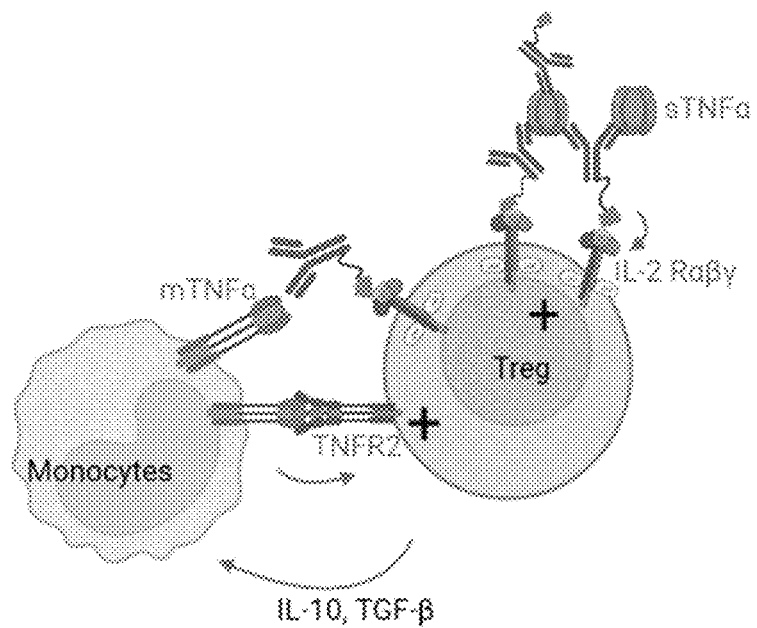
FIG. 1 illustrates an anti-TNFα-IL-2 immunocytokine of the disclosure and the interaction of the anti-TNFα-IL-2 immunocytokine with a regulatory T cell ($T_{reg}$) through IL-2Rα agonism and neutralization of soluble TNFα and binding to membrane bound TNFα.

Disclosed herein are anti-TNFα polypeptides or antigen binding fragments thereof. In some embodiments, the anti-TNFα polypeptides or antigen binding fragments thereof are conjugated to a cell-signaling molecule, such as a cytokine. In some embodiments, the cytokine is IL-2. FIG. 1 illustrates an anti-TNFα-IL-2 immunocytokine of the disclosure and the interaction of the anti-TNFα-IL-2 immunocytokine with a Treg cell through IL-2Rαβγ binding, neutralization of soluble and binding to membrane bound TNFα. The anti-TNFα-IL-2 immunocytokines of the disclosure can have synergistic efficacy by a subject. In some embodiments, the anti-TNFα-IL-2 immunocytokines may significantly improve delivery to inflamed tissue, thereby improving the therapeutic window.

The anti-TNFα-IL-2 immunocytokines can act by one or more modes of action. In some embodiments, the anti-TNFα-IL-2 immunocytokines can neutralize soluble TNFα, bind to membrane-bound TNFα and inhibiting the production of several immune system molecules such as, for example, interleukin-1 and interleukin-6.

In some preferred embodiments of the disclosure, the IL-2 portion of the immunocytokines provided herein is an IL-2 polypeptide which is biased towards signaling through the alpha receptor subunit of the IL-2 receptor compared to wild type IL-2. In some embodiments, use of an IL-2Rα biased IL-2 polypeptide allows for enhanced proliferation of Treg cells in vivo compared to a wild type IL-2. In some embodiments, the IL-2Rα biased IL-2 polypeptide is biased towards the alpha receptor subunit either through enhanced binding to the alpha subunit or a disruption of binding to the beta subunit, or both. In some embodiments, biasing the IL-2 polypeptide towards the alpha receptor subunit is accomplished via amino acid substitution. In some embodiments, biasing the IL-2 polypeptide towards the subunit is accomplished via addition of other groups to the IL-2 polypeptide (e.g., polymers, or by points of attachment to additional polypeptides such as polypeptides which bind to TNFα as provided herein) which disrupt binding to the beta receptor subunit. In preferred embodiments, the IL-2 polypeptide is biased towards the alpha receptor subunit due to amino acid substitutions of the IL-2 polypeptide itself.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment. The section headings used herein are for organizational purposes only and are not to be construed as limiting the subject matter described.

Definitions

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Referred to herein are groups which are "attached" or "covalently attached" to residues of IL-2 polypeptides. As used herein, "attached" or "covalently attached" means that the group is tethered to the indicated reside, and such tethering can include a linking group (i.e., a linker). Thus, for a group "attached" or "covalently attached" to a residue, it is expressly contemplated that such linking groups are also encompassed.

Binding affinity refers to the strength of a binding interaction between a single molecule and its ligand/binding partner. A higher binding affinity refers to a higher strength bond than a lower binding affinity. In some instances, binding affinity is measured by the dissociation constant (KD) between the two relevant molecules. When comparing KD values, a binding interaction with a lower value will have a higher binding affinity than a binding interaction with a higher value. For a protein-ligand interaction. KD is calculated according to the following formula:

$$K_D = \frac{[L][P]}{[LP]}$$

where [L] is the concentration of the ligand, [P] is the concentration of the protein, and [LP] is the concentration of the ligand/protein complex.

Referred to herein are certain amino acid sequences (e.g., polypeptide sequences) which have a certain percent sequence identity to a reference sequence or refer to a residue at a position corresponding to a position of a reference sequence. Sequence identity is measured by protein-protein BLAST algorithm using parameters of Matrix BLOSUM62, Gap Costs Existence: 11, Extension: 1, and Compositional Adjustments Conditional Compositional Score Matrix Adjustment. This alignment algorithm is also used to assess if a residue is at a "corresponding" position through an analysis of the alignment of the two sequences being compared.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" suitable for the disclosure may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts include those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Certain formulas and other illustrations provided herein depict triazole reaction products resulting from azide-alkyne cycloaddition reactions. While such formulas generally depict only a single regioisomer of the resulting triazole formed in the reaction, it is intended that the formulas encompass both resulting regioisomers. Thus, while the formulas depict only a single regioisomer

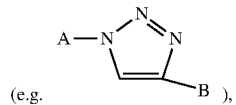

(e.g.                        B ), it is intended that the other regioisomer

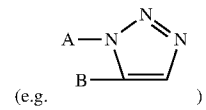

(e.g.                        )

is also encompassed.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The term "optional" or "optionally" denotes that a subsequently described event or circumstance can but need not occur, and that the description includes instances where the event or circumstance occurs and instances in which it does not.

The term "moiety" refers to a specific segment or functional group of a molecule. Chemical moieties are often recognized chemical entities embedded in or appended to a molecule.

As used herein "an N-terminus with glutaric acid and 0.5 kDa azido PEG" refers to a modification to an N-terminal amine of an IL-2 polypeptide provided herein with a structure of

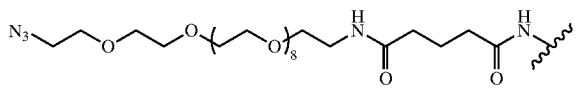

While described as having an azide functionality, it is contemplated that the azide can be replaced with an alternative conjugation handle in each case wherein a modified IL-2 polypeptide comprises the N-terminus with glutaric acid and 0.5 kDa azido PEG.

Composition AA refers to an IL-2 polypeptide having a sequence set forth in SEQ ID NO: 3 with a N-terminus with glutaric acid and 0.5 kDa azido PEG, which can be used for conjugation to a desired antibody such as an anti-TNFα antibody.

Composition A refers to an anti-TNFα antibody/IL-2 conjugate prepared from a reaction of Composition AA and anti-TNFα antibody Infliximab biosimilar. Composition A is formed from a reaction of the azide functionality of Composition AA with a DBCO functionality attached to residue K248 of the Fc region of Infliximab biosimilar (EU numbering). The DBCO functionality is added to Infliximab biosimilar using an affinity peptide system according to AJICAP™ technology from Ajinomoto. Composition A has a drug-antibody ratio of 1.

Composition B refers to an anti-TNFα antibody/IL-2 conjugate prepared from a reaction of Composition AA and anti-TNFα antibody Infliximab biosimilar. Composition B is formed from a reaction of the azide functionality of Composition AA with a DBCO functionality attached to residue K248 of the Fc region of Infliximab biosimilar (EU numbering). The DBCO functionality is added to Infliximab biosimilar using an affinity peptide system according to AJICAP™ technology from Ajinomoto. Composition B has a drug-antibody ratio of 2.

Composition C refers to an anti-TNFα antibody/IL-2 conjugate prepared from a reaction of Composition AA and anti-TNFα antibody (biosimilar Adalimumab). Composition C is formed from a reaction of the azide functionality of Composition AA with a DBCO functionality attached to residue K248 of the Fc region of an anti-TNFα antibody (EU numbering). The DBCO functionality is added to an anti-TNFα antibody using an affinity peptide system according to AJICAP™ technology from Ajinomoto. Composition C has a drug-antibody ratio of 1.

Composition D refers to an anti-TNFα antibody/IL-2 conjugate prepared from a reaction of Composition AA and anti-TNFα antibody (a generic (i.e. biosimilar) version of Adalimumab (Humira™)). Composition D is formed from a reaction of the azide functionality of Composition AA with a DBCO functionality attached to residue K248 of the Fc region of anti-TNFα antibody. The DBCO functionality is added to anti-TNFα antibody using an affinity peptide system according to AJICAP™ technology from Ajinomoto. Composition D has a drug-antibody ratio of 2.

As used herein, "AJICAP™ technology," "AJICAP™ methods," and similar terms refer to systems and methods (currently produced by Ajinomoto Bio-Pharma Services ("Ajinomoto")) for the site specific functionalization of antibodies and related molecules using affinity peptides to deliver the desired functionalization to the desired site. General protocols for the AJICAP™ methodology are found at least in PCT Publication No. WO2018199337A1, PCT Publication No. WO2019240288A1, PCT Publication No. WO2019240287A1, PCT Publication No. WO2020090979A1, Matsuda et al., *Mol. Pharmaceutics* 2021, 18, 4058-4066, and Yamada et al., AJICAP: Affinity Peptide Mediated Regiodivergent Functionalization of Native Antibodies. *Angew. Chem., Int. Ed.* 2019, 58, 5592-5597, and in particular Examples 2-4 of US Patent Publication No. US20200190165A1. In some embodiments, such methodologies site specifically incorporate the desired functionalization at lysine residues at a position selected from position 246, position 248, position 288, position 290, and position 317 of an antibody Fc region (e.g., an IgG1 Fc region) (EU numbering). In some embodiments, the desired functionalization is incorporated at residue position 248 of an antibody Fc region (EU numbering). In some embodiments, position 248 corresponds to the 18th residue in a human IgG CH2 region (EU numbering).

As used herein, the term "number average molecular weight" (Mn) means the statistical average molecular weight of all the individual units in a sample, and is defined by Formula (1):

$$Mn = \frac{\sum N_i M_i}{\sum N_i} \quad \text{Formula (1)}$$

where $M_i$ is the molecular weight of a unit and Ni is the number of units of that molecular weight.

As used herein, the term "weight average molecular weight" (Mw) means the number defined by Formula (2):

$$Mw = \frac{\sum N_i M_i^2}{\sum N_i M_i} \quad \text{Formula (2)}$$

where $M_i$ is the molecular weight of a unit and Ni is the number of units of that molecular weight.

As used herein, "peak molecular weight" (Mp) means the molecular weight of the highest peak in a given analytical method (e.g., mass spectrometry, size exclusion chromatography, dynamic light scattering, analytical centrifugation, etc.).

As used herein, "non-canonical" amino acids can refer to amino acid residues in D- or L-form that are not among the 20 canonical amino acids generally incorporated into naturally occurring proteins.

As used herein, "conjugation handle" refers to a reactive group capable of forming a bond upon contacting a complementary reactive group. In some instances, a conjugation handle preferably does not have a substantial reactivity with other molecules which do not comprise the intended complementary reactive group. Non-limiting examples of conjugation handles, their respective complementary conjugation handles, and corresponding reaction products can be found in the table below. While table headings place certain reactive groups under the title "conjugation handle" or "complementary conjugation handle," it is intended that any reference to a conjugation handle can instead encompass the complementary conjugation handles listed in the table (e.g., a trans-cyclooctene can be a conjugation handle, in which case tetrazine would be the complementary conjugation handle). In some instances, amine conjugation handles and conjugation handles complementary to amines are less preferable for use in biological systems owing to the ubiquitous presence of amines in biological systems and the increased likelihood for off-target conjugation.

TABLE of Conjugation Handles

| Conjugation Handle | Complementary Conjugation Handle | Reaction Product |
|---|---|---|
| Sulfhydryl | alpha-halo-carbonyl (e.g., bromoacetamide), alpha-beta unsaturated carbonyl (e.g., maleimide, acrylamide) | thioether |

TABLE of Conjugation Handles

| Conjugation Handle | Complementary Conjugation Handle | Reaction Product |
|---|---|---|
| Azide | alkyne (e.g., terminal alkyne, substituted cyclooctyne (e.g., dibenzocycloocytne (DBCO), difluorocyclooctyne, bicyclo[6.1.0]nonyne, etc.)) | triazole |
| Phosphine | Azide/ester pair | amide |
| Tetrazine | trans-cyclooctene | dihydropyridazine |
| Amine | Activated ester (e.g., N-hydroxysuccinimide ester, pentaflurophenyl ester) | amide |
| isocyanate | amine | urea |
| epoxide | amine | alkyl-amine |
| hydroxyl amine | aldehyde, ketone | oxime |
| hydrazide | aldehyde, ketone | hydrazone |
| potassium acyl trifluoroborate | O-substituted hydroxylamine (e.g., O-carbamoylhydroxylamine) | amide |

Throughout the instant application, prefixes are used before the term "conjugation handle" to denote the functionality to which the conjugation handle is linked. For example, a "protein conjugation handle" is a conjugation handle attached to a protein (either directly or through a linker), an "antibody conjugation handle" is a conjugation handle attached to an antibody (either directly or through a linker), and a "linker conjugation handle" is a conjugation handle attached to a linker group (e.g., a bifunctional linker used to link a synthetic protein and an antibody).

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_i$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, -propyl, 1-methyl ethyl, -butyl, -pentyl, 1,1-dimethyl ethyl, 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—. Unless stated otherwise specifically in the specification, an alkylene group may be optionally substituted.

The term "alkenylene" or "alkenylene chain" refers to a straight or branched divalent hydrocarbon chain in which at least one carbon-carbon double bond is present linking the rest of the molecule to a radical group. In some embodiments, the alkenylene is —CH═CH—, —CH$_2$CH═CH—, or —CH═CHCH$_2$—. In some embodiments, the alkenylene is —CH═CH—. In some embodiments, the alkenylene is —CH$_2$CH═CH—. In some embodiments, the alkenylene is —CH═CHCH$_2$—.

The term "alkynyl" refers to a type of alkyl group in which at least one carbon-carbon triple bond is present. In one embodiment, an alkenyl group has the formula —C≡C—R$^x$, wherein R$^x$ refers to the remaining portions of the alkynyl group. In some embodiments, R$^x$ is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$, —C≡CCH$_2$CH, and —CH$_2$C°CH.

The term "aryl" refers to a radical comprising at least one aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted. In some embodiments, an aryl group comprises a partially reduced cycloalkyl group defined herein (e.g., 1,2-dihydronaphthalene). In some embodiments, an aryl group comprises a fully reduced cycloalkyl group defined herein (e.g., 1,2,3,4-tetrahydronaphthalene). When aryl comprises a cycloalkyl group, the aryl is bonded to the rest of the molecule through an aromatic ring carbon atom. An aryl radical can be a monocyclic or polycyclic (e.g., bicyclic, tricyclic, or tetracyclic) ring system, which may include fused, spiro or bridged ring systems.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopentyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1 (2H)-one, spiro[2.2]pentyl, norbornyl and bicycle[1.1.1]pentyl. Unless otherwise stated specifically in the specification, a cycloalkyl group may be optionally substituted.

The term "heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —CH$_2$—O—CH$_2$—, —CH$_2$—N(alkyl)-CH$_2$—, —CH$_2$—N(aryl)-CH$_2$—, —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

The term "heteocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" refers to an aryl group that includes one or more ring heteroatoms selected from nitrogen, oxygen, and sulfur. In some embodiments, heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_8$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group comprises a partially reduced cycloalkyl or heterocycloalkyl group defined herein (e.g., 7,8-dihydroquinoline). In some embodiments, a heteroaryl group comprises a fully reduced cycloalkyl or heterocycloalkyl group defined herein (e.g., 5,6,7,8-tetrahydroquinoline). When heteroaryl comprises a cycloalkyl or heterocycloalkyl group, the heteroaryl is bonded to the rest of the molecule through a heteroaromatic ring carbon or hetero atom. A heteroaryl radical can be a monocyclic or polycyclic (e.g., bicyclic, tricyclic, or tetracyclic) ring system, which may include fused, spiro or bridged ring systems.

The term "optionally substituted" or "substituted" means that the referenced group is optionally substituted with one or more additional group(s) individually and independently selected from D, halogen, —CN, —NH2, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$ ($C_1$-$C_4$alkyl), —C(=O)NH$_2$, —C(=O)NH($C_1$-$C_4$alkyl), —C(=O)N($C_1$-$C_4$alkyl)$_2$, —S(=O)$_2$NH$_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O) $C_1$-$C_4$alkyl, and —S(=O)$_2$$C_1$-$C_4$alkyl. In some embodiments, optional substituents are independently selected from D, halogen, —CN, —NH$_2$, —OH, —NH(CH$_3$), —N(CH$_3$)$_2$, —NH (cyclopropyl), —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

Anti-TNFα Polypeptides Conjugated to Cytokines

"Human TNF-alpha" (abbreviated herein as hTNF-alpha, TNFα, or hTNFα), as used herein, is intended to refer to a human cytokine that exists in two forms: a type II transmembrane protein, and a mature soluble protein. The TNF-α transmembrane protein is proteolytically cleaved to yield a soluble, biologically active, 17 kDa TNF-α, which forms a non-covalently linked homotrimer in solution. Recombinant Human TNF-α is a soluble 157 amino acid protein (17.4 kDa) which corresponds to C-terminal extracellular domain of the full-length transmembrane protein. A human TNFα transmembrane protein can have an amino acid sequence of (SEQ ID NO: 48)
MSTESMIRDVELAEEALPKKTGGPQGSRRCLFLSLFSFLIVAGATTLFCL

LHFGVIGPQREEFPRDLSLISPLAQAVRSSSRTPSDKPVAHVVANPQAEG

QLQWLNRRANALLANGVELRDNQLVVPSEGLYLIYSQVLFKGQGCPSTHV

-continued

LLTHTISRIAVSYQTKVNLLSAIKSPCQRETPEGAEAKPWYEPIYLGGVF

QLEKGDRLSAEINRPDYLDFAESGQVYFGIIAL.

A recombinant, mature human TNFα can have an amino acid sequence of (SEQ ID NO: 49)
VRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL.

Provided herein are polypeptides, such as antibodies and antigen binding fragments thereof, which bind to TNFα which are conjugated to one or more cytokine molecules or derivatives thereof. The polypeptide conjugates provided herein are effective for simultaneously delivering the cytokine and the polypeptide which selectively binds to TNFα to a target cell. This simultaneous delivery of both agents to the same cell has numerous benefits, including improved IL-2 polypeptide selectivity and enhanced therapeutic potential of IL-2.

The conjugate compositions provided herein utilize linkers to attach the polypeptides which bind to TNFα to the cytokines, such as IL-2 polypeptides and derivatives thereof. In some embodiments, the linkers are attached to each moiety the polypeptide which selectively binds to TNFα and the cytokine) at specific residues or a specific subset of residues. In some embodiments, the linkers are attached to each moiety in a site-selective manner, such that a population of the conjugate is substantially uniform. This can be accomplished in a variety of ways as provided herein, including by site-selectively adding reagents for a conjugation reaction to a moiety to be conjugated, synthesizing, or otherwise preparing a moiety to be conjugated with a desired reagent for a conjugation reaction, or a combination of these two approaches. Using these approaches, the sites of attachment (such as specific amino acid residues) of the linker to each moiety can be selected with precision. Additionally, these approaches allow a variety of linkers to be employed for the composition which are not limited to amino acid residues as is required for fusion proteins. This combination of linker choice and precision attachment to the moieties allows the linker to also, in some embodiments, perform the function of modulating the activity of one of the moieties, for example if the linker is attached to the cytokine at a position that interacts with a receptor of the cytokine.

Anti-TNFα Polypeptides

In some embodiments, an anti-TNFα polypeptide or an anti-TNFα antigen binding fragment of the disclosure selectively binds to TNFα. An antibody selectively binds or preferentially binds to a target if it binds with greater affinity, avidity, more readily, and/or with greater duration than it binds to other substances. As such, "specific binding" or "preferential binding" does not necessarily require (although it can include) exclusive binding. Generally, but not necessarily, reference to specific binding means preferential binding where the affinity of the antibody, or antigen binding fragment thereof, is at least at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody for unrelated amino acid sequences. An anti-TNFα polypeptide or an anti-TNFα antigen binding fragment of the disclosure can block interaction of TNFα with a ligand (e.g., a TNFα receptor). TNFα exerts many of its effects by binding, as a trimer, to either a 55 kDa cell membrane receptor termed TNFR1 or a 75 kDa cell membrane receptor termed TNFR2.

As used herein, the term "antibody" refers to an immunoglobulin (Ig), polypeptide, or a protein having a binding domain which is, or is homologous to, an antigen binding domain. The term further includes "antigen binding fragments" and other interchangeable terms for similar binding fragments as described below. Native antibodies and native immunoglobulins (Igs) are generally heterotetrameric glycoproteins of about 150,000 Daltons, composed of two identical light chains and two identical heavy chains. Each light chain is typically linked to a heavy chain by one covalent disulfide bond. while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

In some instances, an antibody or an antigen binding fragment comprises an isolated antibody or antigen binding fragment, a purified antibody or antigen binding fragment, a recombinant antibody or antigen binding fragment, a modified antibody or antigen binding fragment, or a synthetic antibody or antigen binding fragment.

Antibodies and antigen binding fragments herein can be partly or wholly synthetically produced. An antibody or antigen binding fragment can be a polypeptide or protein having a binding domain which can be, or can be homologous to, an antigen binding domain. In one instance, an antibody or an antigen binding fragment can be produced in an appropriate in vivo animal model and then isolated and/or purified.

Depending on the amino acid sequence of the constant domain of its heavy chains, immunoglobulins (Igs) can be assigned to different classes. There are five major classes of immunoglobulins: IgA, IgD, IgE, IgG, and IgM, and several of these may be further divided into subclasses (isotypes), e.g., IgG1. IgG2, IgG3, IgG4, IgA1 and IgA2. An Ig or portion thereof can, in some cases, be a human Ig. In some instances, a $C_H3$ domain can be from an immunoglobulin. In some cases, a chain or a part of an antibody or antigen binding fragment, a modified antibody or antigen binding fragment, or a binding agent can be from an Ig. In such cases, an Ig can be IgG, an IgA, an IgD, an IgE, or an IgM, or is derived therefrom. In cases where the Ig is an IgG, it can be a subtype of IgG, wherein subtypes of IgG can include IgG1, an IgG2a, an IgG2b, an IgG3, or an IgG4. In some cases, a $C_H3$ domain can be from an immunoglobulin selected from the group consisting of an IgG, an IgA, an IgD, an IgE, and an IgM, or is derived therefrom. In some embodiments, an antibody or antigen binding fragment described herein comprises an IgG or is derived therefrom.

In some instances, an antibody or antigen binding fragment comprises an IgG1 or is derived therefrom. In some instances, an antibody or antigen binding fragment comprises an IgG4 or is derived therefrom. In some embodiments, an antibody or antigen binding fragment described herein comprises an IgM, is derived therefrom, or is a monomeric form of IgM. In some embodiments, an antibody or antigen binding fragment described herein comprises an IgE or is derived therefrom. In some embodiments, an antibody or antigen binding fragment described herein comprises an IgD or is derived therefrom. In some embodiments, an antibody or antigen binding fragment described herein comprises an IgA or is derived therefrom.

The "light chains" of antibodies (immunoglobulins) from any vertebrate species can be assigned to one of two clearly distinct types, called kappa ("K" or "κ") or lambda ("λ"), based on the amino acid sequences of their constant domains.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (Kabat et al., Sequences of Proteins of Immunological Interest, 5th Ed., 1991, National Institutes of Health, Bethesda Md., pages 647-669; hereafter "Kabat"); and (2) an approach based on crystallographic studies of antigen-antibody complexes (Al-lazikani et al. (1997) *J. Molec. Biol.* 273:927-948)). As used herein, a CDR may refer to CDRs defined by either approach or by a combination of both approaches.

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3, and FR4), largely adopting a β-sheet configuration interspersed with three CDRs which form loops connecting and, in some cases, part of the β-sheet structure. The CDRs in each chain are held together in close proximity by the FRs and, with the CDRs from the other chain, contribute to the formation of the antigen binding site of antibodies (see, Kabat).

The terms "hypervariable region" and "CDR" when used herein, refer to the amino acid residues of an antibody which are responsible for antigen binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2), and 89-97 (CDRL3), and in the heavy chain variable domain the CDRs typically correspond to approximately residues 31-35 (CDRH1), 50-65 (CDRH2), and 95-102 (CDRH3) according to Kabat et al., Id. It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2), and 91-96 (CDRL3), and in the heavy chain variable domain, the CDRs typically correspond to approximately residues 26-32 (CDRH1), 53-55 (CDRH2), and 96-101 (CDRH3) according to Chothia and Lesk (*J. Mol. Biol.*, 196:901-917 (1987)).

As used herein, "framework region," "FW," or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat. As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, Id. The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three-dimensional structure of the antibody variable domain can be derived from a crystal structure or protein modeling.

In the present disclosure, the following abbreviations (in the parentheses) are used in accordance with the customs, as necessary: heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is generally defined to stretch from an amino acid residue at position Cys226, or from Pro230, to the carboxyl-terminus thereof. The numbering of the residues in the Fc region is that of the EU index as in Kabat). The Fc region of an immunoglobulin generally comprises two constant domains, $C_H2$ and $C_H3$.

"Antibodies" useful in the present disclosure encompass, but are not limited to, monoclonal antibodies, polyclonal antibodies, chimeric antibodies, bispecific antibodies, multispecific antibodies, heteroconjugate antibodies, humanized antibodies, human antibodies, grafted antibodies, deimmunized antibodies, mutants thereof, fusions thereof, immunoconjugates thereof, antigen binding fragments thereof, and/or any other modified configuration of the immunoglobulin molecule that comprises an antigen recognition site of the required specificity, including glycosylation variants of antibodies, amino acid sequence variants of antibodies, and covalently modified antibodies. In certain embodiments of the methods and conjugates provided herein, the antibody requires an Fc region to enable attachment of a linker between the antibody and the protein (e.g., attachment of the linker using an affinity peptide, such as in AJICAP™ technology).

In some instances, an antibody is a monoclonal antibody. As used herein, a "monoclonal antibody" refers to an antibody obtained from a population of substantially homogeneous antibodies, i.e., the individual antibodies comprising the population are identical except for possible naturally-occurring mutations that may be present in minor amounts. In contrast to polyclonal antibody preparations, which typically include different antibodies directed against different determinants (epitopes), each monoclonal antibody is directed against a single determinant on the antigen (epitope). The modifier "monoclonal" indicates the character of the antibody as being obtained from a substantially homogeneous population of antibodies and is not to be construed as requiring production of the antibody by any particular method.

In some instances, an antibody is a humanized antibody. As used herein, "humanized" antibodies refer to forms of non-human (e.g., murine) antibodies that are specific chimeric immunoglobulins, immunoglobulin chains, or fragments thereof that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences but are included to further refine and optimize antibody performance. In general, a humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in, for example, WO 99/58572. Other forms of humanized antibodies have one or more CDRs (one, two, three, four, five, or six) which are altered with respect to the original antibody, which are also termed one or more CDRs "derived from" one or more CDRs from the original antibody.

If needed, an antibody or an antigen binding fragment described herein can be assessed for immunogenicity and, as needed. be deimmunized (i.e., the antibody is made less immunoreactive by altering one or more T cell epitopes). As used herein, a "deimmunized antibody" means that one or more T cell epitopes in an antibody sequence have been modified such that a T cell response after administration of the antibody to a subject is reduced compared to an antibody that has not been deimmunized. Analysis of immunogenicity and T-cell epitopes present in the antibodies and antigen binding fragments described herein can be carried out via the use of software and specific databases. Exemplary software and databases include iTope™ developed by Antitope of Cambridge, England. iTope™, is an in silico technology for analysis of peptide binding to human MHC class II alleles. The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in silico generation of 9mer peptides that overlap by one amino acid spanning the test antibody variable region sequence. Each 9mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7, and P9) and the possible T cell receptor (TCR) contact residues (P-1, P2, P3, P5, P8). After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

An antibody can be a human antibody. As used herein, a "human antibody" means an antibody having an amino acid sequence corresponding to that of an antibody produced by a human and/or that has been made using any suitable technique for making human antibodies. This definition of a human antibody includes antibodies comprising at least one human heavy chain polypeptide or at least one human light chain polypeptide. One such example is an antibody comprising murine light chain and human heavy chain polypeptides. In one embodiment, the human antibody is selected from a phage library, where that phage library expresses human antibodies. Human antibodies can also be made by introducing human immunoglobulin loci into transgenic animals, e.g., mice in which the endogenous immunoglobulin genes have been partially or completely inactivated. Alternatively, the human antibody may be prepared by immortalizing human B lymphocytes that produce an antibody directed against a target antigen (such B lymphocytes may be recovered from an individual or may have been immunized in vitro).

Any of the antibodies herein can be bispecific. Bispecific antibodies are antibodies that have binding specificities for at least two different antigens and can be prepared using the antibodies disclosed herein. Traditionally, the recombinant production of bispecific antibodies was based on the co-expression of two immunoglobulin heavy chain-light chain pairs, with the two heavy chains having different specificities. Bispecific antibodies can be composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations.

According to one approach to making bispecific antibodies, antibody variable domains with the desired binding specificities (antibody-antigen combining sites) are fused to immunoglobulin constant domain sequences. The fusion can be with an immunoglobulin heavy chain constant domain, comprising at least part of the hinge, CH2 and CH3 regions. The first heavy chain constant region (CH1), containing the site necessary for light chain binding, can be present in at least one of the fusions. INAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some instances, an antibody herein is a chimeric antibody. "Chimeric" forms of non-human (e.g., murine) antibodies include chimeric antibodies which contain minimal sequence derived from a non-human Ig. For the most part, chimeric antibodies are murine antibodies in which at least a portion of an immunoglobulin constant region (Fc), typically that of a human immunoglobulin, is inserted in place of the murine Fc. Chimeric or hybrid antibodies also may be prepared in vitro using suitable methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Provided herein are antibodies and antigen binding fragments thereof, modified antibodies and antigen binding fragments thereof, and binding agents that specifically bind to one or more epitopes on one or more target antigens. In one instance, a binding agent selectively binds to an epitope on a single antigen. In another instance, a binding agent is bivalent and either selectively binds to two distinct epitopes on a single antigen or binds to two distinct epitopes on two distinct antigens. In another instance, a binding agent is multivalent (i.e., trivalent, quatravalent, etc.) and the binding agent binds to three or more distinct epitopes on a single antigen or binds to three or more distinct epitopes on two or more (multiple) antigens.

Antigen binding fragments of any of the antibodies herein are also contemplated. The terms "antigen binding portion of an antibody," "antigen binding domain," "antibody fragment," or a "functional fragment of an antibody" are used interchangeably herein to refer to one or more fragments of an antibody that retain the ability to specifically bind to an antigen. Representative antigen binding fragments include, but are not limited to, a Fab, a Fab', a F(ab')$_2$, a bispecific F(ab')$_2$, a trispecific F(ab')$_2$, a variable fragment (Fv), a single chain variable fragment (scFv), a dsFv, a bispecific scFv, a variable heavy domain, a variable light domain, a variable NAR domain, bispecific scFv, an AVIMER®, a minibody, a diabody, a bispecific diabody, triabody, a tetrabody, a minibody, a maxibody, a camelid, a VHH, a minibody, an intrabody, fusion proteins comprising an antibody portion (e.g., a domain antibody), a single chain binding polypeptide, a scFv-Fc, a Fab-Fc, a bispecific T cell engager (BiTE; two scFvs produced as a single polypeptide chain, where each scFv comprises an amino acid sequences a combination of CDRs or a combination of VL/VL described herein), a tetravalent tandem diabody (TandAb; an antibody fragment that is produced as a non-covalent homodimer folder in a head-to-tail arrangement, e.g., a TandAb comprising an scFv, where the scFv comprises an amino acid sequences a combination of CDRs or a combination of VL/VL described herein), a Dual-Affinity Re-targeting Antibody (DART; different scFvs joined by a stabilizing interchain disulphide bond), a bispecific antibody (bscAb; two single-chain Fv fragments joined via a glycine-serine linker), a single domain antibody (sdAb), a fusion protein, a bispecific disulfide-stabilized Fv antibody fragment (dsFv-dsFv'; two different disulfide-stabilized Fv antibody fragments connected by flexible linker peptides). In certain embodiments of the invention, a full length antibody (e.g., an antigen binding fragment and an Fc region) are preferred.

Heteroconjugate polypeptides comprising two covalently joined antibodies or antigen binding fragments of antibodies are also within the scope of the disclosure. Suitable linkers may be used to multimerize binding agents. Non-limiting examples of linking peptides include, but are not limited to, (GS)$_n$ (SEQ ID NO: 124), (GGS)$_n$ (SEQ ID NO: 125), (GGGS)$_n$ (SEQ ID NO: 126), (GGSG)$_n$ (SEQ ID NO: 127), or (GGSGG)$_n$ (SEQ ID NO: 128), (GGGGS)$_n$ (SEQ ID NO: 129), wherein n is 1, 2, 3, 4, 5, 6, 7, 8, 9, or 10. For example, a linking peptide can be (GGGGS)$_3$ (SEQ ID NO: 130) or (GGGGS)$_4$ (SEQ ID NO: 131). In some embodiments, a linking peptide bridges approximately 3.5 nm between the carboxy terminus of one variable region and the amino terminus of the other variable region. Linkers of other sequences have been designed and used. Linkers can in turn be modified for additional functions, such as attachment of drugs or attachment to solid supports.

As used herein, the term "avidity" refers to the resistance of a complex of two or more agents to dissociation after dilution. Apparent affinities can be determined by methods such as an enzyme-linked immunosorbent assay (ELISA) or any other suitable technique. Avidities can be determined by methods such as a Scatchard analysis or any other suitable technique.

As used herein, the term "affinity" refers to the equilibrium constant for the reversible binding of two agents and is expressed as KD. The binding affinity (KD) of an antibody or antigen binding fragment herein can be less than 500 nM, 475 nM, 450 nM, 425 nM, 400 nM, 375 nM, 350 nM, 325 nM, 300 nM, 275 nM, 250 nM, 225 nM, 200 nM, 175 nM, 150 nM, 125 nM, 100 nM, 90 nM, 80 nM, 70 nM, 50 nM, 50 nM, 49 nM, 48 nM, 47 nM, 46 nM, 45 nM, 44 nM, 43 nM, 42 nM, 41 nM, 40 nM, 39 nM, 38 nM, 37 nM, 36 nM, 35 nM, 34 nM, 33 nM, 32 nM, 31 nM, 30 nM, 29 nM, 28 nM, 27 nM, 26 nM, 25 nM, 24 nM, 23 nM, 22 nM, 21 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 990 pM, 980 pM, 970 pM, 960 pM, 950 pM, 940 pM, 930 PM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM. 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM. 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM. 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, or any integer therebetween. Binding affinity may be determined using surface plasmon resonance (SPR), KINEXA® Biosensor, scintillation proximity assays, enzyme linked immunosorbent assay (ELISA), ORIGEN immunoassay (IGEN), fluorescence quenching, fluorescence transfer, yeast display, or any combination thereof. Binding affinity may also be screened using a suitable bioassay.

As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

Also provided herein are affinity matured antibodies. The following methods may be used for adjusting the affinity of an antibody and for characterizing a CDR. One way of characterizing a CDR of an antibody and/or altering (such as improving) the binding affinity of a polypeptide, such as an antibody, is termed "library scanning mutagenesis." Generally, library scanning mutagenesis works as follows. One or more amino acid position in the CDR is replaced with two or more (such as 3, 4, 5, 6, 7, 8, 9, 10, 11, 12, 13, 14, 15, 16, 17, 18, 19, or 20) amino acids. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, for example, about 20-80 clones (depending on the complexity of the library), from each library can be screened for binding specificity or affinity to the target polypeptide (or other binding target), and candidates with increased, the same, decreased, or no binding are identified. Binding affinity may be determined using Biacore surface plasmon resonance analysis, which detects differences in binding affinity of about 2-fold or greater.

In some instances, an antibody or antigen binding fragment is bispecific or multispecific and can specifically bind to more than one antigen. In some cases, such a bispecific or multispecific antibody or antigen binding fragment can specifically bind to 2 or more different antigens. In some cases, a bispecific antibody or antigen binding fragment can be a bivalent antibody or antigen binding fragment. In some cases, a multi specific antibody or antigen binding fragment can be a bivalent antibody or antigen binding fragment, a trivalent antibody or antigen binding fragment, or a quatravalent antibody or antigen binding fragment.

An antibody or antigen binding fragment described herein can be isolated, purified, recombinant, or synthetic.

The antibodies described herein may be made by any suitable method. Antibodies can often be produced in large quantities, particularly when utilizing high level expression vectors.

In one embodiment, an anti-TNFα antibody or an anti-TNFα antigen binding fragment of the disclosure comprises a combination of a heavy chain variable region (VH) and a light chain variable region (VL) described herein. In another embodiment, an anti-TNFα antibody or an anti-TNFα antigen binding fragment of the disclosure comprises a combination of complementarity determining regions (VH CDR1, VH CDR2, VH CDR3, VL CDR1, VL CDR2, and VL CDR3) described herein. In one embodiment, an anti-TNFα antibody or an anti-TNFα antigen binding fragment of the disclosure comprises a modified Adalimumab (HUMIRA®). In one embodiment, an anti-TNFα antibody or an anti-TNFα antigen binding fragment of the disclosure comprises a modified Infliximab (AVSOLA®).

In one embodiment, an anti-TNFα antibody or an anti-TNFα antigen binding fragment of the disclosure comprises a fusion protein or a peptide immunotherapeutic agent.

In one embodiment, an anti-TNF agent of the disclosure comprises a cell such as, for example, a CART cell or a cytotoxic T lymphocyte.

TABLE 1 provides the sequences of exemplary anti-TNFα polypeptides (e.g., anti-TNFα antibodies) that can be modified to prepare anti-TNFα immunoconjugates. TABLE 1 also provides exemplary combinations of CDRs that can be utilized in a modified anti-TNFα immunoconjugate. Reference to an anti-TNFα polypeptide herein may alternatively refer to an anti-TNFα antigen binding fragment.

TABLE 1

| Drug Name (Generic, Brand Name, Code Name) | Sequence | SEQ ID NO: |
|---|---|---|
| Adalimumab (HUMIRA ®) Heavy chain | EVQLVESGGGLVQPGRSLRLSCAASGFT FDDYAMHWVRQAPGKGLEWVSAITWNSG HIDYADSVEGRFTISRDNAKNSLYLQMN SLRAEDTAVYYCAKVSYLSTASSLDYWG QGTLVTVSSASTKGPSVFPLAPSSKSTS GGTAALGCLVKDYFPEPVTVSWNSGALT SGVHTFPAVLQSSGLYSLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSRDELTK NQVSLTCLVKGFYPSDIAVEWESNGQPE NNYKTTPPVLDSDGSFFLYSKLTVDKSR WQQGNVFSCSVMHEALHNHYTQKSLSLS PGK | 132 |
| Adalimumab (HUMIRA ®) Light chain | DIQMTQSPSSLSASVGDRVTITCRASQG IRNYLAWYQQKPGKAPKLLIYAASTLQS GVPSRFSGSGSGTDFTLTISSLQPEDVA TYYCQRYNRAPYTFGQGTKVEIKRTVAA PSVFIFPPSDEQLKSGTASVVCLLNNFY PREAKVQWKVDNALQSGNSQESVTEQDS KDSTYSLSSTLTLSKADYEKHKVYACEV THQGLSSPVTKSFNRGEC | 133 |

TABLE 1-continued

| Drug Name (Generic, Brand Name, Code Name) | Sequence | SEQ ID NO: |
|---|---|---|
| Infliximab (REMICADE ®; AVSOLA ®) VH | EVKLEESGGGLVQPGGSMKLSCVASGFI FSNHWMNWVRQSPEKGLEWVAEIRSKSI NSATHYAESVKGRFTISRDDSKSAVYLQ MTDLRTEDTGVYYCSRNYYGSTYDYWGQ GTTLTVSSASTKGPSVFPLAPSSKSTSG GTAALGCLVKDYFPEPVTVSWNSGALTS GVHTFPAVLQSSGLYSLSSVVTVPSSSL GTQTYICNVNHKPSNTKVDKKVEPKSCD KT | 134 |
| Infliximab (REMICADE ®; AVSOLA ®) VL | DILLTQSPAILSVSPGERVSFSCRASQF VGSSIHWYQQRTNGSPRLLIKYASESMS GIPSRFSGSGSGTDFTLSINTVESEDIA DYYCQQSHSWPFTFGSGTNLEVKRTVAA PSVFIFPPSDEQLKSGTASVVCLLNNFY PREAKVQWKVDNALQSGNSQESVTEQDS KDSTYSLSSTLTLSKADYEKHKVYACEV THQGLSSPVTKSFNRGEC | 135 |

An anti-TNFα polypeptide or an anti-TNFα antigen binding fragment comprises a VH having an amino acid sequence of SEQ ID NO: 132 or 134. An anti-TNFα polypeptide or an anti-TNFα antigen binding fragment comprises a VL having an amino acid sequence of SEQ ID NO: 133 or 135.

In one instance, an anti-TNFα polypeptide or an anti-TNF antigen binding fragment comprises a VH having an amino acid sequence of SEQ ID NO: 132 and a VL having an amino acid sequence of SEQ ID NO: 133. In another instance, an anti-TNFα polypeptide or an anti-TNFα antigen binding fragment comprises a VH having an amino acid sequence of SEQ ID NO: 134 and a VL having an amino acid sequence of SEQ ID NO: 135.

Modification to Fc Region, Including Points of Attachment

Disclosed herein are anti-TNFα polypeptides, wherein the anti-TNFα polypeptides comprise an Fc region, and the Fc region comprises at least one covalently liked chemical linker. The chemical linker can be covalently attached to an alanine, glycine, isoleucine, leucine, proline, valine, phenylalanine, tryptophan, tyrosine, aspartic acid, glutamic acid, arginine, histidine, lysine, serine, threonine, cysteine, methionine, asparagine, or glutamine residue of the Fc region. In some embodiments, the chemical linker is covalently attached to a glycine, tyrosine, aspartic acid, glutamic acid, arginine, histidine, or lysine residue. In some embodiments, the chemical linker is covalently attached to a lysine, cysteine, or methionine residue. In some embodiments, the chemical linker is covalently attached to a lysine residue. In some embodiments, the chemical linker is covalently attached to a constant region of the anti-TNFα polypeptide.

In some embodiments, the anti-TNFα polypeptide comprises an Fc region. In some embodiments, the Fc region is an IgG Fc region, an IgA Fc region, an IgD Fc region, an IgM Fc region, or an IgE Fc region. In some embodiments, the Fc region is an IgG Fc region, an IgA Fc region, or an IgD Fc region. In some embodiments, the Fc region is a human Fc region. In some embodiments, the Fc region is a humanized Fc region. In some embodiments, the Fc region is an IgG Fc region. In some instances, an IgG Fc region is an IgG1 Fc region, an IgG2a Fc region, or an IgG4 Fc region. In some instances, an IgG Fc region is an IgG1 Fc region, an IgG2a Fc region, or an IgG4 Fc region.

One or more mutations may be introduced in an Fc region to reduce Fc-mediated effector functions of an antibody or antigen-binding fragment such as, for example, antibody-dependent cellular cytotoxicity (ADCC) and/or complement function. In some instances, a modified Fc comprises a humanized IgG4 kappa isotype that contains a S229P Fc mutation. In some instances, a modified Fc comprises a human IgG1 kappa where the heavy chain CH₂ domain is engineered with a triple mutation such as, for example: (a) L238P, L239E, and P335S; or (2) K248; K288; and K317.

In some embodiments, the Fc region has an amino acid sequence at least 80%, at least 85%, at least 90%, at least 91%, at least 92%, at least 93%, at least 94%, at least 95%, at least 96%, at least 97%, at least 98%, or at least 99% identical to a sequence as set forth in SEQ ID NO: 136 (Pro Lys Ser Cys Asp Lys Thr His Thr Cys Pro Pro Cys Pro Ala Pro Glu Xaa Xaa Gly Xaa Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asp Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Xaa Glu Xaa Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Xaa Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly, where Xaa can be any naturally occurring amino acid).

In some embodiments, the Fc region comprises one or more mutations which make the Fc region susceptible to modification or conjugation at a particular residue, such as by incorporation of a cysteine residue at a position which does not contain a cysteine in SEQ ID NO: 136. Alternatively, the Fc region could be modified to incorporate a modified natural amino acid or an unnatural amino acid which comprises a conjugation handle, such as one connected to the modified natural amino acid or unnatural amino acid through a linker. In some embodiments, the chemical linker is attached to a native residue as set forth in SEQ ID NO: 136. In some embodiments, the chemical linker is attached to a native lysine residue of SEQ ID NO: 136.

In some embodiments, the chemical linker can be covalently attached to one amino acid residue of an Fc region of the anti-TNFα polypeptide. In some embodiments, the chemical linker is covalently attached to a non-terminal residue of the Fc region. In some embodiments, the non-terminal residue is in the CH1, CH2, or CH3 region of the anti-TNFα polypeptide. In some embodiments, the non-terminal residue is in the CH2 region of the anti-TNFα polypeptide.

In some embodiments, the chemical linker is attached to the Fc region at an amino acid residue at any one of positions 10-90 of SEQ ID NO: 136. In some embodiments, the chemical linker is attached to the Fc region at an amino acid residue at any one of positions 10-20, 10-30, 10-40, 10-50, 10-60, 10-70, 1-80, 10-90, 10-100, 10-110, 10-120, 10-130, 10-140, 10-150, 10-160, 10-170, 10-180, 10-190, or 10-200 of SEQ ID NO: 136. In some embodiments, the chemical linker is attached to the Fc region at an amino acid residue at any one of positions 20-40, 65-85, or 90-110 of SEQ ID NO: 136. In some embodiments, the chemical linker is attached to the Fc region at an amino acid residue at one of positions 10-30, 50-70, or 80-100 of SEQ ID NO: 136. In some embodiments, the chemical linker is attached to the Fc region at an amino acid residue at any one of positions 25-35, 70-80, or 95-105 of SEQ ID NO: 136. In some embodiments, the chemical linker is attached to the Fc region at an amino acid residue at one of positions 15-26, 55-65, or 85-90 of SEQ ID NO: 136. In some embodiments, the chemical linker is attached to the Fc region at an amino acid residue at any one of positions 30, 32, 72, 74, 79 or 101 of SEQ ID NO: 136. In some embodiments, the chemical linker is attached to the Fc region at an amino acid residue at any one of positions K30, K32, K72, K74, Q79, or K101 of SEQ ID NO: 136. In some embodiments, the chemical linker is attached to the Fc region at amino acid residue 30 of SEQ ID NO: 136. In some embodiment, the chemical linker is attached to the Fc region at amino acid residue 32 of SEQ ID NO: 136. In some embodiments, the chemical linker is attached to the Fc region at amino acid residue 72 of SEQ ID NO: 136. In some embodiments, the chemical linker is attached to the Fc region at amino acid residue 74 of SEQ ID NO: 136. In some embodiments, the chemical linker is attached to the Fc region at amino acid residue 79 of SEQ ID NO: 136. In some embodiments, the chemical linker is attached to the Fc region at amino acid residue 101 of SEQ ID NO: 136.

In some embodiments, the chemical linker is covalently attached at an amino acid residue of the polypeptide which selectively binds a cancer or inflammatory associated antigen (e.g., an anti-TNF-alpha antibody) such that the function of the polypeptide is maintained (e.g., without denaturing the polypeptide). For example, when the polypeptide is an antibody such as a human IgG (e.g., human IgG1), exposed lysine residues exposed glutamine residues and exposed tyrosine residues are present at the following positions (refer to web site imgt.org/IMGTScientificChart/Numbering/Hu_IGHGnber.html by EU numbering). Exemplary exposed Lysine Residues: $CH_2$ domain (position 246, position 248, position 274, position 288, position 290, position 317, position 320, position 322, and position 338) $CH_3$ domain (position 360, position 414, and position 439). Exemplary exposed Glutamine Residues: $CH_2$ domain (position 295). Exemplary exposed Tyrosine Residues: $CH_2$ domain (position 278, position 296, and position 300) $CH_3$ domain (position 436).

The human IgG, such as human IgG1, may also be modified with a lysine, glutamine, or tyrosine residue at any one of the positions listed above in order provide a residue which is ideally surface exposed for subsequent modification.

In some embodiments, the chemical linker is covalently attached at an amino acid residue in the constant region of an anti-TNFα antibody. In some embodiments, the chemical linker is covalently attached at an amino acid residue in the $CH_1$, $CH_2$, or $CH_3$ region. In some embodiments, the chemical inker is covalently attached at an amino acid residue in the $CH_2$ region. In some embodiments, the chemical linker may be covalently attached to one residue selected from the following groups of residues following EU numbering in human IgG Fc: amino acid residues 1-478, amino acid residues 2-478, amino acid residues 1-477, amino acid residues 2-477, amino acid residues 10-467, amino acid residues 30-447, amino acid residues 50-427, amino acid residues 100-377, amino acid residues 150-327, amino acid residues 200-327, amino acid residues 240-327, and amino acid residues 240-320.

In some embodiments, the chemical linker is covalently attached to one lysine or glutamine residue of a human IgG Fc region. In some embodiments, the chemical linker is covalently attached at Lys 246 of an Fc region of the anti-TNFα polypeptide, wherein amino acid residue position number is based on Eu numbering. In some embodiments, the chemical linker is covalently attached at Lys 248 of an Fc region of the anti-TNFα polypeptide, wherein amino acid residue position number is based on Eu numbering. In some embodiments, the chemical linker is covalently attached at Lys 288 of an Fc region of the anti-TNFα polypeptide, wherein amino acid residue position number is based on Eu numbering. In some embodiments, the chemical linker is covalently attached at Lys 290 of an Fc region of the anti-TNFα polypeptide, wherein amino acid residue position number is based on Eu numbering. In some embodiments, the chemical linker is covalently attached at Gln 295 of an Fc region of the antibody polypeptide, wherein amino acid residue position number is based on Eu numbering. In some embodiments, the chemical linker is covalently attached at Lys 317 of the anti-TNFα polypeptide, wherein amino acid residue position number is based on Eu numbering.

In some embodiments, the chemical linker can be covalently attached to an amino acid residue selected from a subset of amino acid residues. In some embodiments, the subset comprises two three, four, five, six, seven, eight, nine, or ten amino acid residues of an Fc region of the anti-TNFα polypeptide. In some embodiments, the chemical linker can be covalently attached to one of two lysine residues of an Fc region of the anti-TNFα polypeptide.

In some embodiments, the anti-TNFα polypeptide will comprise two linkers covalently attached to the Fc region of the anti-TNFα polypeptide. In some embodiments, each of the two linkers will be covalently attached to a different heavy chain of the anti-TNFα polypeptide. In some embodiments, each of the two linkers will be covalently attached to a different heavy chain of the anti-TNFα polypeptide at a residue position which is the same. In some embodiments, each of the two linkers will be covalently attached to a different heavy chain of anti-TNFα polypeptide at a residue position which is different. When the two linkers are covalently attached to residue positions which differ, any combination of the residue positions provided herein may be used in combination.

In some embodiments, a first chemical linker is covalently attached at Lys 248 of a first Fc region of the anti-TNFα polypeptide, and a second chemical linker is covalently attached at Lys 288 of a second Fc region of the anti-TNFα polypeptide, wherein residue position number is based on Eu numbering. In some embodiments, a first chemical linker is covalently attached at Lys 246 of a first Fc region of the anti-TNFα polypeptide, and a second chemical linker is covalently attached at Lys 288 of a second Fc region of the anti-TNFα polypeptide, wherein residue position number is based on Eu numbering. In some embodiments, a first chemical linker is covalently attached at Lys 248 of a first Fc region of the anti-TNFα polypeptide, and a second chemical linker is covalently attached at Lys 317 of a second Fc region of the anti-TNFα polypeptide, wherein residue position number is based on Eu numbering. In some embodiments, a first chemical linker is covalently attached at Lys 246 of a first Fc region of the anti-TNFα polypeptide, and a second chemical linker is covalently attached at Lys 317 of a second Fc region of the anti-TNFα polypeptide, wherein residue position number is based on Eu numbering. In some embodiments, a first chemical linker is covalently attached at Lys 288 of a first Fc region of the anti-TNFα polypeptide, and a second chemical linker is covalently attached at Lys 317 of a second Fc region of the anti-TNFα polypeptide, wherein residue position number is based on Eu numbering.

Method of Modifying an Fc Region

Also provided herein are method of preparing a modified Fc region of a polypeptide which selectively binds to tumor necrosis factor (TNFα), such as for the attachment of a linker, a conjugation handle, or the cytokine to the polypeptide which selectively binds to TNFα. A variety of methods for site-specific modification of Fc regions of antibodies or other polypeptides which bind to TNFα are known in the art.

Modification with an Affinity Peptide Configured to Site-Specifically Attach Linker to the Antibody In some embodiments, an Fc region is modified to incorporate a linker, a conjugation handle, or a combination thereof. In some embodiments, the modification is performed by contacting the Fc region with an affinity peptide bearing a payload configured to attach a linker or other group to the Fc region, such as at a specific residue of the Fc region. In some embodiments, the linker is attached using a reactive group which (e.g., a N-hydroxysuccinimide ester) forms a bond with a residue of the Fc region. In some embodiments, the affinity peptide comprises a cleavable linker. The cleavable linker is configured on the affinity peptide such that after the linker or other group is attached to the Fc region, the affinity peptide can be removed, leaving behind only the desired linker or other group attached to the Fc region. The linker or other group can then be used further to add attach additional groups, such as a cytokine or a linker attached to a cytokine, to the Fc region.

Non-limiting examples of such affinity peptides can be found at least in PCT Publication No. WO2018199337A1, PCT Publication No. WO2019240288A1, PCT Publication No. WO2019240287A1, and PCT Publication No. WO2020090979A1, each of which is incorporated by reference as if set forth herein in its entirety. In some embodiments, the affinity peptide is a peptide which has been modified to deliver the linker/conjugation handle payload one or more specific residues of the Fc region of the antibody. In some embodiments, the affinity peptide has at least 80%, 85%, 90%, 91%, 92%, 93%, 94%, 95%, 96%, 97%, 98%, 99%, or 100% sequence identify to a peptide selected from among (1) QETNPTEN-LYFQQKNMQCQRRFYEALHDPNLNEEQRNARIR-SIRDDDC (SEQ ID NO: 137); (2) QTADNQKNMQCQRRFYEALHDPNLNEEQRNARIR-SIRDDCSQSANLLAEAQQLNDAQA PQA (SEQ ID NO: 138); (3) QETKNMQCQRRFYEALHDPNLNEEQR-NARIRSIRDDDC (SEQ ID NO: 139); (4) QETFNKQCQRRFYEALHDPNLNEEQRNARIR-SIRDDDC (SEQ ID NO: 140); (5) QETFNMQCQRRF-YEALHDPNLNKEQRNARIRSIRDDDC (SEQ ID NO: 141); (6) QETFNMQCQRRFYEALHDPNLNEEQR-NARIRSIKDDC (SEQ ID NO: 142); (7) QETMQCQRRF-YEALHDPNLNEEQRNARIRSIKDDC (SEQ ID NO: 143); (8) QETQCQRRFYEALHDPNLNEEQRNARIR-SIKDDC (SEQ ID NO: 144); (9) QETCQRRF-YEALHDPNLNEEQRNARIRSIKDDC (SEQ ID NO: 145); (10) QETRGNCAYHKGQLVWCTYH (SEQ ID NO: 146); and (11) QETRGNCAYHKGQIIWCTYH (SEQ ID NO: 147), or a corresponding peptide which has been truncated at the N-terminus by one, two, three, four, or five residues.

An exemplary affinity peptide with cleavable linker and conjugation handle payload capable of attaching the payload to residue K248 of an antibody as provided herein is shown below (as reported in Matsuda et al., "Chemical Site-Specific Conjugation Platform to Improve the Pharmacokinetics and Therapeutic Index of Antibody-Drug Conjugates," *Mol. Pharmaceutics* 2021, 18, 11, 4058-4066:

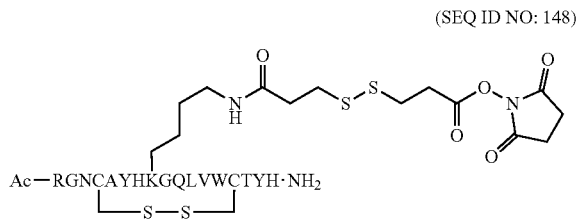

(SEQ ID NO: 148)

Alternative affinity peptides targeting alternative residues of the Fc region are described in the references cited above for AJICAP™ technology, and such affinity peptides can be used to attach the desired functionality to an alternative residue of the Fc region (e.g., K246, K288, etc.). For example, the disulfide group of the above affinity peptide could instead be replaced with a thioester to provide a sulfhydryl protecting group as a cleavable portion of the linking group (e.g., the relevant portion of the affinity peptide would have a structure of

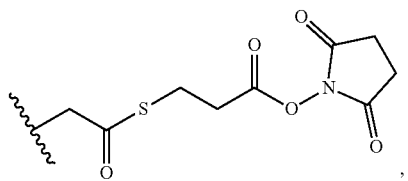 [SMILES: *CC(=O)SCCC(=O)ON1C(=O)CCC1=O]

or another of the cleavable linkers discussed below).

The affinity peptide of the disclosure can comprise a cleavable linker. In some embodiments, the cleavable linker of the affinity peptide connects the affinity peptide to the group which is to be attached to the Fc region and is configured such that the peptide can be cleaved after the group comprising the linker or conjugation handle has been attached. In some embodiments, the cleavable linker is a divalent group. In some embodiments, the cleavable linker can comprise a thioester group, an ester group, a sulfane group; a methanimine group; an oxyvinyl group; a thiopropanoate group; an ethane-1,2-diol group; an (imidazole-1-yl) methan-1-one group; a seleno ether group; a silylether group; a di-oxysilane group; an ether group; a di-oxymethane group; a tetraoxospiro[5.5]undecane group; an acetamidoethyl phosphoramidite group; a bis(methylthio)-pyrazolopyrazole-dione group; a 2-oxo-2-phenylethyl formate group; a 4-oxybenzylcarbamate group; a 2-(4-hydroxy-oxyphenyl)diazinyl)benzoic acid group; a 4-amino-2-(2-amino-2-oxoethyl)-4-oxobut-2-enoic acid group; a 2-(2-methylene-hydrazineyl)pyridine group; an N'-methyleneformohydrazide group; or an isopropylcarbamate group, any of which is unsubstituted or substituted. Composition and points of attachment of the cleavable linker to the affinity peptide, as well as related methods of use, are described in, at least, PCT Publication No. WO2018199337A1, PCT Publication No. WO2019240288A1, PCT Publication No. WO2019240287A1, and PCT Publication No. WO2020090979A1.

In some embodiments, the cleavable linker is:

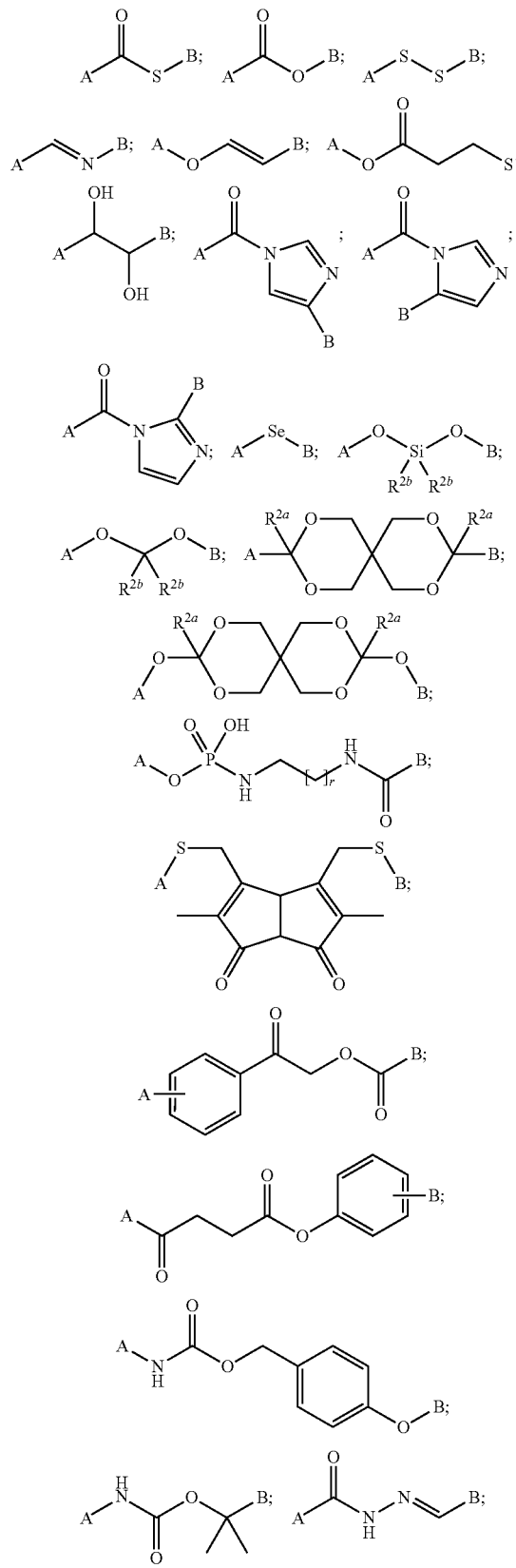

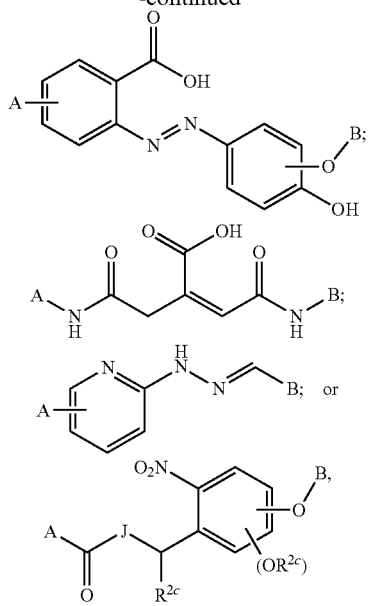

wherein:
one of A or B is a point of attachment the linker and the other of A or B is a point of attachment to the affinity peptide;
each $R^{2a}$ is independently H or optionally substituted alkyl;
each $R^{2b}$ is independently H or optionally substituted alkyl;
$R^{2c}$ is a H or optionally substituted alkyl;
J is a methylene, a N, a S, a Si, or an O atom; and
r is 1, 2, 3, 4, 5, 6, 7, 8, 9, or 10.

The affinity peptide comprises a reactive group which is configured to enable the covalent attachment of the linker/conjugation handle to the Fc region. In some embodiments, the reactive group is selective for a functional group of a specific amino acid residue, such as a lysine residue, tyrosine residue, serine residue. cysteine residue, or an unnatural amino acid residue of the Fc region incorporated to facilitate the attachment of the linker. The reactive group may be any suitable functional group, such as an activated ester for reaction with a lysine (e.g., N-hydroxysuccinimide ester or a derivate thereof, a pentafluorophenyl ester, etc.) or a sulfhydryl reactive group for reaction with a cysteine (e.g., a Michael acceptor, such as an alpha-beta unsaturated carbonyl or a maleimide). In some embodiments, the reactive group is:

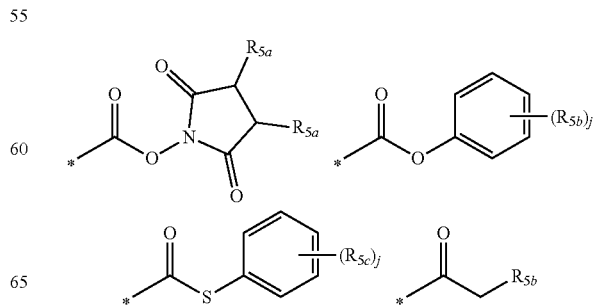

-continued

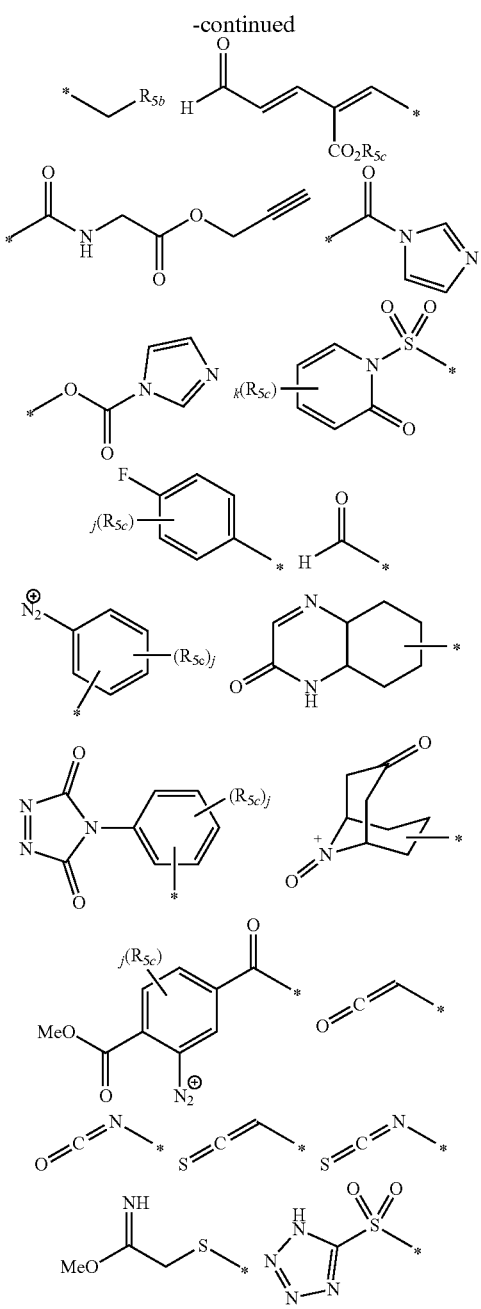

-continued or

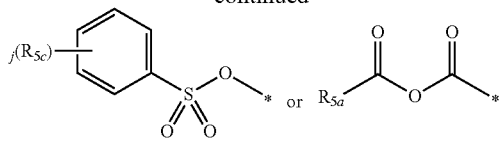

wherein:

each $R^{5a}$, $R^{5b}$, and $R^{5c}$ is independently H, halogen, or optionally substituted alkyl;

each j is 1, 2, 3, 4, or 5; and each k is 1, 2, 3, 4, or 5.

In some embodiments, the affinity peptide is used to deliver a reactive moiety to the desired amino acid residue such that the reactive moiety is exposed upon cleavage of the cleavable linker. By way of non-limiting example, the reactive group forms a covalent bond with a desired residue of the Fc region of the polypeptide which selectively binds to anti-TNFα due to an interaction between the affinity peptide and the Fc region. Following this covalent bond formation, the cleavable linker is cleaved under appropriate conditions to reveal a reactive moiety (e.g., if the cleavable linker comprises a thioester, a free sulfhydryl group is attached to the Fc region following cleavage of the cleavable linker). This new reactive moiety can then be used to subsequently add an additional moiety, such as a conjugation handle, by way of reagent comprising the conjugation handle tethered to a sulfhydryl reactive group (e.g., alpha-halogenated carbonyl group, alpha-beta unsaturated carbonyl group, maleimide group, etc.).

In some embodiments, an affinity peptide is used to deliver a free sulfhydryl group to a lysine of the Fc region. In some embodiments, the free sulfhydryl group is then reacted with a bifunctional linking reagent to attach a new conjugation handle to the Fc region. In some embodiments, the new conjugation handle is then used to form the linker to the attached cytokine. In some embodiments, the new conjugation handle is an alkyne functional group. In some embodiments, the new conjugation handle is a DBCO functional group.

Exemplary bifunctional linking reagents useful for this purpose are of a formula A-B-C, wherein A is the sulfhydryl reactive conjugation handle (e.g., maleimide, α,β-unsaturated carbonyl, a-halogenated carbonyl), B is a lining group, and C is the new conjugation handle (e.g., an alkyne such as DBCO). Specific non-limiting examples of bifunctional linking reagents include

,

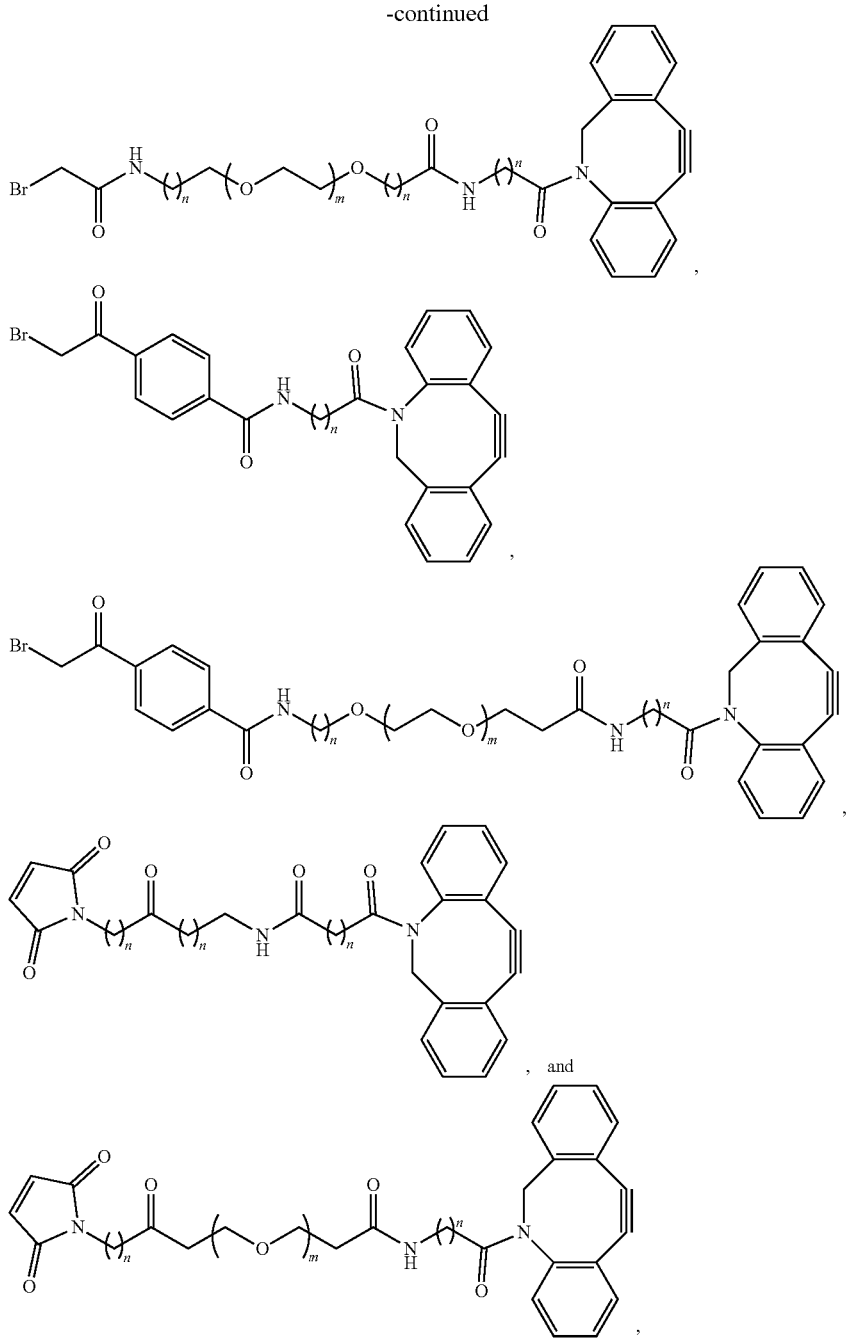

wherein each n is independently an integer from 1-6 and each m is independently an integer from 1-30, and related molecules (e.g., isomers).

Alternatively, the affinity peptide can be configured such that a conjugation handle is added to the Fc region (such as by a linker group) immediately after covalent bond formation between the reactive group and a residue of the Fc region. In such cases, the affinity peptide is cleaved and the conjugation handle is immediately ready for subsequent conjugation to the IL-2 polypeptide (or other cytokine).

Alternative Methods of Attachment—Enzyme Mediated

While the affinity peptide mediated modification of an Fc region of an antibody provided supra possesses many advantages over other methods which can be used to site-specifically modify the Fc region (e.g., ease of use, ability to rapidly generate many different antibody conjugates, ability to use many "off-the-shelf" commercial antibodies without the need to do time consuming protein engineering, etc.), other methods of performing the modification are also contemplated as being within the scope of the present disclosure.

In some embodiments, the present disclosure relates generally to transglutaminase-mediated site-specific antibody-drug conjugates (ADCs) comprising: 1) glutamine-containing tags, endogenous glutamines (e.g., native glutamines without engineering, such as glutamines in variable domains, CDRs, etc.), and/or endogenous glutamines made reactive by antibody engineering or an engineered transglutaminase; and 2)amine donor agents comprising amine donor units, linkers, and agent moieties. Non-limiting examples of such transglutaminase mediated site-specific modifications can be found at least in publications WO2020188061, US 2022133904, US2019194641, US2021128743, U.S. Pat. Nos. 9,764,038, 10,675,359, 9,717,803, 10,434,180, 9,427,478, which are incorporated by reference as if set forth herein in their entirety.

In another aspect, the disclosure provides an engineered Fc-containing polypeptide conjugate comprising the formula: (Fc-containing polypeptide-T-A), wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX, wherein X is any amino acid (e.g., X can be the same or different amino acid), and wherein the engineered Fc-containing polypeptide conjugate comprises an amino acid substitution from glutamine to asparagine at position 295 (Q295N; EU numbering scheme).

In some embodiments, the acyl donor glutamine-containing tag is not spatially adjacent to a reactive Lys (e.g., the ability to form a covalent bond as an amine donor in the presence of an acyl donor and a transglutaminase) in the polypeptide or the Fc-containing polypeptide. In some embodiments, the polypeptide or the Fc-containing polypeptide comprises an amino acid modification at the last amino acid position in the carboxyl terminus relative to a wild-type polypeptide at the same position. The amino acid modification can be an amino acid deletion, insertion, substitution, mutation, or any combination thereof.

In some embodiments, the polypeptide conjugate comprises a full length antibody heavy chain and an antibody light chain, wherein the acyl donor glutamine-containing tag is located at the carboxyl terminus of a heavy chain, a light chain, or both the heavy chain and the light chain.

In some embodiments, the polypeptide conjugate comprises an antibody, wherein the antibody is a monoclonal antibody, a polyclonal antibody, a human antibody, a humanized antibody, a chimeric antibody, a bispecific antibody, a minibody, a diabody, or an antibody fragment. In some embodiments, the antibody is an IgG.

In another aspect, described herein is a method for preparing an engineered Fc-containing polypeptide conjugate comprising the formula: (Fc-containing polypeptide-T-A), wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX, wherein X is any amino acid (e.g., X can be the same or a different amino acid), and wherein the engineered Fc-containing polypeptide conjugate comprises an amino acid substitution from glutamine to asparagine at position 295 (Q295N; EU numbering scheme), comprising the steps of: a) providing an engineered (Fc-containing polypeptide)-T molecule comprising the Fc-containing polypeptide and the acyl donor glutamine-containing tag; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate.

In another aspect, described herein is a method for preparing an engineered polypeptide conjugate comprising the formula: polypeptide-T-A, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence LLQGPX (SEQ ID NO: 100), wherein X is A or P, or GGLLQGPP (SEQ ID NO: 101), comprising the steps of: a) providing an engineered polypeptide-T molecule comprising the polypeptide and the acyl donor glutamine-containing tag; b) contacting the amine donor agent with the engineered polypeptide-T molecule in the presence of a transglutaminase; and c) allowing the engineered polypeptide-T to covalently link to the amine donor agent to form the engineered Fc-containing polypeptide conjugate.

In some embodiments, the engineered polypeptide conjugate (e.g., the engineered Fc-containing polypeptide conjugate, the engineered Fab-containing polypeptide conjugate, or the engineered antibody conjugate) as described herein has conjugation efficiency of at least about 51%. In another aspect, the invention provides a pharmaceutical composition comprising the engineered polypeptide conjugate as described herein (e.g., the engineered Fc-containing polypeptide conjugate, the engineered Fab-containing polypeptide conjugate, or the engineered antibody conjugate) and a pharmaceutically acceptable excipient.

In some embodiments, described herein is a method for conjugating a moiety of interest (Z) to an antibody, comprising the steps of: (a) providing an antibody having (e.g., within the primary sequence of a constant region) at least one acceptor amino acid residue (e.g., a naturally occurring amino acid) that is reactive with a linking reagent (linker) in the presence of a coupling enzyme, e.g., a transamidase; and (b) reacting said antibody with a linking reagent (e.g., a linker comprising a primary amine) comprising a reactive group (R), optionally a protected reactive group or optionally an unprotected reactive group, in the presence of an enzyme capable of causing the formation of a covalent bond between the acceptor amino acid residue and the linking reagent (other than at the R moiety), under conditions sufficient to obtain an antibody comprising an acceptor amino acid residue linked (covalently) to a reactive group (R) via the linking reagent. Optionally, said acceptor residue of the antibody or antibody fragment is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further-within the $CH_2$ domain Optionally, the antibody is free of heavy chain N297-linked glycosylation. Optionally, the acceptor glutamine is at position 295 and the residue at the +2 position is the residue at position 297 (EU index numbering) of an antibody heavy chain.

In one aspect, described herein is a method for conjugating a moiety of interest (Z) to an antibody, comprising the steps of: (a) providing an antibody having at least one acceptor glutamine residue; and (b) reacting said antibody with a linker comprising a primary amine (a lysine-based linker) comprising a reactive group (R), preferably a protected reactive group, in the presence of a transglutaminase (TGase), under conditions sufficient to obtain an antibody comprising an acceptor glutamine linked (covalently) to a reactive group (R) via said linker. Optionally, said acceptor glutamine residue of the antibody or antibody fragment is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further-within the CH$_2$ domain Optionally, the antibody is free of heavy chain N297-linked glycosylation. Optionally, the acceptor glutamine is at position 295 and the residue at the +2 position is the residue at position 297 (EU index numbering) of an antibody heavy chain.

The antibody comprising an acceptor residue or acceptor glutamine residue linked to a reactive group (R) via a linker comprising a primary amine (a lysine-based linker) can thereafter be reacted with a reaction partner comprising a moiety of interest (Z) to generate an antibody comprising an acceptor residue or acceptor glutamine residue linked to a moiety of interest (Z) via the linker. Thus, in one embodiment, the method further comprises a step (c): reacting (i) an antibody of step b) comprising an acceptor glutamine linked to a reactive group (R) via a linker comprising a primary amine (a lysine-based linker), optionally immobilized on a solid support, with (ii) a compound comprising a moiety of interest (Z) and a reactive group (R') capable of reacting with reactive group R, under conditions sufficient to obtain an antibody comprising an acceptor glutamine linked to a moiety of interest (Z) via a linker comprising a primary amine (a lysine-based linker). Preferably, said compound comprising a moiety of interest (Z) and a reactive group (R') capable of reacting with reactive group R is provided at a less than 80 times, 40 times, 20 times, 10 times, 5 times or 4 molar equivalents to the antibody. In one embodiment, the antibody comprises two acceptor glutamines and the compound comprising a moiety of interest (Z) and a reactive group (R') is provided at 10 or less molar equivalents to the antibody. In one embodiment, the antibody comprises two acceptor glutamines and the compound comprising a moiety of interest (Z) and a reactive group (R') is provided at 5 or less molar equivalents to the antibody. In one embodiment, the antibody comprises four acceptor glutamines and the compound comprising a moiety of interest (Z) and a reactive group (R') is provided at 20 or less molar equivalents to the antibody. In one embodiment, the antibody comprises four acceptor glutamines and the compound comprising a moiety of interest (Z) and a reactive group (R') is provided at 10 or less molar equivalents to the antibody. In one embodiment, steps (b) and/or (c) are carried out in aqueous conditions. Optionally, step (c) comprises: immobilizing a sample of an antibody comprising a functionalized acceptor glutamine residue on a solid support to provide a sample comprising immobilized antibodies, reacting the sample comprising immobilized antibodies with a compound, optionally recovering any unreacted compound and re-introducing such recovered compound to the solid support for reaction with immobilized antibodies, and eluting the antibody conjugates to provide a composition comprising a Z moiety.

Conjugation Handle Chemistry

In some embodiments, the appropriately modified Fc region of the polypeptide which selectively binds to TNFα will comprise a conjugation handle which is used to conjugate the polypeptide which selectively binds to TNFα to an IL-2 polypeptide.

Any suitable reactive group capable of reacting with a complementary reactive group attached to the IL-2 polypeptide can be used as the conjugation handle. In some embodiments, the conjugation handle comprises a reagent for a Cu(I)-catalyzed or "copper-free" alkyne-azide triazole-forming reaction (e.g., strain promoted cycloadditions), the Staudinger ligation, inverse-electron-demand Diels-Alder (IEDDA) reaction, "photo-click" chemistry, tetrazine cycloadditions with trans-cyclooctenes, or a metal-mediated process such as olefin metathesis and Suzuki-Miyaura or Sonogashira cross-coupling.

In some embodiments, the conjugation handle comprises a reagent for a "copper-free" alkyne azide triazole-forming reaction. Non-limiting examples of alkynes for said alkyne azide triazole forming reaction include cyclooctyne reagents (e.g., (1R,8S,9s)-Bicyclo[6.1.0]non-4-yn-9-ylmethanol containing reagents, dibenzocyclooctyne-amine reagents, difluorocyclooctynes, or derivatives thereof). In some embodiments, the alkyne functional group is attached to the Fc region. In some embodiments, the azide functional group is attached to the Fc region.

In some embodiments, the conjugation handle comprises a reactive group selected from azide, alkyne, tetrazine, halide, sulfhydryl, disulfide, maleimide, activated ester, alkene, aldehyde, ketone, imine, hydrazine, and hydrazide. In some embodiments, the IL-2 polypeptide comprises a reactive group complementary to the conjugation handle of the Fc region. In some embodiments, the conjugation handle and the complementary conjugation handle comprise "CLICK" chemistry reagents. Exemplary groups of click chemistry residue are shown in Hein et al., "Click Chemistry, A Powerful Tool for Pharmaceutical Sciences," Pharmaceutical Research volume 25, pages 2216-2230 (2008); Thirumurugan et al., "Click Chemistry for Drug Development and Diverse Chemical-Biology Applications," Chem. Rev. 2013, 113, 7, 4905-4979; US20160107999A1; US. Pat. No. 10,266,502B2; and US20190204330A1, each of which is incorporated by reference in its entirety.

Linker Structure

In some embodiments, the linker used to attach the polypeptide which selectively binds to TNFα and the cytokine (such as the IL-2 polypeptide) comprises points of attachment at both moieties. The points of attachment can be any of the residues for facilitating the attachment as provided herein. The linker structure can be any suitable structure for creating the spatial attachment between the two moieties. In some embodiments, the linker provides covalent attachment of both moieties. In some embodiments, the linker is a chemical linker (e.g., not an expressed polypeptide as in a fusion protein).

In some embodiments, the linker comprises a polymer. In some embodiments, the linker comprises a water soluble polymer. In some embodiments, the linker comprises poly (alkylene oxide), polysaccharide, poly(vinyl pyrrolidone), poly(vinyl alcohol), polyoxazoline, poly(acryloylmorpholine), or a combination thereof. In some embodiments, the linker comprises poly(alkylene oxide). In some embodiments, the poly(alkylene oxide) is polyethylene glycol or polypropylene glycol, or a combination thereof. In some embodiments, the poly(alkylene oxide) is polyethylene glycol.

In some embodiments, the linker is a bifunctional linker. In some embodiments, the bifunctional linker comprises an amide group, an ester group, an ether group, a thioether group, or a carbonyl group. In some embodiments, the linker comprises a non-polymer linker. In some embodiments, the linker comprises a non-polymer, bifunctional linker. In some embodiments, the non-polymer, bifunctional linker comprises succinimidyl 4-(N-maleimidomethyl)cyclohexane-1-carboxylate; Maleimidocaproyl; Valine-citrulline; Allyl(4-methoxyphenyl)dimethylsilane; 6-(Allyloxycarbonylamino)-1-hexanol; 4-Aminobutyraldehyde diethyl acetal; or (E)-N-(2-Aminoethyl)-4-{2-[4-(3-azidopropoxy)phenyl]diazenyl}benzamide hydrochloride.

The linker can be branched or linear. In some embodiments, the linker is linear. In some embodiments, the linker is branched. In some embodiments, the linker comprises a linear portion (e.g., between the first point of attachment and the second point of attachment) of a chain of at least 10, 20, 50, 100, 500, 1000, 2000, 3000, or 5000 atoms. In some embodiments, the linker comprises a linear portion of a chain of at least 10, 20, 30, 40, or 50 atoms. In some embodiments, the linker comprises a liner portion of a chain of at most 30, 40, 50, 60, 70, 80, 90, or 100 atoms. In some embodiments, the linker comprises a linear portion of at least 10 atoms. In some embodiments, the linker is branched and comprises a linear portion of a chain of at least 10, 20, 50, 100, 500, 1000, 2000, 3000, or 5000 atoms. In some embodiments, the linker comprises a linear portion of a chain of at most about 300, 250, 200, 150, 100, or 50 atoms.

In some embodiments, the linker has a molecular weight of about 200 Daltons to about 2000 Daltons. In some embodiments, the linker has a molecular weight of about 200 Daltons to about 5000 Daltons. In some embodiments, the linker has a molecular weight of 200 Daltons to 100,000 Daltons. In some embodiments, the linker has a molecular weight of 200 Daltons to 500 Daltons, 200 Daltons to 750 Daltons, 200 Daltons to 1,000 Daltons, 200 Daltons to 5,000 Daltons, 200 Daltons to 10,000 Daltons, 200 Daltons to 20,000 Daltons, 200 Daltons to 50,000 Daltons, 200 Daltons to 100,000 Daltons, 500 Daltons to 750 Daltons, 500 Daltons to 1,000 Daltons, 500 Daltons to 5,000 Daltons, 500 Daltons to 10,000 Daltons, 500 Daltons to 20,000 Daltons, 500 Daltons to 50,000 Daltons, 500 Daltons to 100,000 Daltons, 750 Daltons to 1,000 Daltons, 750 Daltons to 5,000 Daltons, 750 Daltons to 10,000 Daltons, 750 Daltons to 20,000 Daltons, 750 Daltons to 50,000 Daltons, 750 Daltons to 100,000 Daltons, 1,000 Daltons to 5,000 Daltons, 1,000 Daltons to 10,000 Daltons, 1,000 Daltons to 20,000 Daltons, 1,000 Daltons to 50,000 Daltons, 1,000 Daltons to 100,000 Daltons, 5,000 Daltons to 10,000 Daltons, 5,000 Daltons to 20,000 Daltons, 5,000 Daltons to 50,000 Daltons, 5,000 Daltons to 100,000 Daltons, 10,000 Daltons to 20,000 Daltons, 10,000 Daltons to 50,000 Daltons, 10,000 Daltons to 100,000 Daltons, 20,000 Daltons to 50,000 Daltons, 20,000 Daltons to 100,000 Daltons, or 50,000 Daltons to 100,000 Daltons. In some embodiments, the linker has a molecular weight of 200 Daltons, 500 Daltons, 750 Daltons, 1,000 Daltons, 5,000 Daltons, 10,000 Daltons, 20,000 Daltons, 50,000 Daltons, or 100,000 Daltons. In some embodiments, the linker has a molecular weight of at least 200 Daltons, 500 Daltons, 750 Daltons, 1,000 Daltons, 5,000 Daltons, 10,000 Daltons, 20,000 Daltons, or 50,000 Daltons. In some embodiments, the linker has a molecular weight of at most 500 Daltons, 750 Daltons, 1,000 Daltons, 5,000 Daltons, 10,000 Daltons, 20,000 Daltons, 50,000 Daltons, or 100,000 Daltons.

In some embodiments, the linker comprises a reaction product one or more pairs of conjugation handles and a complementary conjugation handle thereof. In some embodiments, the reaction product comprises a triazole, a hydrazone, pyridazine, a sulfide, a disulfide, an amide, an ester, an ether, an oxime, an alkene, or any combination thereof. In some embodiments, the reaction product comprises a triazole. The reaction product can be separated from the first point of attachment and the second point of attachment by any portion of the linker. In some embodiments, the reaction product is substantially in the center of the linker. In some embodiments, the reaction product is substantially closer to one point of attachment than the other.

In some embodiments, the linker comprises a structure of Formula (X)

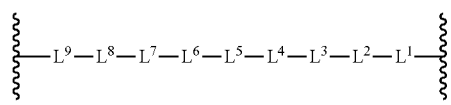

wherein each of L1, L2, L3, L4, L', L6, L8, and L' is independently —O—, —NR$^L$—, —N(R$^L$)$_2$$^+$—, —OP(=O)(OR$^L$)O—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted C$_1$-C$_6$ alkylene, substituted or unsubstituted C$_1$-C$_6$ heteroalkylene, substituted or unsubstituted C$_2$-C$_6$ alkenylene, substituted or unsubstituted C$_2$-C$_6$ alkynylene, substituted or unsubstituted C$_6$-C$_{20}$ arylene, substituted or unsubstituted C$_2$-C$_{20}$ heteroarylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, a reaction product of a conjugation handle and a complementary conjugation handle, or absent;

each R$^L$ is independently hydrogen, substituted or unsubstituted C$_1$-C$_4$ alkyl, substituted or unsubstituted C$_1$-C$_4$ heteroalkyl, substituted or unsubstituted C$_2$-C$_6$ alkenyl, substituted or unsubstituted C$_2$-C$_8$ alkynyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; and each of qa, qb, qc and qd is independently an integer from 1-100, wherein each

is a point of attachment to the polypeptide which selectively binds to TNFα or the cytokine (e.g., the IL-2 polypeptide).

In some embodiments, the linker comprises a structure of Formula (X$^a$)

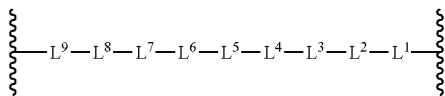

wherein each of $L^1, L^2, L^3, L^4, L^5, L^6, L^7, L^8$, and $L^9$ is independently —O—, —NR$^L$—, —(C$_1$-C$_6$ alkylene)NR$^L$—, —NR$^L$(C$_1$-C$_6$ alkylene)-, —N(R$^L$)$_2^+$—, —(C$_1$-C$_6$ alkylene)N(R$^L$)$_2^+$—, —N(R$^L$)$_2^+$—(C$_1$-C$_6$ alkylene)-, —OP(=O)(OR$^L$)O—, —S—, —(C$_1$-C$_6$ alkylene)S—, —S(C$_1$-C$_6$ alkylene)-, —S(=O)—, —S(=O)$_2$—, —C(=O)—, —(C$_1$-C$_6$ alkylene)C(=O)—, —C(=O)(C$_1$-C$_6$ alkylene)-, —C(=O)O—, —OC(=O)—, —OC(=O)O—, —C(=O)NR$^L$—, —C(=O)NR$^L$(C$_1$-C$_6$ alkylene)-, —(C$_1$-C$_6$ alkylene)C(=O)NR$^L$—, —NR$^L$C(=O)—, —(C$_1$-C$_6$ alkylene)NR$^L$C(=O)—, —NR$^L$C(=O)(C$_1$-C$_6$ alkylene)-, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted C$_1$-C$_6$ alkylene, substituted or unsubstituted C$_1$-C$_6$ heteroalkylene, substituted or unsubstituted C$_2$-C$_6$ alkenylene, substituted or unsubstituted C$_2$-C$_6$ alkynylene, substituted or unsubstituted C$_6$-C$_{20}$ arylene, substituted or unsubstituted C$_2$-C$_{20}$ heteroarylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, a reaction product of a conjugation handle and a complementary conjugation handle, or absent; (C$_1$-C$_6$ alkylene)

each R$^L$ is independently hydrogen, substituted or unsubstituted C$_1$-C$_4$ alkyl, substituted or unsubstituted C$_1$-C$_4$ heteroalkyl, substituted or unsubstituted C$_2$-C$_6$ alkenyl, substituted or unsubstituted C$_2$-C$_5$ alkynyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; and each of qa, qb, qc and qd is independently an integer from 1-100, wherein each

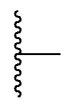

is a point of attachment to the polypeptide which selectively binds to TNFα or the cytokine (e.g., the IL-2 polypeptide).

In some embodiments, the linker comprises a structure of Formula (X')

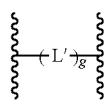

wherein each L' is independently —O—, —NR$^L$—, —(C$_1$-C$_6$ alkylene)NR$^L$—, —NR$^L$(C$_1$-C$_6$ alkylene)-, —N(R$^L$)$_2^+$—, —(C$_1$-C$_6$ alkylene)N(R$^L$)$_2^+$—, —N(R$^L$)$_2^+$—(C$_1$-C$_6$ alkylene)-, —OP(=O)(OR$^L$)O—, —S—, —(C$_1$-C$_6$ alkylene)S—, —S(C$_1$-C$_6$ alkylene)-, —S(=O)—, —S(=O)$_2$—, —C(=O)—, —(C$_1$-C$_6$ alkylene)C(=O)—, —C(=O)(C$_1$-C$_6$ alkylene)-, —C(=O)O—, —OC(=O)—, —OC(=O)O—, —C(=O)NR$^L$—, —C(=O)NR—(C$_1$-C$_6$ alkylene)-, —(C$_1$-C$_6$ alkylene)C(=O)NR$^L$—, —NR$^L$C(=O)—, —(C$_1$-C$_6$ alkylene)NR$^L$C(=O)—, —NR$^L$C(=O)(C$_1$-C$_6$ alkylene)-, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted C$_1$-C$_6$ alkylene, substituted or unsubstituted C$_1$-C$_6$ heteroalkylene, substituted or unsubstituted C$_2$-C$_6$ alkenylene, substituted or unsubstituted C$_2$-C$_6$ alkynylene, substituted or unsubstituted C$_6$-C$_{20}$ arylene, substituted or unsubstituted C$_2$-C$_{20}$ heteroarylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, a reaction product of a conjugation handle and a complementary conjugation handle, or absent; (C$_1$-C$_6$ alkylene);

each R$^L$ is independently hydrogen, substituted or unsubstituted C$_1$-C$_4$ alkyl, substituted or unsubstituted C$_1$-C$_4$ heteroalkyl, substituted or unsubstituted C$_2$-C$_6$ alkenyl, substituted or unsubstituted C$_2$-C$_5$ alkynyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; and each of qa, qb, qc and qd is independently an integer from 1-100, g is an integer from 1-100, wherein each

is a point of attachment to the modified IL-2 polypeptide or the antibody or antigen binding fragment.

In some embodiments, the linker of Formula (X) or of Formula (X$^a$) or of Formula (X') comprises the structure

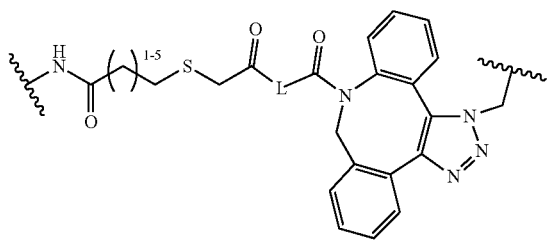

wherein

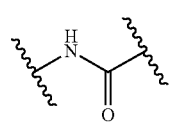

is the first point of attachment to a lysine residue of the polypeptide which selectively binds to TNFα;

L is a linking group; and

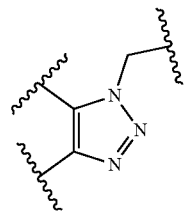 [SMILES: *Cn1nnc(*)c1*]

is a point of attachment to a linking group which connects to the first point of attachment, or a regioisomer thereof.

In some embodiments, L has a structure

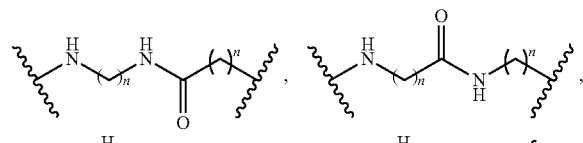

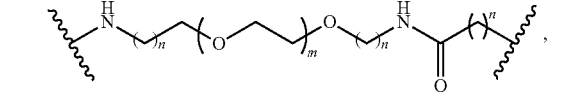

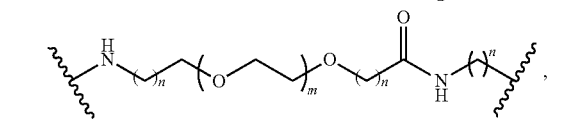

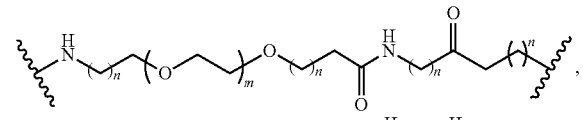

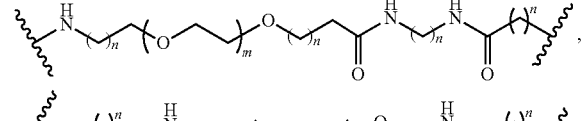

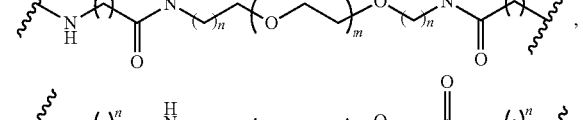

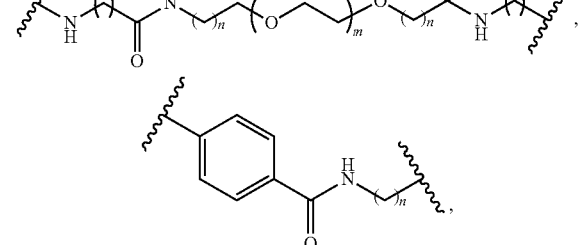

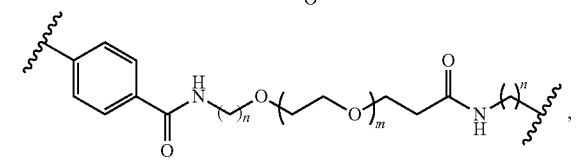

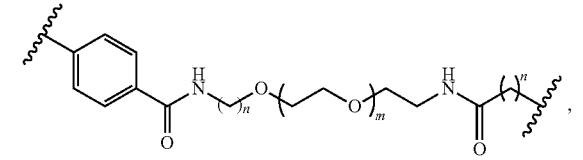

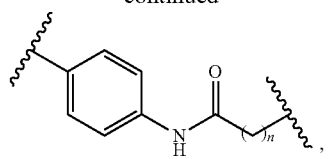

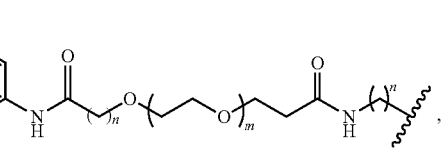

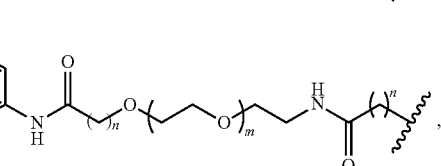

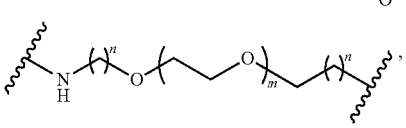

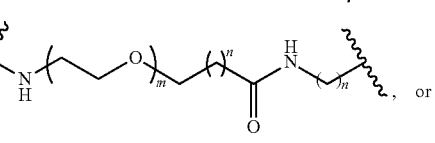

, or

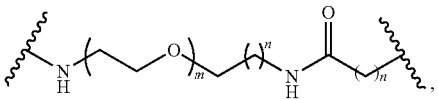

wherein each n is independently an integer from 1-6 and each m is an integer from 1-30. In some embodiments, each m is independently 2 or 3. In some embodiments, each m is an integer from 1-24, from 1-18, from 1-12, or from 1-6.

In some embodiments, the linker of Formula (X) or of Formula ($X^a$) or of Formula (X') comprises the structure:

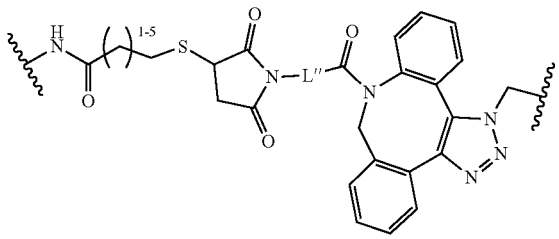

wherein

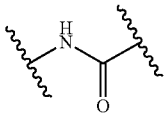

is the first point of attachment to a lysine residue of the polypeptide which selectively binds to TNFα;

L" is a linking group; and

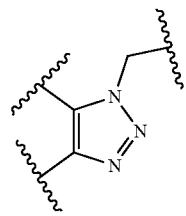 [SMILES: *Cn1nnc(*)c1*]

is a point of attachment to a linking group which connects to the first point of attachment,
or a regioisomer thereof.

In some embodiments, L" has a structure:

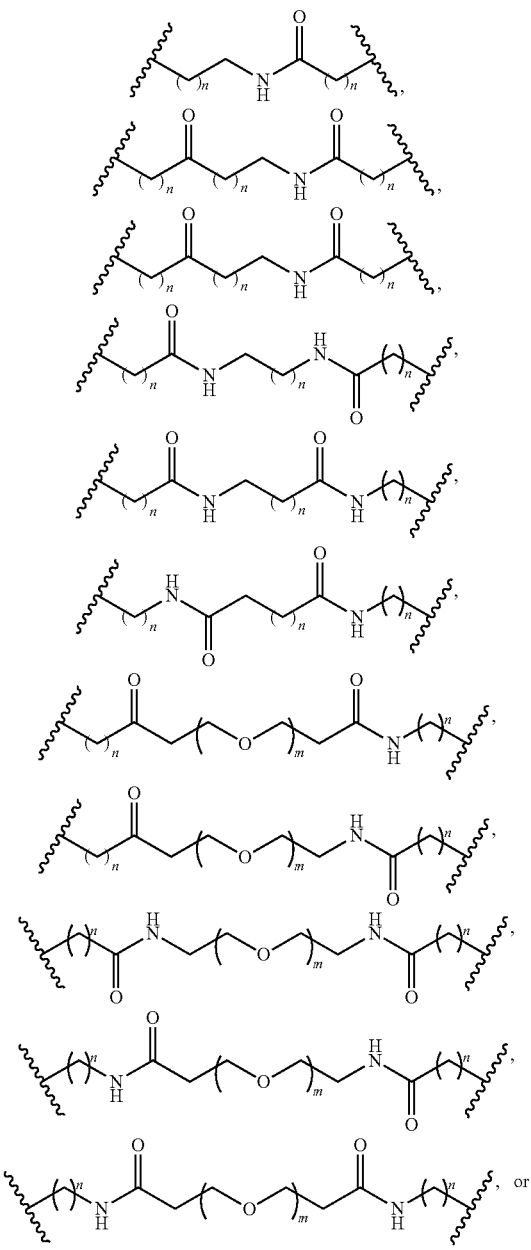

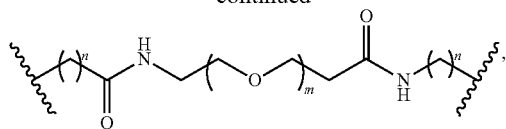

wherein each n is independently an integer from 1-6 and each m is independently an integer from 1-30. In some embodiments, each m is independently 2 or 3. In some embodiments, each m is an integer from 1-24, from 1-18, from 1-12, or from 1-6.

In some embodiments, L or L" comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more subunits each independently selected from

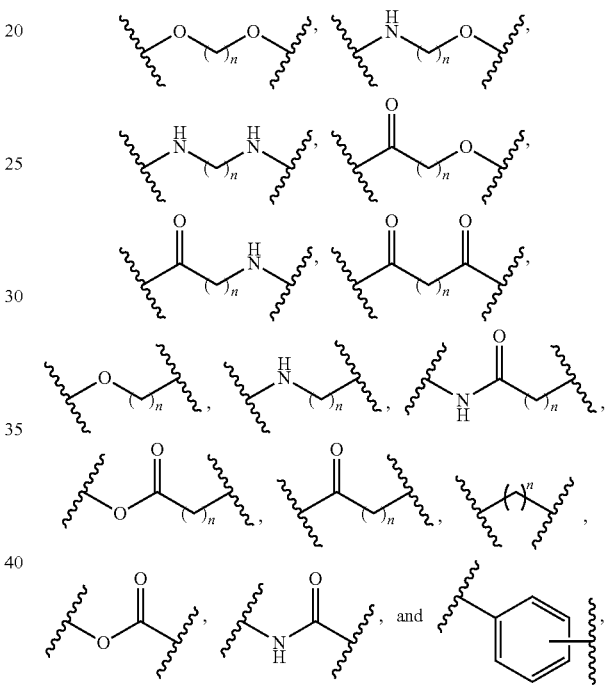

wherein each n is independently an integer from 1-30. In some embodiments, each n is independently an integer from 1-6. In some embodiments, L or L' comprise 1, 2, 3, 4, 5, 6, 7, 8, 9, or 10 of the subunits.

In some embodiments, L or L" is a structure of Formula (X")

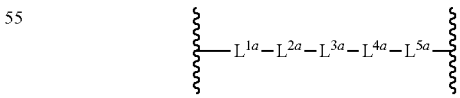

wherein each of $L^{1a}$, $L^{2a}$, $L^{3a}$, $L^{4a}$, $L^{5a}$, is independently
—O—, —NR$^{La}$—, —(C$_1$-C$_6$ alkylene)NR$^{La}$—, —NR$^{La}$(C$_1$-C$_6$ alkylene)-, —N(R$^L$)$_2$$^+$—, —(C$_1$-C$_6$ alkylene)N(R$^{La}$)$_2$$^+$(C$_1$-C$_6$ alkylene)-, —N(R$^L$)$_2$$^+$—, —OP(=O)(OR$^{La}$)O—, —S—, —(C$_1$-C$_6$ alkylene) S—, —S(C$_1$-C$_6$ alkylene)-, —S(=O)—, —S(=O)$_2$—, —C(=O)—, (C$_1$-C$_6$ alkylene)C(=O)—, —C(=O) (C$_1$-C$_6$ alkylene)-, —C(=O)O—, —OC(=O)—, —OC(=O)O—, —C(=O)NR$^{La}$—, —C(=O)NR$^{La}$(C$_1$-C$_6$ alkylene)-, —(C$_1$-C$_6$ alkylene) C(=O)NR$^{La}$—, —NR$^{La}$C(=O)—, —(C$_1$-C$_6$ alkylene)NR$^{La}$C(=O)—, —NR$^{La}$C(=O)(C$_1$-C$_6$ alkylene)-, —OC(=O)NR$^{La}$—, —NR$^{La}$C(=O)O—, —NR$^{La}$C(=O)NR$^{La}$—, —NR$^{La}$C(=S)NR$^{La}$—, —CR$^{La}$=N—, —N=CR$^{La}$, —NR$^{La}$S(=O)$_2$—, —S(=O)$_2$NR$^{La}$—, —C(=O)NR$^{La}$S(=O)$_2$—, —S(=O)$_2$NR$^{La}$C(=O)—, substituted or unsubstituted C$_1$-C$_6$ alkylene, substituted or unsubstituted C$_1$-C$_6$ heteroalkylene, substituted or unsubstituted C$_2$-C$_6$ alkenylene, substituted or unsubstituted C$_2$-C$_6$ alkynylene, substituted or unsubstituted C$_6$-C$_{20}$ arylene, substituted or unsubstituted C$_2$-C$_{20}$ heteroarylene, —(CH$_2$—CH$_2$—O)$_{qe}$—, —(O—CH$_2$—CH$_2$)$_{qf}$—, —(CH$_2$—CH(CH$_3$)—O)$_{qg}$—, —(O—CH(CH$_3$)—CH$_2$)$_{qh}$—, a reaction product of a conjugation handle and a complementary conjugation handle, or absent;

each R$^{La}$ is independently hydrogen, substituted or unsubstituted C$_1$-C$_4$ alkyl, substituted or unsubstituted C$_1$-C$_4$ heteroalkyl, substituted or unsubstituted C$_2$-C$_6$ alkenyl, substituted or unsubstituted C$_2$-C$_8$ alkynyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; and each of qe, qf, qg and qh is independently an integer from 1-100.

In some embodiments, L or L" comprises a linear chain of 2 to 10, 2 to 15, 2 to 20, 2 to 25, or 2 to 30 atoms. In some embodiments, the linear chain comprises one or more alkyl groups (e.g., lower alkyl (C$_1$-C$_4$)), one or more aromatic groups (e.g., phenyl), one or more amide groups, one or more ether groups, one or more ester groups, or any combination thereof.

In some embodiments, the linking group which connects to the first point of attachment (e.g., the point of attachment to the cytokine) comprises poly(ethylene glycol). In some embodiments, the linking group comprises about 2 to about 30 poly(ethylene glycol) units. In some embodiments, the linking group which connects to the first point of attachment (e.g., the point of attachment to the cytokine) is a functionality attached to a cytokine provided herein which comprises an azide (e.g., the triazole is the reaction product of the azide).

In some embodiments, L is —O—, —NR$^L$—, —N(R$^L$)$_2$$^+$—, —OP(=O)(OR$^L$)O—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted C$_1$-C$_6$ alkylene, substituted or unsubstituted C$_1$-C$_6$ heteroalkylene, substituted or unsubstituted C$_2$-C$_6$ alkenylene, substituted or unsubstituted C$_2$-C$_6$ alkynylene, substituted or unsubstituted C$_6$-C$_{20}$ arylene, substituted or unsubstituted C$_2$-C$_{20}$ heteroarylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, wherein R$^L$ hydrogen, substituted or unsubstituted C$_1$-C$_4$ alkyl, substituted or unsubstituted C$_1$-C$_4$ heteroalkyl, substituted or unsubstituted C$_2$-C$_6$ alkenyl, substituted or unsubstituted C$_2$-C$_8$ alkynyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; and each of qa, qb, qc and qd is independently an integer from 1-100.

In some embodiments, each reaction product of a conjugation handle and a complementary conjugation handle (e.g., as specified in Formula (X), Formula (X$^a$), Formula (X'), or Formula (X")) independently comprises a triazole, a hydrazone, pyridazine, a sulfide, a disulfide, an amide, an ester, an ether, an oxime, or an alkene. In some embodiments, each reaction product of a conjugation handle and a complementary conjugation handle comprises a triazole. In some embodiments, each reaction product of a conjugation handle and a complementary conjugation handle comprise a structure of

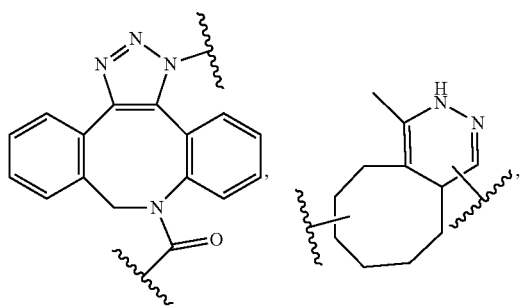

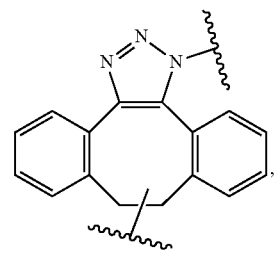

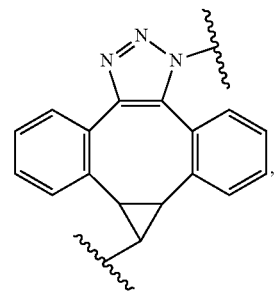

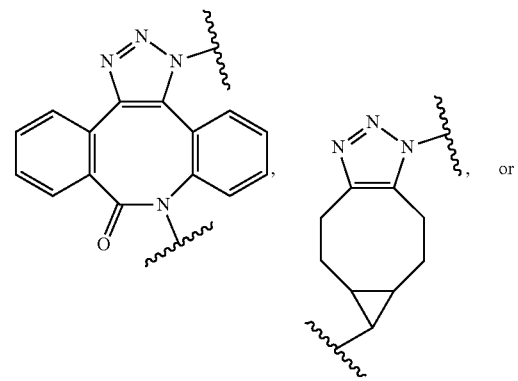

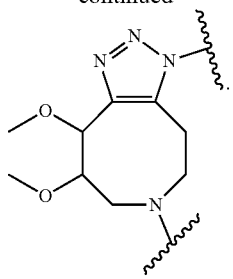

or a regioisomer or derivative thereof.

In some embodiments, the linker is a cleavable linker. In some embodiments, the cleavable linker is cleaved at, near, or in a tumor microenvironment. In some embodiments, the tumor is mechanically or physically cleaved at, near, or in the tumor microenvironment. In some embodiments, the tumor is chemically cleaved at, near, or in a tumor microenvironment. In some embodiments, the cleavable linker is a reduction sensitive linker. In some embodiments, the cleavable linker is an oxidation sensitive linker. In some embodiments, the cleavable linker is cleaved as a result of pH at, near, or in the tumor microenvironment. In some embodiments, the linker by a tumor metabolite at, near, or in the tumor microenvironment. In some embodiments, the cleavable linker is cleaved by a protease at, near, or in the tumor microenvironment.

IL-2 Cytokines

Cytokines are proteins produced in the body that are important in cell signaling. Cytokines can modulate the immune system, and cytokine therapy utilizes the immunomodulatory properties of the molecules to enhance the immune system of a subject. Disclosed herein are anti-TNFα polypeptides conjugated to cytokines, such as IL-2, which can exhibit enhanced biological activity.

Interleukin-2 (IL-2) is a cytokine signaling molecule important in regulating the immune system. IL-2 is implicated in helping the immune system differentiate between foreign and endogenous cell types, thereby preventing the immune system from attacking a subject's own cells. IL-2 accomplishes its activity through interactions with IL-2 receptors (IL-2R) expressed by lymphocytes. Through these binding interactions, IL-2 can modulate a subject's populations of T-effector ($T_{eff}$) cells, natural killer (NK) cells, and regulatory T-cells ($T_{reg}$).

Low-dose IL-2 is currently being explored for the treatment of various autoimmune disorders and has shown early signs of clinical efficacy. Conjugation of IL-2 to an anti-TNFα polypeptide of the disclosure can improve IL-2 polypeptide selectivity and enhance the therapeutic potential of IL-2.

The present disclosure describes anti-TNFα polypeptides conjugated to modified interleukin-2 (IL-2) polypeptides and their use as therapeutic agents. Modified IL-2 polypeptides provided herein can be used as immunotherapies or as parts of other immunotherapy regimens. Such modified IL-2 polypeptides may display binding characteristics for the IL-2 receptor (IL-2R) that differ from wild-type IL-2. Non-limiting examples of IL-2 amino acid sequences to be utilized in embodiments described herein are provided below in Table 4.

In a preferred aspect, the modified IL-2 polypeptide provided herein conjugated to an anti-TNFα polypeptide exhibits an ability to selectively activate $T_{reg}$ cells rather to other T cell subtypes. In some embodiments, the modified IL-2 polypeptides preferentially signal through the alpha receptor subunit of the IL-2 receptor compared to wild type IL-2, thereby preferentially enhancing and proliferating $T_{reg}$ populations compared to other T cell types. In some embodiments, the modified IL-2 polypeptides only minimally activate or proliferate other T cell types, such as $T_{eff}$ cells.

In some embodiments, the modified IL-2 polypeptides provided herein may comprise amino acid substitutions that enhance the binding affinity for the IL-2R alpha receptor subunit. In some embodiments, the modified IL-2 polypeptides provided herein comprise amino acid substitutions that lower the modified IL-2 polypeptides affinity for the IL-2R beta receptor subunit.

In some embodiments, the modified IL-2 polypeptides have a biological activity of more selectively activating and proliferating more T-regulatory ($T_{reg}$) cells compared to a wild type IL-2 or aldesleukin. In some embodiments, the modified IL-2 polypeptides are predicted to have a biological activity of proliferating and activating fewer T-effector ($T_{eff}$) cells when administered in vivo compared to a wild type IL-2 or aldesleukin.

Points of Attachment of Chemical Linkers to IL-2 Polypeptides

Provided herein are compositions comprising polypeptides, such as antibodies, which bind to TNFα that are connected to IL-2 polypeptides by a linker, such as a chemical linker. As discussed supra, the chemical linker can be attached to the anti-TNFα polypeptide at any of the positions provided herein. The second point of attachment of the linker is attached to an IL-2 polypeptide as provided herein.

In some embodiments, the chemical linker is attached to the IL-2 polypeptide at an amino acid residue. In some embodiments, the chemical linker is attached at an amino acid residue corresponding to any one of amino acid residues 1-133 of SEQ ID NO: 1. In some embodiments, the linker is attached to the N-terminal amino acid residue of the IL-2 polypeptide. In some embodiments, the linker is attached to the N-terminal amino group of the IL-2 polypeptide. In some embodiments, the linker is attached to the N-terminal amino group of the modified IL-2 polypeptide through by a reaction with an adduct attached to the N-terminal amino group having a structure

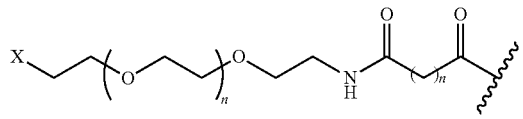

wherein each n is independently an integer from 1-30 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30), and wherein X is a conjugation handle (e.g., an azide or other conjugation handle provided herein, such as a DBCO group). In some embodiments, the adduct has the structure

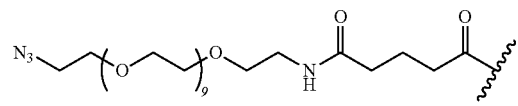

In some embodiments, the chemical linker is attached at a non-terminal amino acid residue (e.g., any one of amino acid residues 2-132 of SEQ ID NO: 1, or any one of amino acid residues 1-133 of SEQ ID NO: 1, wherein either the N-terminus or C-terminus has been extended by one or more amino acid residues). In some embodiments, the chemical linker is attached at a non-terminal amino acid residue of the IL-2 polypeptide, wherein the IL-2 polypeptide comprises either an N-terminal truncation or a C-terminal truncation relative to SEQ ID NO: 1. In some embodiments, the chemical linker is attached to a side chain of a non-terminal amino acid residue.

In some embodiments, the chemical linker is attached to the IL-2 polypeptide at an amino acid residue which interacts with an IL-2 receptor (IL-2R) protein or subunit. In some embodiments, the chemical linker is attached at an amino acid residue which interacts with the IL-2R alpha subunit (IL-2Rα), the IL-2R beta subunit (IL-2Rβ), or the IL-2R gamma subunit (IL-2Rγ). In some embodiments, the chemical linker is attached at an amino acid residue which interacts with the IL-2R alpha subunit. In some embodiments, the chemical linker is attached at an amino acid residue which interacts with the IL-2R beta subunit. In some embodiments, the chemical linker is attached at an amino acid residue which interacts with the IL-2R gamma subunit.

In some embodiments, the point of attachment to the IL-2 polypeptide is selected such that the interaction of the IL-2 polypeptide with at least one IL-2 receptor subunit is decreased or blocked. In some embodiments, the point of attachment is selected such that interaction of the IL-2 polypeptide with an IL-2 receptor containing the IL-2R alpha receptor subunit is unaffected or only slightly reduced. In some embodiments, the point of attachment is selected such that interaction of the IL-2 polypeptide with the IL-2 beta receptor subunit is substantially reduced. Examples of such residues are provided in US Publication No. US2020/0231644A1, which is hereby incorporated by reference as if set forth in its entirety. In some embodiments, the linker is attached to a residue at position 8, 9, 11, 12, 15, 16, 18, 19, 20, 22, 23, 26, 81, 84, 87, 88, 91, 92, 94, 95, 116, 119, 120, 123, 125, 126, 127, 130, 131, 132, or 133 of the IL-2 polypeptide, wherein residue position numbering is based on SEQ ID NO: 1 as a reference sequence. In some embodiments, the linker is attached to a residue at position 8, 9, 12, 15, 16, 19, 20, 22, 23, 26, 84, 88, 95, or 126 of the IL-2 polypeptide. In some embodiments, the linker is attached to a residue at position 8, 9, or 16. In some embodiments, the linker is attached to a residue at position 22, 26, 88, or 126 of the IL-2 polypeptide. In some embodiments, the linker is attached to a residue at position 15, 20, 84, or 95 of the IL-2 polypeptide. In some embodiments, the linker is attached to a residue at position 12, 19, or 23 of the IL-2 polypeptide. In some embodiments, the linker is attached to a residue at position 22 or 26. In some embodiments, the linker is attached to a residue at position 35 of the IL-2 polypeptide.

In some embodiments, the linker is attached to the IL-2 polypeptide at an amino acid residue at any one of positions 30-110, wherein residue position numbering of the modified IL-2 polypeptide is based on SEQ ID NO: 1 as a reference sequence. In some embodiments, the linker is attached to the IL-2 polypeptide at an amino acid residue at any one of positions 30-50, 30-70, 30-100, 40-50, 40-70, 40-100, or 40-110. In some embodiments, the linker is attached to the IL-2 polypeptide at an amino acid residue at any one of positions 35, 37, 38, 41, 42, 43, 44, 45, 60, 61, 62, 64, 65, 68, 69, 71, 72, 104, 105, and 107, wherein amino acid residue position numbering of the modified IL-2 polypeptide is based on SEQ ID NO: 1 as a reference sequence. In some embodiments, the linker is attached to the IL-2 polypeptide at an amino acid residue at any one of positions 35, 37, 38, 41, 42, 43, 44, 60, 61, 62, 64, 65, 68, 69, 71, 72, 104, 105, and 107, wherein amino acid residue position numbering of the modified IL-2 polypeptide is based on SEQ ID NO: 1 as a reference sequence. In some embodiments, the linker is attached to the IL-2 polypeptide at an amino acid residue at any one of positions 35, 37, 38, 41, 43, 44, 60, 61, 62, 64, 65, 68, 69, 71, 72, 104, 105, and 107, wherein amino acid residue position numbering of the modified IL-2 polypeptide is based on SEQ ID NO: 1 as a reference sequence In some embodiments, the linker is attached to the IL-2 polypeptide at an amino acid residue at any one of positions 35, 37, 38, 39, 40, 41, 42, 43, 44, 45, or 46. In some embodiments, the linker is attached to the IL-2 polypeptide at an amino acid residue at any one of positions 41, 42, 43, 44, and 45, wherein amino acid residue position numbering of the modified IL-2 polypeptide is based on SEQ ID NO: 1 as a reference sequence. In some embodiments, the linker is attached at amino acid residue 42 or 45. In some embodiments, the linker is attached at amino acid residue 42. In some embodiments, the linker is attached at amino acid residue 45.

In some embodiments, the linker is attached to a residue which is a natural amino acid residue of an IL-2 polypeptide as set forth in SEQ ID NO: 1. In some embodiments, the linker is attached to an amino acid residue which is a modified version of the natural amino acid residue of an IL-2 polypeptide as set forth in SEQ ID NO: 1. Non-limiting examples of such modification include incorporation or attachment of a conjugation handle to the natural amino acid residue (including through a linker), or attachment of the chemical linker to the natural amino acid using any compatible method. In some embodiments, the linker is attached to an amino acid residue which is a substituted amino acid residue compared to the IL-2 polypeptide of SEQ ID NO: 1. The substitution can be for a naturally occurring amino acid which is more amenable to attachment of additional functional groups (e.g., aspartic acid, cysteine, glutamic acid, lysine, serine, threonine, or tyrosine), a derivative of modified version of any naturally occurring amino acid, or any unnatural amino acid (e.g., an amino acid containing a desired reactive group, such as a CLICK chemistry reagent such as an azide, alkyne, etc.). Non-limiting examples of amino acids which can be substituted include, but are not limited to, -alpha-(9-Fluorenylmethyloxycarbonyl)-L-biphenylalanine (Fmoc-L-Bip-OH) and N-alpha-(9-Fluorenylmethyloxycarbonyl)-O-benzyl-L-tyrosine (Fmoc-L-Tyr (Bzl)-OH. Exemplary non-canonical amino acids include p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl) alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, azido-lysine (AzK), an analogue of a tyrosine amino acid; an analogue of a glutamine amino acid; an analogue of a phenylalanine amino acid; an analogue of a serine amino acid; an analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, a β-amino acid; a cyclic amino acid other than proline or histidine; an aromatic amino acid other than phenylalanine, tyrosine or tryptophan; or a combination thereof. In some embodiments, the non-canonical amino acids are selected from β-amino acids, homoamino acids, cyclic amino acids and amino acids with derivatized side chains. In some embodiments, the non-canonical amino acids comprise β-alanine, β-aminopropionic acid, piperidinic acid, aminocaprioic acid, aminoheptanoic acid, aminopimelic acid, desmosine, diaminopimelic acid, $N^\alpha$-ethylglycine, $N^\alpha$-ethylaspargine, hydroxylysine, allo-hydroxylysine, isodesmosine, allo-isoleucine, ω-methylarginine, $N^\alpha$-methylglycine, $N^\alpha$-methylisoleucine, $N^\alpha$-methylvaline, γ-carboxyglutamate, ε—N,N,N-trimethyllysine, ε—N-acetyllysine, O-phosphoserine, $N^\alpha$-acetylserine, $N^\alpha$-formylmethionine, 3-methylhistidine, 5-hydroxylysine, and/or other similar amino acids.

In some embodiments, the linker is attached at an unnatural amino acid residue. In some embodiments, the unnatural amino acid residue comprises a conjugation handle. In some embodiments, the conjugation handle facilitates the addition of the linker to the modified IL-2 polypeptide. The conjugation handle can be any of the conjugation handles provided herein. In some embodiments, the linker is covalently attached site-specifically to the unnatural amino acid. Non-limiting examples of amino acid residues comprising conjugation handles can be found, for example, in PCT Pub. Nos. WO2015054658A1, WO2014036492A1, and WO2021133839A1 WO2006069246A2, and WO2007079130A2, each of which is incorporated by reference as if set forth in its entirety.

In some embodiments, the linker is attached to an amino acid residue which has been substituted with a natural amino acid. In some embodiments, the linker is attached to an amino acid residue which has been substituted with a cysteine, lysine, or tyrosine residue. In some embodiments, the linker is attached to a residue which has been substituted with a cysteine residue. In some embodiments, the linker is attached to an amino acid residue which has been substituted with a lysine residue. In some embodiments, the linker is attached to an amino acid residue which has been substituted with a tyrosine residue. In some embodiments, the linker is attached to the amino terminal residue. In some embodiments, the linker is attached to amino acid residue A1.

Modifications to IL-2 Polypeptides

In some embodiments, the modified IL-2 polypeptides described herein contain one or more modified amino acid residues. Such modifications can take the form of mutations of a wild type IL-2 polypeptide such as the amino acid sequence of SEQ ID NO: 1, addition and/or deletion of amino acids from the sequence of SEQ ID NO: 1, or the addition of moieties to amino acid residues. In some embodiments, the modified IL-2 polypeptide described herein contains a deletion of the first amino acid from the sequence of SEQ ID NO: 1. In some embodiments, the modified IL-2 polypeptide described herein comprises a C125S mutation, using the sequence of SEQ ID NO: 1 as a reference sequence. Moieties which can be added to amino acid residues include, but are not limited to, polymers, linkers, spacers, and combinations thereof. When added to certain amino acid residues, these moieties can modulate the activity or other properties of the modified IL-2 polypeptide compared to wild-type IL-2.

In some embodiments, a modified IL-2 polypeptide provided herein comprises an N-terminal deletion. In some embodiments, the N-terminal deletion is of 1, 2, 3, 4, 5, 6, 7, 8, 9, 10, 11, 12, 13, 14, 15, or more amino acids. In some embodiments, the N-terminal deletion is of at least 1 amino acid. In some embodiments, the N-terminal deletion is of at least 1, 2, 3, 4, 5, 6, 7, 8, 9, or 10 amino acids. In some embodiments, the N-terminal deletion is from 1 to 15 amino acids. In some embodiments, the N-terminal deletion is a deletion of a single amino acid.

Modifications to the polypeptides described herein encompass mutations, addition of various functionalities, deletion of amino acids, addition of amino acids, or any other alteration of the wild-type version of the protein or protein fragment. Functionalities which may be added to polypeptides include polymers, linkers, alkyl groups, detectable molecules such as chromophores or fluorophores, reactive functional groups, or any combination thereof. In some embodiments, functionalities are added to individual amino acids of the polypeptides. In some embodiments, functionalities are added site-specifically to the polypeptides. In some embodiments, the functionality comprises at least a portion of the linker used to attach the IL-2 polypeptide to the polypeptide which selectively binds to TNFα.

In some embodiments, a modified IL-2 polypeptide described herein comprises at least 3, at least 4, at least 5, at least 6, at least 7, or at least 9 amino acid substitutions. In some embodiments, the modified IL-2 polypeptide comprises 3 to 9 amino acid substitutions. In some embodiments, the modified IL-2 polypeptide comprises 3 or 4 amino acid substitutions, 3 to 5 amino acid substitutions, 3 to 6 amino acid substitutions, 3 to 7 amino acid substitutions, 3 to 9 amino acid substitutions, 4 or 5 amino acid substitutions, 4 to 6 amino acid substitutions, 4 to 7 amino acid substitutions, 4 to 9 amino acid substitutions, 5 or 6 amino acid substitutions, 5 to 7 amino acid substitutions, 5 to 9 amino acid substitutions, 6 or 7 amino acid substitutions, 6 to 9 amino acid substitutions, or 7 to 9 amino acid substitutions. In some embodiments, the modified IL-2 polypeptide comprises 3 amino acid substitutions, 4 amino acid substitutions, 5 amino acid substitutions, 6 amino acid substitutions, 7 amino acid substitutions, or 9 amino acid substitutions. In some embodiments, the modified IL-2 polypeptide comprises at most 4 amino acid substitutions, 5 amino acid substitutions, 6 amino acid substitutions, 7 amino acid substitutions, or 9 amino acid substitutions.

In one aspect, provided herein is a modified IL-2 polypeptide comprising one or more amino acid substitutions. In some embodiments, the amino acid substitutions affect the binding properties of the modified IL-2 polypeptide to IL-2 receptor subunits (e.g. alpha, beta, or gamma subunits) or to IL-2 receptor complexes (e.g. IL-2 receptor αβγ complex or βγ complex). In some embodiments, the amino acid substitutions are at positions on the interface of binding interactions between the modified IL-2 polypeptide and an IL-2 receptor subunit or an IL-2 receptor complex. In some embodiments, the amino acid substitutions cause an increase in affinity for the IL-2 receptor αβγ complex or alpha subunit. In some embodiments, the amino acid substitutions cause a decrease in affinity for the IL-2 receptor βγ complex or beta subunit.

In some embodiments, a substituted residue in the IL-2 polypeptide is selected such that the interaction of the IL-2 polypeptide with at least one IL-2 receptor subunit is decreased or blocked. In some embodiments, the substituted residue is selected such that interaction of the IL-2 polypeptide with an IL-2 receptor containing the IL-2R alpha subunit is unaffected or only slightly reduced. In some embodiments, the substituted residue is selected such that the interaction of the IL-2 polypeptide with the IL-2R beta subunit is substantially reduced or blocked.

Examples of amino acid substitutions and other modifications which bias an IL-2 polypeptide in favor of the IL-2 receptor alpha subunit are described in, for example, Rao et al., Protein Eng. 2003 December; 16 (12): 1081-7; Cassell et al., Curr Pharm Des. 2002; 8(24):2171-83; Rao et al., Biochemistry. 2005 Aug. 9; 44(31)10696-701; Mitra et al., Immunity. 2015 May 19; 42(5)826-38; US Patent No. U.S. Pat. No. 9,732,134 and US Patent Publication No.: US2020/0231644A1, each of which is incorporated by reference as if set forth herein in its entirety. In some embodiments, the modified IL-2 polypeptide comprises one of the amino acid substitutions provided therein.

In some embodiments, the modified IL-2 polypeptide comprises one or more amino acid substitutions selected form Table 2.

TABLE 2

| WT IL-2 Residue Number* | WT IL-2 Residue | Substitutions or modification |
|---|---|---|
| 1 | A | Deletion |
| 18 | L | R, K |
| 22 | Q | N, H, K, Y, I, E |
| 23 | M | L, R, S, T, V, A |
| 29 | N | S |
| 31 | Y | H |
| 35 | K | R, E, D, Q |
| 37 | T | A, R |
| 46 | M | A |
| 48 | K | E, C |
| 69 | V | A |
| 71 | N | R |
| 74 | Q | P |
| 81 | R | A, G, S,T |
| 85 | L | V |
| 86 | I | V |
| 88 | N | A, D, E, F, G, H, I, M, Q, R, S, T, V, W |
| 89 | I | V |
| 92 | I | K, R |
| 125 | C | S, E, K, H, W, I, V, A |
| 126 | Q | A, C, D, E, F, G, H, I, K, L, M, N, R, S, T, Y |

*Residue position numbering based on SEQ ID NO: 1 as a reference sequence

In some embodiments, a modified IL-2 polypeptide provided herein comprises one or more amino acid substitutions selected from Table 3.

TABLE 3

| WT IL-2 Residue Number* | WT IL-2 Residue | Mutations |
|---|---|---|
| 18 | L | R |
| 22 | Q | E |
| 23 | M | A |
| 29 | N | S |
| 31 | Y | H |
| 35 | K | R |
| 37 | T | A |
| 39 | M | A |
| 42 | F | (4-NH$_2$)-Phe |
| 46 | M | A |
| 48 | K | E |
| 69 | V | A |
| 71 | N | R |
| 74 | Q | P |
| 80 | L | F |
| 81 | R | D |
| 85 | L | V |

TABLE 3-continued

| WT IL-2 Residue Number* | WT IL-2 Residue | Mutations |
|---|---|---|
| 86 | I | V |
| 88 | N | D, Dgp (gp = O-(2-aminoethyl)-O'-(2-aminoethyl)octaethylene glycol) |
| 89 | I | V |
| 92 | I | F |
| 126 | Q | T |

*Residue position numbering based on SEQ ID NO: 1 as a reference sequence

In some embodiments, the modified IL-2 polypeptide comprises one or more substitutions at one or more residues selected from 18, 22, 23, 29, 31, 35, 37, 39, 42, 46, 48, 69, 71, 74, 80, 81 85, 86, 88, 89, 92, and 126. In some embodiments, the modified IL-2 polypeptide comprises 1, 2, 3, 4, 5, 6, 7, or 8 substitutions at residues selected from 18, 22, 23, 29, 31, 35, 37, 39, 42, 46, 48, 69, 71, 74, 80, 81 85, 86, 88, 89, 92, and 126. In some embodiments, the modified IL-2 polypeptide comprises one or more substitutions selected from L18R, Q22E, M23A, N29S, Y31H, K35R, T37A, M39A, F42 (4-NH2)-Phe. M46A, K48E, V69A, N71R, Q74P, L80F, R81D, L85V, I86V, N88D, I89V, I92F, and Q126T. In some embodiments, the modified IL-2 polypeptide comprises 1, 2, 3, 4, 5, 6, 7, or 8 substitutions selected from L18R, Q22E, M23A, N29S, Y31H, K35R, T37A, M39A, F42 (4-NH2)-Phe, M46A, K48E, V69A, N71R, Q74P, L80F, R81D, L85V, I86V, N88D, I89V, I92F, and Q126T. In some embodiments, the modified IL-2 polypeptide comprises L18R. In some embodiments, the modified IL-2 polypeptide comprises Q22E. In some embodiments, the modified IL-2 polypeptide comprises M23A. In some embodiments, the modified IL-2 polypeptide comprises N29S. In some embodiments, the modified IL-2 polypeptide comprises Y31H. In some embodiments, the modified IL-2 polypeptide comprises K35R. In some embodiments, the modified IL-2 polypeptide comprises T37A. In some embodiments, the modified IL-2 polypeptide comprises M39A. In some embodiments, the modified IL-2 polypeptide comprises F42 (4-NH2)-Phe. In some embodiments, the modified IL-2 polypeptide comprises M46A. In some embodiments, the modified IL-2 polypeptide comprises K48E. In some embodiments, the modified IL-2 polypeptide comprises V69A. In some embodiments, the modified IL-2 polypeptide comprises N71R. In some embodiments, the modified IL-2 polypeptide comprises Q74P. In some embodiments, the modified IL-2 polypeptide comprises L80F. In some embodiments, the modified IL-2 polypeptide comprises R81D. In some embodiments, the modified IL-2 polypeptide comprises L85V. In some embodiments, the modified IL-2 polypeptide comprises I86V. In some embodiments, the modified IL-2 polypeptide comprises N88D. In some embodiments, the modified IL-2 polypeptide comprises I89V. In some embodiments, the modified IL-2 polypeptide comprises I92F. In some embodiments, the modified IL-2 polypeptide comprises Q126T.

In some embodiments, a modified IL-2 polypeptide provided herein comprises amino acid substitutions at at least one of Y31, K35, Q74, and N88D, wherein residue position numbering of the modified IL-2 polypeptide is based on SEQ ID NO: 1 as a reference sequence. In some embodiments, the modified IL-2 polypeptide comprises amino acid substitutions at at least two of Y31, K35, Q74, and N88. In some embodiments, the modified IL-2 polypeptide comprises amino acid substitutions at at least three of Y31, K35, Q74, and N88. In some embodiments, the modified IL-2 polypeptide. In some embodiments, the modified IL-2 polypeptide comprises amino acid substitutions at each of Y31, K35, Q74, and N88. In some embodiments, the modified IL-2 polypeptide comprises the amino acid substitutions Y31H, K35R, Q74P, and N88D. In some embodiments, the modified IL-2 polypeptide further comprises an optional C125 substitution (e.g., C125S or C125A). In some embodiments, the modified IL-2 polypeptide further comprises an optional A1 deletion or substitution of residue A1. In some embodiments, the modified IL-2 polypeptide further comprises an optional A1 deletion.

In some embodiments, a modified IL-2 polypeptide provided herein comprises natural amino acid substitutions at least one of Y31, K35, or Q74, wherein residue position numbering of the modified IL-2 polypeptide is based on SEQ ID NO:1 as a reference sequence. In some embodiments, the modified IL-2 polypeptide comprises natural amino acid substitutions at least two of Y31, K35, or Q74. In some embodiments, the modified IL-2 polypeptide. In some embodiments, the modified IL-2 polypeptide comprises natural amino acid substitutions at each of Y31, K35, and Q74. In some embodiments, the modified IL-2 polypeptide comprises the amino acid substitutions Y31H, K35R, and Q74P. In some embodiments, the modified IL-2 polypeptide further comprises an optional C125 mutation.

In some embodiments, a modified IL-2 polypeptide provided herein comprises a Y31 mutation wherein residue position numbering of the modified IL-2 polypeptide is based on SEQ ID NO: 1 as a reference sequence. In some embodiments, the Y31 mutation is for an aromatic amino acid. In some embodiments, the Y31 mutation is for a basic amino acid. In some embodiments, the basic amino acid is weakly basic. In some embodiments, the Y31 mutation is selected from Y31F, Y31H, Y31W, Y31R, and Y31K. In some embodiments, the Y31 mutation is Y31H.

In some embodiments, a modified IL-2 polypeptide provided herein comprises a K35 mutation, wherein residue position numbering of the modified IL-2 polypeptide is based on SEQ ID NO: 1 as a reference sequence. In some embodiments, the K35 mutation is for a basic amino acid. In some embodiments, the K35 mutation is for a positively charged amino acid. In some embodiments, the K35 mutation is K35R, K35E, K35D, or K35Q. In some embodiments, the K35 mutation is K35R.

In some embodiments, a modified IL-2 polypeptide provided herein comprises a Q74 mutation, wherein residue position numbering of the modified IL-2 polypeptide is based on SEQ ID NO: 1 as a reference sequence. In some embodiments, the Q74 mutation is a cyclic amino acid. In some embodiments, the cyclic amino acid comprises a cyclic group covalently attached to the alpha carbon and the nitrogen attached to the alpha carbon. In some embodiments, the Q74 mutation is Q74P.

In some embodiments, a modified IL-2 polypeptide provided herein comprises a N88 substitution, wherein residue position numbering of the modified IL-2 polypeptide is based on SEQ ID NO:1 as a reference sequence. In some embodiments, the N88 substitution is a charged amino acid residue. In some embodiments, the N88 substitution is a negatively charged amino acid residue. In some embodiments, the N88 substitution is N88D or N88E. In some embodiments, the N88 substitution is N88D or N88E. In some embodiments, the N88 substitution is N88D.

In some embodiments, a modified IL-2 polypeptide comprises a C125 mutation, wherein residue position numbering of the modified IL-2 polypeptide is based on SEQ ID NO:1 as a reference sequence. In some embodiments, the C125 mutation stabilizes the modified IL-2 polypeptide. In some embodiments, the C125 mutation does not substantially alter the activity of the modified IL-2 polypeptide. In some embodiments, the modified IL-2 polypeptide comprises a C125S mutation. In some embodiments, the modified IL-2 polypeptide comprises a $C_{125}A$ substitution.

In some embodiment, a modified IL-2 polypeptide comprises a modification at residue A1, wherein residue position numbering of the modified IL-2 polypeptide is based on SEQ ID NO: 1 as a reference sequence. In some embodiments, the modification is an A1 deletion. In some embodiments, a modified IL-2 polypeptide provided herein comprises an N-terminal deletion. In some embodiments, the N-terminal deletion is of 1, 2, 3, 4, 5, 6, 7, 8, 9, 10, 11, 12, 13, 14, 15, or more amino acids. In some embodiments, the N-terminal deletion is of at least 1 amino acid. In some embodiments, the N-terminal deletion is of at least 1, 2, 3, 4, 5, 6, 7, 8, 9, or 10 amino acids. In some embodiments, the N-terminal deletion is from 1 to 15 amino acids. In some embodiments, the N-terminal deletion is a deletion of a single amino acid (e.g., an A1 deletion of SEQ ID NO: 1).

In some embodiments, the modified IL-2 polypeptide comprises additional amino acid substitutions. In some embodiments, the modified IL-2 polypeptide comprises an additional amino acid substitution that has an effect on binding to the IL-2 receptor alpha subunit or αβγ complex. In some embodiments, the modified IL-2 polypeptide comprises an additional amino acid substitution that has an effect on binding to the IL-2 receptor beta subunit or By complex. In some embodiments, the modified IL-2 polypeptide comprises at least one additional amino acid substitution selected from Table 2. In some embodiments, the modified IL-2 polypeptide comprises at least one amino acid substitution at residue E15, N29, N30, T37, K48, V69, N71, N88, I89, or I92. In some embodiments, the modified IL-2 polypeptide comprises 1, 2, 3, or 4 natural amino acid substitutions at residues selected from E15, N29, N30, T37, K48, V69, N71, N88, I89, or I92. In some embodiments, the modified IL-2 polypeptide comprises 1 natural amino acid substitutions at residues selected from E15, N29, N30, T37, K48, V69, N71, N88, I89, or I92. In some embodiments, the modified IL-2 polypeptide comprises 2 In some embodiments, the modified IL-2 polypeptide comprises up to 2 natural amino acid substitutions at residues selected from E15, N29, N30, T37, K48, V69, N71, N88, I89, or I92. In some embodiments, the modified IL-2 polypeptide comprises up to 3 natural amino acid substitutions at residues selected from E15, N29, N30, T37, K48, V69, N71, N88, I89, or I92. In some embodiments, the additional amino acid substitution comprises E15A, E15G, or E15S. In some embodiments, the additional amino acid substitution comprises N29S. In some embodiments, the additional amino acid substitution comprises N30S. In some embodiments, the additional amino acid substitution comprises T37A or T37R. In some embodiments, the additional amino acid substitution comprises K48E. In some embodiments, the additional amino acid substitution comprises V69A. In some embodiments, the additional amino acid substitution comprises N71R. In some embodiments, the additional amino acid substitution comprises N88A, N88D, N88E, N88F, N88G, N88H, N88I, N88M, N88Q, N88R, N88S, N88T, N88V, or N88W. In some embodiments, the additional amino acid substitution comprises N88D. In some embodiments, the additional amino acid substitution comprises I89V. In some embodiments, the additional amino acid substitution comprises I92K or I92R.

In some embodiments, a modified IL-2 polypeptide provided herein comprises mutations at Y31, K35, Q74, and optionally C125S. In some embodiments, the modified IL-2 polypeptide does not comprise any additional mutations which substantially affect binding to the IL-2 receptor alpha subunit or αβγ complex. In some embodiments, the modified IL-2 polypeptide does not comprise an additional amino acid substitution that has an effect on binding to the IL-2 receptor beta subunit or By complex. In some embodiments, the modified IL-2 polypeptide does not comprise any additional natural amino acid substitutions selected from positions identified in Table 2. n some embodiments, the modified IL-2 polypeptide does not comprise any additional natural amino acid substitutions selected from positions identified in Table 3. In some embodiments, the modified IL-2 polypeptide does not comprise any additional amino acid substitutions selected from Table 2. In some embodiments, the modified IL-2 polypeptide does not comprise any additional amino acid substitutions selected from Table 3. In some embodiments, the modified IL-2 polypeptide does not comprise any additional natural amino acid substitutions at residues E15, N29, N30, T37, K48, V69, N71, N88, I89, or 192. In some embodiments, the modified IL-2 polypeptide does not comprise any additional amino acid substitutions at residues E15, N29, N30, T37, K48, V69, N71, N88, I89, or 192. In some embodiments, the modified IL-2 polypeptide does not have a V69 mutation. In some embodiments, the modified IL-2 polypeptide does not have a V69A mutation. In some embodiments, the modified IL-2 polypeptide does not have a K48 mutation. In some embodiments, the modified IL-2 polypeptide does not have a K48E mutation. In some embodiments, the modified IL-2 polypeptide does not comprise a mutation at V69 or K48. In some embodiments, the modified IL-2 polypeptide does not comprise a mutation at either of V69 or K48. In some embodiments, the modified IL-2 polypeptide does not comprise a V69A or K48E mutation. In some embodiments, the modified IL-2 polypeptide does not comprise either a V69A or K48E mutation.

In some embodiments, a modified IL-2 polypeptide provided herein comprises substitutions at Y31, K35, Q74, N88, and optionally C125S. In some embodiments, the modified IL-2 polypeptide does not comprise any additional substitutions which substantially affect binding to the IL-2 receptor alpha subunit or αβγ complex. In some embodiments, the modified IL-2 polypeptide does not comprise an additional amino acid substitution that has an effect on binding to the IL-2 receptor beta subunit or βγ complex In some embodiments, the modified IL-2 polypeptide does not comprise any additional natural amino acid substitutions selected from positions identified in Table 3. In some embodiments, the modified IL-2 polypeptide does not comprise any additional amino acid substitutions selected from Table 3. In some embodiments, the modified IL-2 polypeptide does not comprise any additional natural amino acid substitutions at residues E15, N29, N30, T37, K48, V69, N71, 189, or 192. In some embodiments, the modified IL-2 polypeptide does not comprise any additional amino acid substitutions at residues E15, N29, N30, T37, K48, V69, N71, 189, or 192. In some embodiments, the modified IL-2 polypeptide docs not have a V69 substitution. In some embodiments, the modified IL-2 polypeptide does not have a V69A substitution. In some embodiments, the modified IL-2 polypeptide does not have a K48 substitution. In some embodiments, the modified IL-2 polypeptide does not have a K48E substitution. In some embodiments, the modified IL-2 polypeptide does not comprise a substitution at V69 or K48. In some embodiments, the modified IL-2 polypeptide does not comprise a substitution at either of V69 or K48. In some embodiments, the modified IL-2 polypeptide does not comprise a V69A or K48E substitution. In some embodiments, the modified IL-2 polypeptide does not comprise either a V69A or K48E substitution.

In one aspect, disclosed herein is a modified IL-2 polypeptide comprising one or more unnatural amino acid substitutions (e.g., for a synthetic IL-2 polypeptide). In some embodiments, the modified IL-2 polypeptide comprises at least two unnatural amino acid substitutions. In some embodiments, the modified IL-2 polypeptide comprises at least one amino acid substitution at a residue selected from Y31, K35, and Q74, wherein residue position numbering of the modified IL-2 polypeptide is based on SEQ ID NO: 1 as a reference sequence.

In some embodiments, the IL-2 polypeptide can comprise a polymer (e.g., other than the linker) which disrupts binding between the modified IL-2 polypeptide and the IL-2 receptor beta subunit, or which otherwise biases the modified IL-2 polypeptide in favor of signaling through the alpha subunit. In some embodiments, the point of attachment of the polymer is selected such that interaction of the IL-2 polypeptide with an IL-2 receptor containing the IL-2R alpha receptor subunit is unaffected or only slightly reduced. In some embodiments, the point of attachment of the polymer is selected such that interaction of the IL-2 polypeptide with the IL-2 beta receptor subunit is substantially reduced. Examples of such residues are provided in US Publication No. US2020/0231644A1, which is hereby incorporated by reference as if set forth in its entirety. In some embodiments, the polymer is attached to a residue at position 8, 9, 11, 12, 15, 16, 18, 19, 20, 22, 23, 26, 81, 84, 87, 88, 91, 92, 94, 95, 116, 119, 120, 123, 125, 126, 127, 130, 131, 132, or 133 of the IL-2 polypeptide, wherein residue position numbering is based on SEQ ID NO: 1 as a reference sequence. In some embodiments, the polymer is attached to a residue at position 8, 9, 12, 15, 16, 19, 20, 22, 23, 26, 84, 88, 95, or 126 of the IL-2 polypeptide. In some embodiments, the polymer is attached to a residue at position 8, 9, or 16. In some embodiments, the polymer is attached to a residue at position 22, 26, 88, or 126 of the IL-2 polypeptide. In some embodiments, the polymer is attached to a residue at position 15, 20, 84, or 95 of the IL-2 polypeptide. In some embodiments, the polymer is attached to a residue at position 12, 19, or 23 of the IL-2 polypeptide. In some embodiments, the polymer is attached to a residue at position 22 or 26. In some embodiments, the polymer is attached to a residue at position 35 of the IL-2 polypeptide. In some embodiments, the polymer is attached at residue 88. In some embodiments, the polymer is attached at residue N88D. In some embodiments, the polymer attached at residue 88 is attached to an amino acid a modified aspartate residue, wherein the polymer attached to the residue has the structure 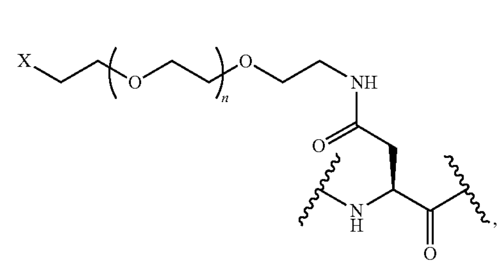 wherein n is an integer from 1-30, and wherein X is $NH_2$, $-OCH_3$, OH, $-NH(C{=}O)\ CH_3$, or a conjugation handle (e.g., azide). In some embodiments, n is an integer from 8-10. In some embodiments, X is —NH$_2$. When X is NH$_2$ and n is 9, the corresponding amino acid is optionally referred to herein as Dgp (D with a O-(2-aminoethyl)-O'-(2-aminoethyl) octaethylene glycol). For sequence identity purposes, it is intended herein that such an amino acid (which may also be referred to in a more general sense as s a "modified D," "D modified with a polymer," or similar language) would qualify as the base amino acid from which the final structure is derived (e.g., such a residue would qualify as a D for sequence identify purposes).

In some embodiments, the modified IL-2 polypeptide comprises a modification at the N-terminal residue. In some embodiments, the modified IL-2 polypeptide comprises a C125S mutation. In some embodiments, the modified IL-2 polypeptide comprises an A1 deletion. In some embodiments, the modification comprises attachment of the linker which attaches the IL-2 polypeptide to the polypeptide which selectively binds to TNFα.

In some embodiments, the modified IL-2 polypeptide comprises SEQ ID NO: 3. In some embodiments, the modified IL-2 polypeptide comprises SEQ ID NO: 3 with an A1 deletion.

In some embodiments, the modified IL-2 polypeptide comprises SEQ ID NO: 4. In some embodiments, the modified IL-2 polypeptide comprises an A1 deletion.

In some embodiments, the modified IL-2 polypeptide comprises SEQ ID NO: 5. In some embodiments, the modified IL-2 polypeptide comprises SEQ ID NO: 5 with an A1 deletion.

In some embodiments, the modified IL-2 polypeptide comprises SEQ ID NO: 6. In some embodiments, the modified IL-2 polypeptide comprises SEQ ID NO: 6 with an A1 deletion.

In some embodiments, the modified IL-2 polypeptide comprises SEQ ID NO: 7. In some embodiments, the modified IL-2 polypeptide comprises SEQ ID NO: 7 with an A1 deletion.

In some embodiments, the modified IL-2 polypeptide comprises SEQ ID NO: 8. In some embodiments, the modified IL-2 polypeptide comprises SEQ ID NO: 8 with an A1 deletion.

In some embodiments, a modified IL-2 polypeptide provided herein comprises an amino acid sequence of any one of SEQ ID NOs: 3-8 provided in Table 4. In some embodiments, the modified IL-2 polypeptide comprises an amino acid sequence at least 80%, 85%, 90%, 95%, 99%, or 100% identical to the sequence of any one of SEQ ID NOs: 3-8. In some embodiments, the modified IL-2 polypeptide comprises an amino acid sequence at least 80%, 85%, 90%, 95%, 99%, or 100% identical to the sequence of SEQ ID NO: 3. In some embodiments, the modified IL-2 polypeptide comprises an amino acid sequence at least 80%, 85%, 90%, 95%, 99%, or 100% identical to the sequence of SEQ ID NO: 4. In some embodiments, the modified IL-2 polypeptide comprises an amino acid sequence at least 80%, 85%, 90%, 95%, 99%, or 100% identical to the sequence of SEQ ID NO: 5. In some embodiments, the modified IL-2 polypeptide comprises an amino acid sequence at least 80%, 85%, 90%, 95%, 99%, or 100% identical to the sequence of SEQ ID NO: 6. In some embodiments, the modified IL-2 polypeptide comprises an amino acid sequence at least 80%, 85%, 90%, 95%, 99%, or 100% identical to the sequence of SEQ ID NO: 7. In some embodiments, the modified IL-2 polypeptide comprises an amino acid sequence at least 80%, 85%, 90%, 95%, 99%, or 100% identical to the sequence of SEQ ID NO: 8.

In some embodiments, a modified IL-2 polypeptide described herein comprises at least about 80%, at least about 85%, at least about 90%, at least about 95%, at least about 96%, at least about 97%, at least about 98%, at least about 99%, or 100% sequence identity to SEQ ID NO: 3. In some embodiments, the sequence identity is measured by protein-protein BLAST algorithm using parameters of Matrix BLOSUM62, Gap Costs Existence: 11, Extension: 1, and Compositional Adjustments Conditional Compositional Score Matrix Adjustment.

In some embodiments, the chemically synthesized IL-2 polypeptide comprises a conjugation handle attached to one or more residues to facilitate attachment of the linker to the polypeptide which selectively binds to TNFα. The conjugation handle may be any such conjugation handle provided herein and may be attached at any residue to which the linker may be attached. In some embodiments, the conjugation handle comprises an azide or an alkyne. Alternatively, in some embodiments, the conjugation handle is incorporated into an unnatural or modified natural amino acid of a recombinant IL-2 polypeptide. Recombinant IL-2 polypeptides with unnatural amino acids can be made using methods as described in, for example, Patent Cooperation Treaty Publication Nos. WO2016115168, WO2002085923, WO2005019415, and WO2005003294.

Biological Activity

In some preferred embodiments, a modified IL-2 polypeptide described herein is capable of expanding a regulatory T-cell (T$_{reg}$) cell population. In some embodiments, a modified IL-2 polypeptide described herein spares expansion of effector T-cells (T$_{eff}$).

In one aspect, described herein is a modified IL-2 polypeptide that exhibits a greater affinity for IL-2 receptor α subunit than an IL-2 polypeptide of SEQ ID NO: 1 and/or SEQ ID NO: 2. In some embodiments, the affinity to IL-2 receptor α subunit is measured by dissociation constant (K$_d$). As used herein, the phrase "the K$_d$ of the modified IL-2 polypeptide/IL-2 receptor a subunit" means the dissociation constant of the binding interaction of the modified IL-2 polypeptide and CD25.

In some embodiments, the K$_d$ of the modified IL-2 polypeptide/IL-2 receptor α subunit is less than 10 nM. In some embodiments the K$_d$ of the modified IL-2 polypeptide/IL-2 receptor a subunit is less than 10 nM, less than 7.5 nM, less than 5 nM, less than 4 nM, or less than 3 nM. In some embodiments, the K$_d$ of the modified IL-2 polypeptide/IL-2 receptor α subunit between about 1 nM and 0.1 nM. In some embodiments, the K$_d$ of the modified IL-2 polypeptide/IL-2 receptor α subunit between about 10 nM and about 0.1 nM. In some embodiments, the K$_d$ of the modified IL-2 polypeptide/IL-2 receptor α subunit between about 10 nM and about 1 nM. In some embodiments, the K$_d$ of the modified IL-2 polypeptide/IL-2 receptor α subunit between about 7.5 nM and about 0.1 nM. In some embodiments, the K$_d$ of the modified IL-2 polypeptide/IL-2 receptor α subunit between about 7.5 nM and about 1 nM. In some embodiments, the K$_d$ of the modified IL-2 polypeptide/IL-2 receptor α subunit between about 5 nM and about 0.1 nM. In some embodiments, the K$_d$ of the modified IL-2 polypeptide/IL-2 receptor α subunit between about 1 nM and about 1 nM. In some embodiments, the K$_d$ is measured by surface plasmon resonance.

In some embodiments, the modified IL-2 polypeptide that exhibits at least about a 10%, 50%, 100%, 250%, or 500% greater affinity for IL-2 receptor α subunit than an IL-2 polypeptide of SEQ ID NO: 1 and/or SEQ ID NO: 2. In some embodiments, the modified IL-2 polypeptide exhibits at most about a 500%, 750%, or 1000% greater affinity for IL-2 receptor α subunit than an IL-2 polypeptide of SEQ ID NO: 1 and/or SEQ ID NO: 2.

In some embodiments, the modified IL-2 polypeptide exhibits about 1.5-fold to about 10-fold greater affinity for IL-2 receptor α subunit than an IL-2 polypeptide of SEQ ID NO: 1 and/or SEQ ID NO: 2.

In some embodiments, the modified IL-2 polypeptide exhibits substantially the same binding affinity for the IL-2Rα as compared to an IL-2 polypeptide of SEQ ID NO: 1 and/or SEQ ID NO: 2. In some embodiments, the modified IL-2 polypeptide exhibits a $K_d$ with IL-2Rα that is within about 2-fold, about 4-fold, about 6-fold, about 8-fold, or about 10-fold of the $K_d$ between an IL-2 polypeptide of SEQ ID NO: 1 and/or SEQ ID NO: 2 and IL-2Rα.

In some embodiments, the modified IL-2 polypeptide exhibits reduced affinity for the IL-2 receptor β subunit (IL-2Rβ) as compared to an IL-2 polypeptide of SEQ ID NO: 1 and/or SEQ ID NO: 2. In some embodiments, the modified IL-2 polypeptide exhibits at least about 10-fold, at least about 25-fold, at least about 50-fold, at least about 100-fold, or at least about 500-fold fold lower affinity for the IL-2Rβ. In some embodiments, the modified IL-2 polypeptide exhibits at least about 100-fold lower affinity for IL-2Rβ. In some embodiments, the modified IL-2 polypeptide exhibits substantially no affinity for IL-2Rβ. In some embodiments, the affinity is measured as the dissociation constant $K_d$ (e.g., a lower affinity correlating with a higher dissociation constant).

In some embodiments, the modified IL-2 polypeptide exhibits a binding affinity for IL-2Rβ which is at least 500 nM, at least 1000 nM, at least 5000 nM, at least 10000 nM, at least 50000 nM, or at least 100000 nM.

In some embodiments, the modified IL-2 polypeptide exhibits an affinity for IL-2Rα which is greater than for IL-2Rb (e.g., a $k_d$ for the modified IL-2 with IL-2Rα is lower than a $k_d$ for the modified IL-2 with IL-2Rβ). In some embodiments, the modified IL-2 polypeptide exhibits an affinity for IL-2Rα which is at least about 30-fold greater, at least about 50-fold greater, at least about 75-fold greater, at least about 100-fold greater, at least about 500-fold greater, or at least about 1000-fold greater than for IL-2Rβ. In some embodiments, the modified IL-2 polypeptide exhibits an affinity for IL-2Rα which is at least about 100-fold greater than for IL-2Rβ. In some embodiments, the modified IL-2 polypeptide exhibits an affinity for IL-2Rα which is at least about 1000-fold greater than for IL-2Rβ.

In some embodiments, a modified IL-2 polypeptide has a half maximal effective concentration ($EC_{50}$) for activation of $T_{reg}$ cells that is at most moderately reduced compared to an IL-2 polypeptide of SEQ ID NO: 1 and/or SEQ ID NO: 2. In some embodiments, activation of $T_{reg}$ cells is measured by assessing change in STAT5 phosphorylation in a population of T cells when in contact with the modified IL-2 polypeptide. In some embodiments, a $T_{reg}$ cell is identified by being CD4$^+$ CD25+, and FoxP3$^+$. In some embodiments, a $T_{reg}$ cell is identified by also showing elevated expression of CD25 (CD25$^{Hi}$). In some embodiments, the modified IL-2 polypeptide has an $EC_{50}$ for activation of $T_{reg}$ cells of at most about 100 nM, at most about 75 nM, at most about 50 nM, at most about 40 nM, at most about 35 nM, at most about 30 nM, or at most about 25 nM. In some embodiments, the modified IL-2 polypeptide has an $EC_{50}$ for activation of $T_{reg}$ cells of at most about 50 nM, at most about 40 nM, at most about 35 nM, at most about 30 nM, or at most about 25 nM, at most about 20 nM, at most about 15 nM, at most about 10 nM, or at most about 5 nM. In some embodiments, the modified IL-2 polypeptide has an $EC_{50}$ for activation of $T_{reg}$ cells of at most about 100 nM. In some embodiments, the modified IL-2 polypeptide has an $EC_{50}$ for activation of $T_{reg}$ cells of at most about 50 nM. In some embodiments, the modified IL-2 polypeptide has an $EC_{50}$ for activation of $T_{reg}$ cells of at most about 25 nM. In some embodiments, the modified IL-2 polypeptide has an $EC_{50}$ for activation of $T_{reg}$ cells of from about 0.1 nM to about 100 nM, from about 1 nM to about 100 nM, from about 0.1 nM to about 50 nM, from about 1 nM to about 50 nM, from about 0.1 nM to about 25 nM, from about 1 nM to about 25 nM, from about 0.1 nM to about 10 nM, or from about 1 nM to about 10 nM.

In some embodiments, the modified IL-2 polypeptide has an $EC_{50}$ for activation of $T_{reg}$ cells that is at most 2-fold, at most 5-fold, at most 10-fold, at most 20-fold, at most 50-fold, at most 100-fold, at most 200-fold, at most 500-fold, or at most 1000-fold greater compared to an IL-2 polypeptide of SEQ ID NO: 1 and/or SEQ ID NO: 2. In some embodiments, the modified IL-2 polypeptide has an $EC_{50}$ for activation of $T_{reg}$ cells that is at most 2-fold greater. In some embodiments, the modified IL-2 polypeptide has an $EC_{50}$ for activation of $T_{reg}$ cells that is at most 5-fold greater. In some embodiments, the modified IL-2 polypeptide has an $EC_{50}$ for activation of $T_{reg}$ cells that is at most 10-fold greater. In some embodiments, the modified IL-2 polypeptide has an $EC_{50}$ for activation of $T_{reg}$ cells that is at most 50-fold greater. In some embodiments, the modified IL-2 polypeptide has an $EC_{50}$ for activation of $T_{reg}$ cells that is at most 100-fold greater. In some embodiments, the modified IL-2 polypeptide has an $EC_{50}$ for activation of $T_{reg}$ cells that is at most 200-fold greater. In some embodiments, the modified IL-2 polypeptide has an $EC_{50}$ for activation of $T_{reg}$ cells that is at most 500-fold greater. In some embodiments, the modified IL-2 polypeptide has an $EC_{50}$ for activation of $T_{reg}$ cells that is at most 1000-fold greater.

In some embodiments, a modified IL-2 polypeptide has a half maximal effective concentration ($EC_{50}$) for activation of $T_{eff}$ cells that is substantially greater compared to an IL-2 polypeptide of SEQ ID NO: 1 and/or SEQ ID NO: 2. In some embodiments, the $T_{eff}$ cell is 1, 2, or 3 of a CD8 $T_{eff}$ cell (e.g., CD8+), a Naïve CD8 cell (e.g., CD8$^+$, CD45RA$^+$), or a CD4con cell (e.g., CD4$^+$, FoxP3$^-$), or any combination thereof. In some embodiments, activation of cells is measured by assessing change in STAT5 phosphorylation in a population of T cells when in contact with the modified IL-2 polypeptide. In some embodiments, the modified IL-2 polypeptide has an $EC_{50}$ for activation of $T_{eff}$ cells of at least about 10 nM, at least about 50 nM, at least about 100 nM, at least about 500 nM, at least about 1000 nM, at least about 2000 nM, at least about 3000 nM, at least about 4000 nM, or at least about 5000 nM. In some embodiments, the modified IL-2 polypeptide has an $EC_{50}$ for activation of $T_{eff}$ cells of at least about 100 nM. In some embodiments, the modified IL-2 polypeptide has an $EC_{50}$ for activation of $T_{eff}$ cells of at least about 500 nM. In some embodiments, the modified IL-2 polypeptide has an $EC_{50}$ for activation of $T_{eff}$ cells of at least about 1000 nM. In some embodiments, the modified IL-2 polypeptide has an $EC_{50}$ for activation of $T_{eff}$ cells of at least about 5000 nM. In some embodiments, the modified IL-2 polypeptide has an $EC_{50}$ for activation of $T_{eff}$ cells of at least 10-fold, at least 20-fold, at least 50-fold, at least 100-fold, at least 500-fold, or at least 1000-fold greater compared to an IL-2 polypeptide of SEQ ID NO: 1 and/or SEQ ID NO: 2. In some embodiments, the modified IL-2 polypeptide has an $EC_{50}$ for activation of $T_{eff}$ cells of at least 10-fold greater. In some embodiments, the modified IL-2 polypeptide has an $EC_{50}$ for activation of $T_{eff}$ cells of at least 50-fold greater. In some embodiments, the modified IL-2 polypeptide has an $EC_{50}$ for activation of $T_{eff}$ cells of at least 100-fold greater. In some embodiments, the modified IL-2 polypeptide has an $EC_{50}$ for activation of $T_{eff}$ cells of at least 500-fold greater. In some embodiments, the modified IL-2 polypeptide has an $EC_{50}$ for activation of $T_{eff}$ cells of at least 1000-fold greater.

In some embodiments, the modified IL-2 polypeptide exhibits a substantially greater ability to activate $T_{reg}$ cells compared to $T_{eff}$ cells. In some embodiments, a ratio of $EC_{50}$ for activation of a $T_{eff}$ cell type over $EC_{50}$ for activation of a $T_{reg}$ cell type is at least 10, at least 20, at least 50, at least 100, at least 150, or at least 200. In some embodiments, a ratio of $EC_{50}$ for activation of a $T_{eff}$ cell type over $EC_{50}$ for activation of a $T_{reg}$ cell type is at least 100. In some embodiments, a ratio of $EC_{50}$ for activation of a $T_{eff}$ cell type over $EC_{50}$ for activation of a $T_{reg}$ cell type is at least 200. In some embodiments, a ratio of $EC_{50}$ for activation of a $T_{eff}$ cell type over $EC_{50}$ for activation of a $T_{reg}$ cell type is at least 300. In some embodiments, a ratio of $EC_{50}$ for activation of a $T_{eff}$ cell type over $EC_{50}$ for activation of a $T_{reg}$ cell type is at least 500. In some embodiments, a ratio of $EC_{50}$ for activation of a $T_{eff}$ cell type over $EC_{50}$ for activation of a $T_{reg}$ cell type is at least 1000.

In some embodiments, a modified IL-2 polypeptide described herein expands a cell population of regulatory T cells ($T_{reg}$ cells). In some embodiments, the modified IL-2 polypeptide expands a cell population of $T_{reg}$ cells by at least 1%, at least 2%, at least 5%, at least 10%, at least 15%, at least 20%, at least 30%, at least 40%, at least 50%, at least 100%, or at least 200% when the modified IL-2 polypeptide is in contact with the population. In some embodiments, the modified IL-2 polypeptide expands a cell population of $T_{reg}$ cells by at least 20% when the modified IL-2 polypeptide is in contact with the population. In some embodiments, the modified IL-2 polypeptide expands a cell population of $T_{reg}$ cells by at least 30% when the modified IL-2 polypeptide is in contact with the population. In some embodiments, the modified IL-2 polypeptide expands a cell population of $T_{reg}$ cells by at least 40% when the modified IL-2 polypeptide is in contact with the population. In some embodiments, the modified IL-2 polypeptide expands a cell population of $T_{reg}$ cells by at least 50% when the modified IL-2 polypeptide is in contact with the population. In some embodiments, the modified IL-2 polypeptide expands a cell population of $T_{reg}$ cells by at least 100% when the modified IL-2 polypeptide is in contact with the population. In some embodiments, the modified IL-2 polypeptide expands a cell population of $T_{reg}$ cells by at least 200% when the modified IL-2 polypeptide is in contact with the population. In some embodiments, the modified IL-2 polypeptide expands a cell population of $T_{reg}$ cells by at least 2-fold, at least 3-fold, at least 5-fold, at least 7-fold, at least 10-fold, or at least 15-fold when the modified IL-2 polypeptide is in contact with the cell population. In some embodiments, the expansion of $T_{reg}$ cells is measured compared to a sample or subject not treated by an Il-2 polypeptide. In some embodiments, the expansion of $T_{reg}$ cells is measured compared to a sample or subject treated with an IL-2 polypeptide of SEQ ID NO: 1 and/or SEQ ID NO: 2. In some embodiments, the expansion of $T_{reg}$ cells is measured compared to a sample or subject treated with an IL-2 polypeptide of SEQ ID NO: 1 and/or SEQ ID NO: 2 at the same dose of IL-2 polypeptide as the modified IL-2 polypeptide.

In some embodiments, a modified IL-2 polypeptide has a half maximal effective concentration ($EC_{50}$) for activation of $T_{reg}$ cells that is comparable to an IL-2 polypeptide of SEQ ID NO: 1 and/or SEQ ID NO: 2. In some embodiments, the modified IL-2 polypeptide has an $EC_{50}$ for activation of $T_{reg}$ cells of at most about 0.01 nM, at most about 0.05 nM, at most about 0.1 nM, at most about 0.5 nM, at most about 1 nM, at most about 5 nM, at most about 10 nM, at most about 50 nM, or at most about 100 nM. In some embodiments, the modified IL-2 polypeptide has an $EC_{50}$ for activation of $T_{reg}$ cells of at most about 0.01 nM. In some embodiments, the modified IL-2 polypeptide has an $EC_{50}$ for activation of $T_{reg}$ cells of at most about 0.05 nM. In some embodiments, the modified IL-2 polypeptide has an $EC_{50}$ for activation of $T_{reg}$ cells of at most about 0.1 nM. In some embodiments, the modified IL-2 polypeptide has an $EC_{50}$ for activation of $T_{reg}$ cells of at most about 0.5 nM. In some embodiments, the modified IL-2 polypeptide has an $EC_{50}$ for activation of $T_{reg}$ cells of at most about 1 nM. In some embodiments, the modified IL-2 polypeptide has an $EC_{50}$ for activation of $T_{reg}$ cells from about 0.01 nM to about 100 nM, about 0.01 nM to about 50 nM, 0.01 nM to about 10 nM, 0.01 nM to about 5 nM, 0.01 nM to about 1 nM, about 0.01 nM to about 0.5 nM, or about 0.01 nM to about 0.1 nM. In some embodiments, the modified IL-2 polypeptide has an $EC_{50}$ for activation of $T_{reg}$ cells from about 0.05 nM to about 100 nM, about 0.05 nM to about 50 nM, 0.05 nM to about 10 nM, 0.05 nM to about 5 nM, 0.05 nM to about 1 nM, about 0.05 nM to about 0.5 nM, or about 0.05 nM to about 0.1 nM.

In some embodiments, the modified IL-2 polypeptide has an $EC_{50}$ for activation of $T_{reg}$ cells that is at most 2-fold, at most 5-fold, at most 10-fold, at most 20-fold, at most 50-fold, at most 100-fold, at most 200-fold, at most 500-fold, or at most 1000-fold greater compared to an IL-2 polypeptide of SEQ ID NO: 1 and/or SEQ ID NO: 2. In some embodiments, the modified IL-2 polypeptide has an $EC_{50}$ for activation of $T_{reg}$ cells that is at most 2-fold greater. In some embodiments, the modified IL-2 polypeptide has an $EC_{50}$ for activation of $T_{reg}$ cells that is at most 5-fold greater. In some embodiments, the modified IL-2 polypeptide has an $EC_{50}$ for activation of $T_{reg}$ cells that is at most 10-fold greater. In some embodiments, the modified IL-2 polypeptide has an $EC_{50}$ for activation of $T_{reg}$ cells that is at most 50-fold greater. In some embodiments, the modified IL-2 polypeptide has an $EC_{50}$ for activation of $T_{reg}$ cells that is at most 100-fold greater. In some embodiments, the modified IL-2 polypeptide has an $EC_{50}$ for activation of $T_{reg}$ cells that is at most 200-fold greater. In some embodiments, the modified IL-2 polypeptide has an $EC_{50}$ for activation of $T_{reg}$ cells that is at most 500-fold greater. In some embodiments, the modified IL-2 polypeptide has an $EC_{50}$ for activation of $T_{reg}$ cells that is at most 1000-fold greater.

In some embodiments, a modified IL-2 polypeptide provided herein spares expansion of a population of effector T-cells ($T_{eff}$ cells). In some embodiments, the modified IL-2 polypeptide expands a cell population of $T_{eff}$ cells by at most 1%, at most 2%, at most 5%, at most 10%, at most 15%, at most 20%, at most 30%, at most 40%, at most 50%, at most 100%, or at most 200% when the modified IL-2 polypeptide is in contact with the population. In some embodiments, the modified IL-2 polypeptide expands a cell population of $T_{eff}$ cells by at most 1%. In some embodiments, the modified IL-2 polypeptide expands a cell population of $T_{eff}$ cells by at most 2%. In some embodiments, the modified IL-2 polypeptide expands a cell population of $T_{eff}$ cells by at most 5%. In some embodiments, the modified IL-2 polypeptide expands a cell population of $T_{eff}$ cells by at most 10%. In some embodiments, the modified IL-2 polypeptide expands a cell population of $T_{eff}$ cells by at most 15%. In some embodiments, the modified IL-2 polypeptide expands a cell population of $T_{eff}$ cells by at most 20%. In some embodiments, the expansion of $T_{eff}$ cells is measured compared to a sample or subject not treated by an IL-2 polypeptide. In some embodiments, the expansion of $T_{eff}$ cells is measured compared to a sample or subject treated with an IL-2 polypeptide of SEQ ID NO: 1 and/or SEQ ID NO: 2. In some embodiments, the expansion of $T_{eff}$ cells is measured compared to a sample or subject treated with an IL-2 polypeptide of SEQ ID NO: 1 and/or SEQ ID NO: 2 at the same dose of IL-2 polypeptide as the modified IL-2 polypeptide.

In some embodiments, a modified IL-2 polypeptide has a half maximal effective concentration ($EC_{50}$) for activation of $T_{eff}$ cells that is substantially greater compared to an IL-2 polypeptide of SEQ ID NO: 1 and/or SEQ ID NO: 2. In some embodiments, the modified IL-2 polypeptide has an $EC_{50}$ for activation of $T_{eff}$ cells of at least about 10 nM, at least about 50 nM, at least about 100 nM, at least about 500 nM, at least about 1000 nM, at least about 5000 nM, at least about 10000 nM, at least about 50000 nM, or at least about 100000 nM. In some embodiments, the modified IL-2 polypeptide has an $EC_{50}$ for activation of $T_{eff}$ cells of at least about 100000 nM. In some embodiments, the modified IL-2 polypeptide has an $EC_{50}$ for activation of $T_{eff}$ cells of at least about 50000 nM. In some embodiments, the modified IL-2 polypeptide has an $EC_{50}$ for activation of eff cells of at least about 10000 nM. In some embodiments, the modified IL-2 polypeptide has an $EC_{50}$ for activation of $T_{eff}$ cells of at least about 5000 nM. In some embodiments, the modified IL-2 polypeptide has an $EC_{50}$ for activation of $T_{eff}$ cells of at least about 1000 nM. In some embodiments, the modified IL-2 polypeptide has an $EC_{50}$ for activation of $T_{eff}$ cells of at least 10-fold, at least 20-fold, at least 50-fold, at least 100-fold, at least 500-fold, or at least 1000-fold greater compared to an IL-2 polypeptide of SEQ ID NO: 1 and/or SEQ ID NO: 2. In some embodiments, the modified IL-2 polypeptide has an $EC_{50}$ for activation of $T_{eff}$ cells of at least 10-fold greater. In some embodiments, the modified IL-2 polypeptide has an $EC_{50}$ for activation of $T_{eff}$ cells of at least 50-fold greater. In some embodiments, the modified IL-2 polypeptide has an $EC_{50}$ for activation of $T_{eff}$ cells of at least 100-fold greater. In some embodiments, the modified IL-2 polypeptide has an $EC_{50}$ for activation of $T_{eff}$ cells of at least 500-fold greater. In some embodiments, the modified IL-2 polypeptide has an $EC_{50}$ for activation of $T_{eff}$ cells of at least 1000-fold greater. In some embodiments, the modified IL-2 polypeptide has an $EC_{50}$ for activation of $T_{eff}$ cells of at least 10000-fold greater. In some embodiments, the modified IL-2 polypeptide has an $EC_{50}$ for activation of $T_{eff}$ cells of at least 100000-fold greater.

In some embodiments, a cell population expanded by a modified IL-2 polypeptide provided herein is an in vitro cell population, an in vivo cell population, or an ex vivo cell population. In some embodiments, the cell population is an in vitro cell population. In some embodiments, the cell population is an in vivo cell population. In some embodiments, the cell population is an ex vivo cell population. The cell population may be a population of CD4+ helper cells, CD8+ central memory cells, CD8+ effector memory cells, naïve CD8+ cells, Natural Killer (NK) cells, Natural killer T (NKT) cells, or a combination thereof.

In some embodiments, a modified IL-2 described herein polypeptide expands a cell population of regulatory T cells ($T_{reg}$ cells). In some embodiments, the modified IL-2 polypeptide expands a cell population of $T_{reg}$ cells by at least 1%, at least 2%, at least 5%, at least 10%, at least 15%, at least 20%, at least 30%, at least 40%, at least 50%, at least 100%, or at least 200% when the modified IL-2 polypeptide is in contact with the population. In some embodiments, the modified IL-2 polypeptide expands a cell population of $T_{reg}$ cells by at least 20% when the modified IL-2 polypeptide is in contact with the population. In some embodiments, the modified IL-2 polypeptide expands a cell population of $T_{reg}$ cells by at least 30% when the modified IL-2 polypeptide is in contact with the population. In some embodiments, the modified IL-2 polypeptide expands a cell population of $T_{reg}$ cells by at least 40% when the modified IL-2 polypeptide is in contact with the population. In some embodiments, the modified IL-2 polypeptide expands a cell population of $T_{reg}$ cells by at least 50% when the modified IL-2 polypeptide is in contact with the population. In some embodiments, the modified IL-2 polypeptide expands a cell population of $T_{reg}$ cells by at least 100% when the modified IL-2 polypeptide is in contact with the population. In some embodiments, the modified IL-2 polypeptide expands a cell population of $T_{reg}$ cells by at least 200% when the modified IL-2 polypeptide is in contact with the population.

Biological Activity of Polypeptide Which Selectively Binds TNFα

In some embodiments, an immunoconjugate composition provided herein (e.g., a polypeptide which binds to TNFα (e.g., an anti-TNFα antibody) attached to an IL-2 polypeptide through a linker) maintains binding affinity associated with at least one of the components after formation of the linkage between the two groups. For example, in an immunoconjugate composition comprising an anti-TNFα antibody or antigen binding fragment linked to an IL-2 polypeptide, in some embodiments the anti-TNFα antibody or antigen binding fragment thereof retains binding to one or more Fc receptors. In some embodiments, the composition displays binding to one or more Fc receptors which is reduced by no more than about 5-fold, no more than about 10-fold, no more than about 15-fold, or no more than about 20-fold compared to the unconjugated antibody. In some embodiments, the one or more Fc receptors is the FcRn receptor, CD16a, the FcγRI receptor (CD64), the FcγRIIa receptor (CD32a), the FcγRIIβ receptor (CD32β), or any combination thereof. In some embodiments, binding of the composition to each of the FcRn receptor, CD16a, the FcγRI receptor (CD64), the FcγRIIa receptor (CD32α), and the FcγRIIβ receptor (CD32β) is reduced by no more than about 10-fold compared to the unconjugated antibody.

In some embodiments, binding of the polypeptide which binds to TNFα (e.g., the antibody) to TNFα is substantially unaffected by the conjugation with the IL-2 polypeptide. In some embodiments, the binding of the polypeptide to TNFα is reduced by no more than about 5% compared to the unconjugated polypeptide.

Synthetic IL-2

In some instances, the modified IL-2 polypeptides described herein may be recombinant. The modified IL-2 polypeptides described herein may also be synthesized chemically rather than expressed as recombinant polypeptides. Synthetic IL-2 polypeptides have been described, at least in PCT Publication No WO2021140416A2, US Patent Application Publication No US20190023760A1, and Asahina et al., *Angew. Chem. Int. Ed.* 2015, 54, 8226-8230, each of which is incorporated by reference as if set forth herein in its entirety. It is contemplated that a synthetic version of any modified IL-2 polypeptide provided herein can be prepared (e.g., a synthetic version of any recombinant IL-2 polypeptide provided herein can be prepared in a synthetic version).

The modified IL-2 polypeptides can be made by synthesizing one or more fragments of the full-length modified IL-2 polypeptides, ligating the fragments together, and folding the ligated full-length polypeptide.

In some embodiments, a modified IL-2 polypeptide provided herein is synthetic. In some embodiments, the modified IL-2 polypeptide comprises a homoserine (Hse) residue located in any one of amino acid residues 35-45. In some embodiments, the modified IL-2 polypeptide comprises a Hse residue located in any one of amino acid residues 61-81. In some embodiments, the modified IL-2 polypeptide comprises a Hse residue located in any one of amino acid residues 94-114. In some embodiments, the modified IL-2 polypeptide comprises 1, 2, 3, or more Hse residues. In some embodiments, the modified IL-2 polypeptide comprises Hse41, Hse71, Hse104, or a combination thereof. In some embodiments, the modified IL-2 polypeptide comprises Hse41, Hse71, and Hse104. In some embodiments, the modified IL-2 polypeptide comprises at least two amino acid substitutions, wherein the at least two amino acid substitutions are selected from (a) a homoserine (Hse) residue located in any one of amino acid residues 35-45; (b) a homoserine residue located in any one of amino acid residues 61-81; and (c) a homoserine residue located in any one of amino acid residues 94-114. In some embodiments, the modified IL-2 polypeptide comprises Hse41 and Hse71. In some embodiments, the modified IL-2 polypeptide comprises Hse41 and Hse104. In some embodiments, the modified IL-2 polypeptide comprises Hse71 and Hse104. In some embodiments, the modified IL-2 polypeptide comprises Hse41. In some embodiments, the modified IL-2 polypeptide comprises Hse71. In some embodiments, the modified IL-2 polypeptide comprises Hse104. In some embodiments, the modified IL-2 polypeptide comprises 1, 2, 3, or more norleucine (Nle) residues. In some embodiments, the modified IL-2 polypeptide comprises a Nle residue located in any one of residues 18-28. In some embodiments, the modified IL-2 polypeptide comprises one or more Nle residues located in any one of amino acid residues 34-50. In some embodiments, the modified IL-2 polypeptide comprises a Nle residue located in any one of amino acid residues 20-60. In some embodiments, the modified IL-2 polypeptide comprises three Nle substitutions. In some embodiments, the modified IL-2 polypeptide comprises Nle23, Nle39, and Nle46.

Polymers

In some embodiments, a herein described modified IL-2 polypeptide comprises one or more polymers covalently attached thereon. In some embodiments, the described modified IL-2 polypeptide comprises 1, 2, 3, 4, 5, 6, 7, 8, 9, 10, or more polymers covalently attached to the modified IL-2 polypeptide. In some embodiments, the described modified IL-2 polypeptide comprises a first polymer. In some embodiments, the first polymer comprises at least a portion of the linker which attached the IL-2 polypeptide to the polypeptide which selectively binds to TNFα.

In some embodiments, the first polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof. In some embodiments, the water-soluble polymer is poly(alkylene oxide). In some embodiments, the water-soluble polymer is polysaccharide. In some embodiments, the water-soluble polymer is poly(ethylene oxide).

In some embodiments, a modified IL-2 polypeptide described herein comprises a first polymer covalently attached to the N-terminus of the IL-2 polypeptide. In some embodiments, the modified IL-2 polypeptide comprises a second polymer covalently attached thereto. In some embodiments, the modified IL-2 polypeptide comprises a second and a third polymer covalently attached thereto.

In some embodiments, the attached polymer such as the first polymer has a weight average molecular weight of about 120 Daltons to about 1,000 Daltons. In some embodiments, the polymer has a weight average molecular weight of about 120 Daltons to about 250 Daltons, about 120 Daltons to about 300 Daltons, about 120 Daltons to about 400 Daltons, about 120 Daltons to about 500 Daltons, about 120 Daltons to about 1,000 Daltons, about 250 Daltons to about 300 Daltons, about 250 Daltons to about 400 Daltons, about 250 Daltons to about 500 Daltons, about 250 Daltons to about 1,000 Daltons, about 300 Daltons to about 400 Daltons, about 300 Daltons to about 500 Daltons, about 300 Daltons to about 1,000 Daltons, about 400 Daltons to about 500 Daltons, about 400 Daltons to about 1,000 Daltons, or about 500 Daltons to about 1,000 Daltons. In some embodiments, the polymer has a weight average molecular weight of about 120 Daltons, about 250 Daltons, about 300 Daltons, about 400 Daltons, about 500 Daltons, or about 1,000 Daltons. In some embodiments, the polymer has a weight average molecular weight of at least about 120 Daltons, about 250 Daltons, about 300 Daltons, about 400 Daltons, or about 500 Daltons. In some embodiments, the polymer has a weight average molecular weight of at most about 250 Daltons, about 300 Daltons, about 400 Daltons, about 500 Daltons, or about 1,000 Daltons.

In some embodiments, the attached polymer such as the first polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof. In some embodiments, the water-soluble polymer is poly(alkylene oxide) such as polyethylene glycol (e.g., polyethylene oxide). In some embodiments, the water-soluble polymer is polyethylene glycol. In some embodiments, the water-soluble polymer comprises modified poly(alkylene oxide). In some embodiments, the modified poly(alkylene oxide) comprises one or more linker groups. In some embodiments, the one or more linker groups comprise bifunctional linkers such as an amide group, an ester group, an ether group, a thioether group, a carbonyl group and alike. In some embodiments, the one or more linker groups comprise an amide linker group. In some embodiments, the modified poly(alkylene oxide) comprises one or more spacer groups. In some embodiments, the spacer groups comprise a substituted or unsubstituted $C_1$-$C_6$ alkylene group. In some embodiments, the spacer groups comprise -$CH_2$—, —$CH_2CH_2$—, or —$CH_2CH_2CH_2$—. In some embodiments, the linker group is the product of a biorthogonal reaction (e.g., biocompatible and selective reactions). In some embodiments, the bioorthogonal reaction is a Cu(I)-catalyzed or "copper-free" alkyne-azide triazole-forming reaction, the Staudinger ligation, inverse-electron-demand Diels-Alder (IEDDA) reaction, "photoclick" chemistry, or a metal-mediated process such as olefin metathesis and Suzuki-Miyaura or Sonogashira cross-coupling. In some embodiments, the first polymer is attached to the IL-2 polypeptide via click chemistry. In some embodiments, the first polymer comprises at least a portion of the linker which attaches the IL-2 polypeptide to the polypeptide which selectively binds to TNFα.

In some embodiments, a modified IL-2 polypeptide provided herein comprises a reaction group that facilitates the conjugation of the modified IL-2 polypeptide with a derivatized molecule or moiety such as an antibody and a polymer. In some embodiments, the reaction group comprises one or more of: carboxylic acid derived active esters, mixed anhydrides, acyl halides, acyl azides, alkyl halides, N-maleimides, imino esters, isocyanates, and isothiocyanates. In some embodiments, the reaction group comprises azides. In some embodiments, the reaction group forms a part of the linker which attaches the IL-2 polypeptide to the polypeptide which selectively binds to TNFα.

In some embodiments, a modified IL-2 polypeptide provided herein comprises a chemical reagent covalently attached to a residue. In some embodiments, the chemical reagent comprises a bioorthogonal reagent. In some embodiments, the chemical reagent comprises an azide. In some embodiments, the chemical reagent comprises an alkyne.

In some embodiments, the water-soluble polymer comprises from 1 to 10 polyethylene glycol chains. In some embodiments, the modified IL-2 polypeptide comprises from 1 to 10 covalently attached water-soluble polymers.

In some embodiments, each polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof. In some embodiments, each water-soluble polymer is poly(alkylene oxide). In some embodiments, each water-soluble polymer is polyethylene glycol.

In some embodiments, the polymers are synthesized from suitable precursor materials. In some embodiments, the polymers are synthesized from the precursor materials of, Structure 6, Structure 7, Structure 8, or Structure 9, wherein Structure 6 is:

to TNFα linked to a modified IL-2 polypeptide described herein; and a pharmaceutically acceptable carrier or excipient. In some embodiments, the pharmaceutical composition further comprises one or more excipients, wherein the one or more excipients include, but are not limited to, selected from a carbohydrate, an inorganic salt, an antioxidant, a surfactant, a buffer, or any combination thereof. In some embodiments the pharmaceutical composition further comprises one, two, three, four, five, six, seven, eight, nine, ten, or more excipients, wherein the one or more excipients include, but are not limited to, a carbohydrate, an inorganic salt, an antioxidant, a surfactant, a buffer, or any combination thereof.

In some embodiments, the pharmaceutical composition further comprises a carbohydrate. In certain embodiments, the carbohydrate is selected from the group consisting of fructose, maltose, galactose, glucose, D-mannose, sorbose, lactose, sucrose, trehalose, cellobiose raffinose, melezitose, maltodextrins, dextrans, starches, mannitol, xylitol, maltitol, lactitol, xylitol, sorbitol (glucitol), pyranosyl sorbitol, myo-inositol, cyclodextrins, and combinations thereof.

Alternately, or in addition, the pharmaceutical composition further comprises an inorganic salt. In certain embodiments, the inorganic salt is selected from the group consisting of sodium chloride, potassium chloride, magnesium chloride, calcium chloride, sodium phosphate, potassium phosphate, sodium sulfate, or combinations thereof.

Alternately, or in addition, the pharmaceutical composition further comprises an antioxidant. In certain embodiments, the antioxidant is selected from the group consisting of ascorbyl palmitate, butylated hydroxyanisole, butylated hydroxytoluene, potassium metabisulfite, propyl gallate, Structure 6

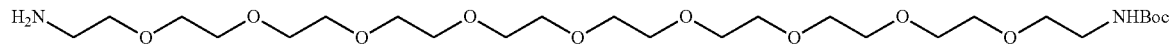

Structure 7 is:

Structure 7

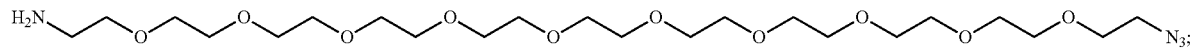

Structure 8 is:

Structure 8

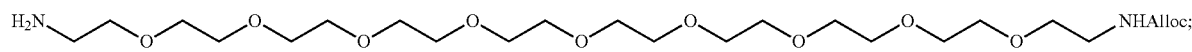

and Structure 9 is:

Structure 9

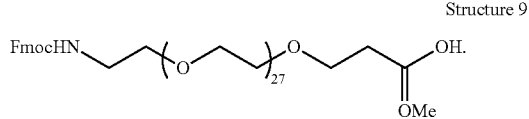

Compositions

In one aspect, described herein is a pharmaceutical composition comprising: a polypeptide which selectively binds sodium metabisulfite, sodium thiosulfate, vitamin E, 3,4-dihydroxybenzoic acid, and combinations thereof.

Alternately, or in addition, the pharmaceutical composition further comprises a surfactant. In certain embodiments, the surfactant is selected from the group consisting of polysorbates, sorbitan esters, lipids, phospholipids, phosphatidylethanolamines, fatty acids, fatty acid esters, steroids, EDTA, zinc, and combinations thereof.

Alternately, or in addition, the pharmaceutical composition further comprises a buffer. In certain embodiments, the buffer is selected from the group consisting of citric acid, sodium phosphate, potassium phosphate, acetic acid, ethanolamine, histidine, amino acids, tartaric acid, succinic acid, fumaric acid, lactic acid, tris, HEPES, or combinations thereof.

In some embodiments, the pharmaceutical composition is formulated for parenteral or enteral administration. In some embodiments, the pharmaceutical composition is formulated for intravenous (IV) or subcutaneous (SC) administration. In some embodiments, the pharmaceutical composition is formulation for intramuscular administration. In some embodiments, the pharmaceutical composition is in a lyophilized form.

In one aspect, described herein is a liquid or lyophilized composition that comprises a described a polypeptide which selectively binds to TNFα linked to a modified IL-2 polypeptide. In some embodiments, the polypeptide which selectively binds to TNFα linked to the modified IL-2 polypeptide modified IL-2 polypeptide is a lyophilized powder. In some embodiments, the lyophilized powder is resuspended in a buffer solution. In some embodiments, the buffer solution comprises a buffer, a sugar, a salt, a surfactant, or any combination thereof. In some embodiments, the buffer solution comprises a phosphate salt. In some embodiments, the phosphate salt is sodium $Na_2HPO_4$. In some embodiments, the salt is sodium chloride. In some embodiments, the buffer solution comprises phosphate buffered saline. In some embodiments, the buffer solution comprises mannitol. In some embodiments, the lyophilized powder is suspended in a solution comprising about 10 mM $Na_2HPO_4$ buffer, about 0.022% SDS, and about 50 mg/mL mannitol, and having a pH of about 7.5.

Dosage Forms

The polypeptide which selectively binds to TNFα linked to the modified IL-2 polypeptides described herein can be in a variety of dosage forms. In some embodiments, polypeptide which selectively binds to TNFα linked to the modified IL-2 polypeptide is dosed as a lyophilized powder. In some embodiments, the polypeptide which selectively binds to TNFα linked to the modified IL-2 polypeptide is dosed as a suspension. In some embodiments, the polypeptide which selectively binds to TNFα linked to the modified IL-2 polypeptide is dosed as a solution. In some embodiments, the polypeptide which selectively binds to TNFα linked to the modified IL-2 polypeptide is dosed as an injectable solution. In some embodiments, the polypeptide which selectively binds to TNFα linked to the modified IL-2 polypeptides is dosed as an IV solution. In some embodiments, the polypeptide which selectively binds to TNFα linked to the modified IL-2 polypeptide is dosed as an intramuscular or subcutaneous formulation.

Methods of Treatment

In one aspect, described herein, is a method of treating an inflammatory disorder in a subject in need thereof, comprising: administering to the subject an effective amount of a polypeptide which selectively binds to TNFα linked to a modified IL-2 polypeptide or a pharmaceutical composition as described herein. In some embodiments, the inflammatory disorder comprises inflammation (e.g., cartilage inflammation), an autoimmune disease, an atopic disease, a paraneoplastic autoimmune disease, arthritis, rheumatoid arthritis (e.g., active), juvenile arthritis, juvenile idiopathic arthritis, juvenile rheumatoid arthritis, pauciarticular rheumatoid arthritis, pauciarticular juvenile rheumatoid arthritis, polyarticular juvenile rheumatoid arthritis, systemic onset juvenile rheumatoid arthritis, juvenile psoriatic arthritis, psoriatic arthritis, polyarticular rheumatoid arthritis, systemic onset rheumatoid arthritis, ankylosing spondylitis, juvenile ankylosing spondylitis, juvenile enteropathic arthritis, reactive arthritis, juvenile reactive arthritis, Reiter's syndrome, juvenile Reiter's syndrome, juvenile dermatomyositis, juvenile scleroderma, juvenile vasculitis, enteropathic arthritis, SEA syndrome (Seronegativity, Enthesopathy, Arthropathy syndrome), dermatomyositis, psoriatic arthritis, scleroderma, vasculitis, myolitis, polymyolitis, dermatomyolitis, polyarteritis nodossa, Wegener's granulomatosis, arteritis, ploymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, dermatitis herpetiformis, Behcet's disease, alopecia, alopecia areata, alopecia totalis, atherosclerosis, lupus, Still's disease, myasthenia gravis, inflammatory bowel disease (IBD), Crohn's disease, ulcerative colitis, celiac disease, asthma, COPD, rhinosinusitis, rhinosinusitis with polyps, eosinophilic esophogitis, eosinophilic bronchitis, Guillain-Barre disease, thyroiditis (e.g., Graves' disease), Addison's disease, Raynaud's phenomenon, autoimmune hepatitis, graft versus host disease, steroid refractory chronic graft versus host disease, transplantation rejection (e.g. kidney, lung, heart, skin, and the like), kidney damage, hepatitis C-induced vasculitis, spontaneous loss of pregnancy, vitiligo, focal segmental glomerulosclerosis (FSGS), minimal change disease, membranous nephropathy, ANCA-associated Glomerulonephropathy, Membranoproliferative Glomerulonephritis, IgA nephropathy, lupus nephritis, or a combination thereof.

In some embodiments, the polypeptide which selectively binds to TNFα linked to the modified IL-2 polypeptide is administered in a single dose of the effective amount of the modified IL-2 polypeptide, including further embodiments in which (i) the polypeptide which selectively binds to TNFα linked to the modified IL-2 polypeptide is administered once a day; or (ii) the polypeptide which selectively binds to TNFα linked to the modified IL-2 polypeptide is administered to the subject multiple times over the span of one day. In some embodiments, the polypeptide which selectively binds to TNFα linked to the modified IL-2 polypeptide is administered daily, every other day, 3 times a week, once a week, every 2 weeks, every 3 weeks, every 4 weeks, every 5 weeks, every 3 days, every 4 days, every 5 days, every 6 days, bi-weekly, 3 times a week, 4 times a week, 5 times a week, 6 times a week, once a month, twice a month, 3 times a month, once every 2 months, once every 3 months, once every 4 months, once every 5 months, or once every 6 months. Administration includes, but is not limited to, injection by any suitable route (e.g., parenteral, enteral, intravenous, subcutaneous, etc.).

An effective response is achieved when the subject experiences partial or total alleviation or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year, about at least 2 years, about at least 3 years, about at least 4 years, about at least 5 years, etc. Overall or progression-free survival can be also measured in months to years. Alternatively, an effective response may be that a subject's symptoms remain static and do not worsen. Further indications of treatment of indications are described in more detail below.

In some instances, a cancer or tumor is reduced by at least 2%, 5%, 10%, 15%, 20%, 25%, 30%, 35%, 40%, 45%, 50%, 55%, 60%, 65%, 70%, 75%, 80%, 85%, 90%, 95%, or 100%.

Combination therapies with one or more additional active agents are contemplated herein. For example, an anti-TNFα antibody can be administered in combination with one or more of the following: a Disease-Modifying Antirheumatic Drug (DMARD), a Nonsteroidal Anti-Inflammatory Drug (NSAID), an aminosalicylate (a compound that contain 5-aminosalicylic acid (5-ASA)), a corticosteroid, an anti-IL12 antibody, or a Janus Kinase (JAK) inhibitor. In some instances, the DMARD is methotrexate, sulfasalazine, hydroxychloroquine, leflunomide, Azathioprine, etc. In some instances, the 5-ASA drug is sulfasalazine (Azulfidine®), a mesalamine (e.g., ASACOL® HD, PENTASA®, LIALDA™, APRISOR, DELZICOL™, etc.), olsalazine (DIPENTUM®), balsalazide (COLAZAL®), CANASA®, ROWASA®, etc. In some instances, the JAK inhibitor is a Janus kinase 1 (JAK1) inhibitor, a Janus kinase 2 (JAK2) inhibitor, a Janus kinase 3 (JAK3) inhibitor, or a combination thereof. In some instances, the anti-IL12 antibody comprises ustekinumab (STELARA®; anti-IL12/IL-23). In some instances, the corticosteroid comprises a glucocorticoid such as, for example, hydrocortisone (CORTEF®), cortisone, ethamethasoneb (Celestone Soluspan (betamethasone sodium phosphate and betamethasone acetate), prednisone (Prednisone Intensol), prednisolone (ORAPRED®, Prelone), triamcinolone (Aristospan Intra-Articular, Aristospan Intralesional, Kenalog), ethylprednisolone (Medrol, Depo-Medrol, Solu-Medrol), dexamethasone, etc. In some instances, the NSAID is Aspirin, celecoxib (CELEBREX®, etc.), diclofenac (CAMBIAR, CATAFLAM®, VOLTAREN®—XR, ZIPSOR®, ZORVOLEX®, etc.), ibuprofen (MOTRIN®, ADVIL®, etc.), indomethacin (INDOCIN®, etc.), naproxen (ALEVER ANAPROX®, NAPRELAN®, NAPROSYN®, etc.), oxaprozin (DAYPRO®, etc.), piroxicam (FELDENE®, etc.), or a combination thereof.

Methods of Manufacturing

In one aspect, described herein, is a method of making a composition, comprising providing a polypeptide which selectively binds to TNFα, wherein the polypeptide which selectively binds to TNFα comprises a reactive group (e.g., a conjugation handle), contacting the reactive group with a complementary reactive group attached to a cytokine, and forming the composition. The resulting composition is any of the compositions provided herein.

In some embodiments, the polypeptide which selectively binds to TNFα is an antibody or an antigen binding fragment thereof. In some embodiments, providing the antibody comprising the reactive group comprises attaching the reactive group to the antibody. In some embodiments, the reactive group is added site-specifically. In some embodiments, attaching the reactive group to the antibody comprises contacting the antibody with an affinity group comprising a reactive functionality which forms a bond with a specific residue of the antibody. In some embodiments, attaching the reactive group to the antibody comprises contacting the antibody with an enzyme. In some embodiments, the enzyme is configured to site-specifically attach the reactive group to a specific residue of the antibody. In some embodiments, the enzyme is glycosylation enzyme or a transglutaminase enzyme.

In some embodiments, the method further comprises attaching the complementary reactive group to the cytokine. In some embodiments, attaching the complementary reactive group to the cytokine comprises chemically synthesizing the cytokine.

In some embodiments, the method comprises making a modified IL-2 polypeptide. In some embodiments, the method of making a modified IL-2 polypeptide comprises synthesizing two or more fragments of the modified IL-2 polypeptide and ligating the fragments. In some embodiments, the method of making the modified IL-2 polypeptide comprises a. synthesizing two or more fragments of the modified IL-2 polypeptide, b. ligating the fragments; and c. folding the ligated fragments.

In some embodiments, the two or more fragments of the modified IL-2 polypeptide are synthesized chemically. In some embodiments, the two or more fragments of the modified IL-2 polypeptide are synthesized by solid phase peptide synthesis. In some embodiments, the two or more fragments of the modified IL-2 polypeptide are synthesized on an automated peptide synthesizer.

In some embodiments, the modified IL-2 polypeptide is ligated from 2, 3, 4, 5, 6, 7, 8, 9, 10, or more peptide fragments. In some embodiments, the modified peptide is ligated from 2 peptide fragments. In some embodiments, the modified IL-2 polypeptide is ligated from 3 peptide fragments. In some embodiments, the modified IL-2 polypeptide is ligated from 4 peptide fragments. In some embodiments, the modified IL-2 polypeptide is ligated from 2 to 10 peptide fragments.

In some embodiments, the two or more fragments of the modified IL-2 polypeptide are ligated together. In some embodiments, three or more fragments of the modified IL-2 polypeptide are ligated in a sequential fashion. In some embodiments, three or more fragments of the modified IL-2 polypeptide are ligated in a one-pot reaction.

In some embodiments, ligated fragments are folded. In some embodiments, folding comprises forming one or more disulfide bonds within the modified IL-2 polypeptide. In some embodiments, the ligated fragments are subjected to a folding process. In some embodiments, the ligated fragments are folding using methods well known in the art. In some embodiments, the ligated polypeptide or the folded polypeptide are further modified by attaching one or more polymers thereto. In some embodiments, the ligated polypeptide or the folded polypeptide are further modified by PEGylation. In some embodiments, the modified IL-2 polypeptide is synthetic.

Sequences (SEQ ID NOS) of IL-2 Polypeptides

TABLE 4

| SEQ ID NO/ Identifier | Modifications | Sequence |
|---|---|---|
| 1 | None (WT) | APTSSSTKKTQLQLEHLLLDLQMILNGINNYKNPK LTRMLTFKFYMPKKATELKHLQCLEEELKPLEEV LNLAQSKNFHLRPRDLISNINVIVLELKGSETTFM CEYADETATIVEFLNRWITFCQSIISTLT |

TABLE 4-continued

| SEQ ID NO/ Identifier | Modifications | Sequence |
|---|---|---|
| 2 | ΔA1, C125S (Aldesleukin) | PTSSSTKKTQLQLEHLLLDLQMILNGINNYKNPKL TRMLTFKFYMPKKATELKHLQCLEEELKPLEEVL NLAQSKNFHLRPRDLISNINVIVLELKGSETTFMC EYADETATIVEFLNRWITFSQSIISTLT |
| 3 (Composition AA) | M23Nle, Y31H, K35R, M39Nle, T41Hse, M46Nle N71Hse, Q74P, N88D, M104Hse, C125S X = Nle, Z = Hse N-terminus with glutaric acid and 0.5kDa azido PEG | APTSSSTKKT QLQLEHLLLD LQXILNGINN HKNPRLTRXL ZFKFYXPKKA TELKHLQCLE EELKPLEEVL ZLAPSKNFHL RPRDLISDIN VIVLELKGSE TTFZCEYADE TATIVEFLNR WITFSQSIIS TLT |
| 4 (Composition AB) | M23Nle, Y31H, K35R, M39Nle, T41Hse, M46Nle, N71Hse, Q74P M104Hse, C125S X = Nle, Z = Hse N-terminus with glutaric acid and 0.5kDa azido PEG | APTSSSTKKT QLQLEHLLLD LQXILNGINN HKNPRLTRXL ZFKFYXPKKA TELKHLQCLE EELKPLEEVL ZLAPSKNFHL RPRDLISNIN VIVLELKGSE TTFZCEYADE TATIVEFLNR WITFSQSIIS TLT |
| 5 (Composition AC) | M23Nle, Y31H, K35R, M39Nle, T41Hse, M46Nle, V69A, N71Hse, Q74P, N88D, M104Hse, C125S X = Nle, Z = Hse N-terminus with glutaric acid and 0.5kDa azido PEG | APTSSSTKKT QLQLEHLLLD LQXILNGINN HKNPRLTRXL ZFKFYXPKKA TELKHLQCLE EELKPLEEAL ZLAPSKNFHL RPRDLISDIN VIVLELKGSE TTFZCEYADE TATIVEFLNR WITFSQSIIS TLT |
| 6 (Composition AD) | M23Nle, Y31H, K35R, M39A, T41Hse, M46Nle N71Hse, Q74P, M104Hse, C125S X = Nle, Z = Hse N-terminus with glutaric acid and 0.5kDa azido PEG | APTSSSTKKT QLQLEHLLLD LQXILNGINN HKNPRLTRAL ZFKFYXPKKA TELKHLQCLE EELKPLEEVL ZLAPSKNFHL RPRDLISNIN VIVLELKGSE TTFZCEYADE TATIVEFLNR WITFSQSIIS TLT |
| 7 (Composition AE) | M23A, Y31H, K35R, M39Nle, T41Hse, M46Nle, N71Hse, Q74P M104Hse, C125S X = Nle, Z = Hse N-terminus with glutaric acid and 0.5kDa azido PEG | APTSSSTKKT QLQLEHLLLD LQAILNGINN HKNPRLTRXL ZFKFYXPKKA TELKHLQCLE EELKPLEEVL ZLAPSKNFHL RPRDLISDIN VIVLELKGSE TTFZCEYADE TATIVEFLNR WITFSQSIIS TLT |
| 8 (Composition AF) | M23Nle, Y31H, K35R, M39Nle, T41Hse, M46A, N71Hse, Q74P, M104Hse, C125S X = Nle, Z = Hse N-terminus with glutaric acid and 0.5kDa azido PEG | APTSSSTKKT QLQLEHLLLD LQXILNGINN HKNPRLTRXL ZFKFYAPKKA TELKHLQCLE EELKPLEEVL ZLAPSKNFHL RPRDLISNIN VIVLELKGSE TTFZCEYADE TATIVEFLNR WITFSQSIIS TLT |
| 9 | M23Nle, K35R, M39Nle, T41Hse, M46Nle, V69A, N71Hse, Q74P, N88D, M104Hse, C125S X = Nle, Z = Hse | APTSSSTKKT QLQLEHLLLD LQXILNGINN YKNPRLTRXL ZFKFYXPKKA TELKHLQCLE EELKPLEEAL ZLAPSKNFHL RPRDLISDIN VIVLELKGSE TTFZCEYADE TATIVEFLNR WITFSQSIIS TLT |

TABLE 4-continued

| SEQ ID NO/ Identifier | Modifications | Sequence |
|---|---|---|
| 10 | M23Nle, M39Nle, T41Hse, F42(4-NH₂)-Phe, M46Nle, N71Hse, N88D, M104Hse, C125S<br>B = (4-NH₂)-Phe<br>X = Nle, Z = Hse | APTSSSTKKT QLQLEHLLLD LQXILNGINN YKNPKLTRXL ZBKFYXPKKA TELKHLQCLE EELKPLEEVL ZLAQSKNFHL RPRDLISDIN VIVLELKGSE TTFZCEYADE TATIVEFLNR WITFSQSIIS TLT |
| 11 | M23Nle, M39Nle, T41Hse, M46Nle, N71Hse, N88D, M104Hse, C125S<br>X = Nle, Z = Hse | APTSSSTKKT QLQLEHLLLD LQXILNGINN YKNPKLTRXL ZFKFYXPKKA TELKHLQCLE EELKPLEEVL ZLAQSKNFHL RPRDLISDIN VIVLELKGSE TTFZCEYADE TATIVEFLNR WITFSQSIIS TLT |
| 12 | M23Nle, M39Nle, T41Hse, M46Nle, N71Hse, N88Dgp, M104Hse, C125S<br>X = Nle, Z = Hse<br>Dgp = D with a O-(2-aminoethyl)-O'-(2-aminoethyl)octa-ethylene glycol | APTSSSTKKT QLQLEHLLLD LQXILNGINN YKNPKLTRXL ZFKFYXPKKA TELKHLQCLE EELKPLEEVL ZLAQSKNFHL RPRDLISDgpIN VIVLELKGSE TTFZCEYADE TATIVEFLNR WITFSQSIIS TLT |
| 13 | Y31H, K35R, V69A, N71R, Q74P, C125S | APTSSSTKKT QLQLEHLLLD LQMILNGINN HKNPRLTRML TFKFYMPKKA TELKHLQCLE EELKPLEEAL RLAPSKNFHL RPRDLISNIN VIVLELKGSE TTFMCEYADE TATIVEFLNR WITFSQSIIS TLT |
| 14 | N29S, Y31H, K35R, T37A, K48E, V69A, N71R, Q74P, N88D, I89V, C125S, Q126T | APTSSSTKKT QLQLEHLLLD LQMILNGISN HKNPRLARML TFKFYMPEKA TELKHLQCLE EELKPLEEAL RLAPSKNFHL RPRDLISDVN VIVLELKGSE TTFMCEYADE TATIVEFLNR WITFSTSIIS TLT |
| 15 | L18R, Q22E, C125S, Q126T | APTSSSTKKT QLQLEHLRLD LEMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFSTSIIS TLT |
| 16 | L18R, Q22E, L80F, R81D, L85V, I86V, N88D, I92F, C125S, Q126T | APTSSSTKKT QLQLEHLRLD LEMILNGINN YKNPKLTRML TFKFYMPKKA TELKHLQCLE EELKPLEEVL NLAQSKNFHF DPRDVVSDIN VFVLELKGSE TTFMCEYADE TATIVEFLNR WITFSTSIIS TLT |
| 17 | Y31H, K35R, V69A, N71R, Q74P, N88D, C125S | APTSSSTKKT QLQLEHLLLD LQMILNGINN HKNPRLTRML TFKFYMPKKA TELKHLQCLE EELKPLEEAL RLAPSKNFHL RPRDLISDIN VIVLELKGSE TTFMCEYADE TATIVEFLNR WITFSQSIIS TLT |
| 18 | Y31H, K35R, Q74P, C125S | APTSSSTKKT QLQLEHLLLD LQMILNGINN HKNPRLTRML TFKFYMPKKA TELKHLQCLE EELKPLEEVL NLAPSKNFHL RPRDLISNIN VIVLELKGSE TTFMCEYADE TATIVEFLNR WITFSQSIIS TLT |
| 19 | Y31H, K35R, N71R, Q74P, C125S | APTSSSTKKT QLQLEHLLLD LQMILNGINN HKNPRLTRML TFKFYMPKKA TELKHLQCLE EELKPLEEVL RLAPSKNFHL RPRDLISNIN VIVLELKGSE TTFMCEYADE TATIVEFLNR WITFSQSIIS TLT |
| 20 | L18R, Q22E, L80F, R81D, L85V, I86V, I92F, C125S | APTSSSTKKT QLQLEHLRLD LEMILNGINN YKNPKLTRML TFKFYMPKKA TELKHLQCLE EELKPLEEVL NLAQSKNFHF DPRDVVSNIN VFVLELKGSE TTFMCEYADE TATIVEFLNR WITFSQSIIS TLT |

TABLE 4-continued

| SEQ ID NO/ Identifier | Modifications | Sequence |
|---|---|---|
| 21 | L18R, L80F, R81D, L85V, I86V, I92F, C125S, Q126T | APTSSSTKKT QLQLEHLRLD LQMILNGINN YKNPKLTRML TFKFYMPKKA TELKHLQCLE EELKPLEEVL NLAQSKNFHF DPRDVVSNIN VFVLELKGSE TTFMCEYADE TATIVEFLNR WITFSTSIIS TLT |
| 22 | L80F, R81D, L85V, I86V, I92F, C125S | APTSSSTKKT QLQLEHLLLD LQMILNGINN YKNPKLTRML TFKFYMPKKA TELKHLQCLE EELKPLEEVL NLAQSKNFHF DPRDVVSNIN VFVLELKGSE TTFMCEYADE TATIVEFLNR WITFSQSIIS TLT |
| 23 | C125S, Q126T | APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFSTSIIS TLT |
| 24 | Y31H, V69A, N71R, Q74P, C125S | APTSSSTKKT QLQLEHLLLD LQMILNGINN HKNPKLTRML TFKFYMPKKA TELKHLQCLE EELKPLEEAL RLAPSKNFHL RPRDLISNIN VIVLELKGSE TTFMCEYADE TATIVEFLNR WITFSQSIIS TLT |
| 25 | Y31H, V69A, Q74P, C125S | APTSSSTKKT QLQLEHLLLD LQMILNGINN HKNPKLTRML TFKFYMPKKA TELKHLQCLE EELKPLEEAL NLAPSKNFHL RPRDLISNIN VIVLELKGSE TTFMCEYADE TATIVEFLNR WITFSQSIIS TLT |
| 26 | N88D, C125S | APTSSSTKKT QLQLEHLLLD LQMILNGINN YKNPKLTRML TFKFYMPKKA TELKHLQCLE EELKPLEEVL NLAQSKNFHL RPRDLISDIN VIVLELKGSE TTFMCEYADE TATIVEFLNR WITFSQSIIS TLT |
| 27 | Y31H, N71R, N88D, C125S | APTSSSTKKT QLQLEHLLLD LQMILNGINN HKNPKLTRML TFKFYMPKKA TELKHLQCLE EELKPLEEVL RLAQSKNFHL RPRDLISDIN VIVLELKGSE TTFMCEYADE TATIVEFLNR WITFSQSIIS TLT |
| 28 | Y31H, N71R, C125S, Q126T | APTSSSTKKT QLQLEHLLLD LQMILNGINN HKNPKLTRML TFKFYMPKKA TELKHLQCLE EELKPLEEVL RLAQSKNFHL RPRDLISDIN VIVLELKGSE TTFMCEYADE TATIVEFLNR WITFSTSIIS TLT |
| 29 | Y31H, K35R, V69A, N71R, Q74P, C125S, Q126T | APTSSSTKKT QLQLEHLLLD LQMILNGINN HKNPRLTRML TFKFYMPKKA TELKHLQCLE EELKPLEEAL RLAPSKNFHL RPRDLISNIN VIVLELKGSE TTFMCEYADE TATIVEFLNR WITFSTSIIS TLT |
| 30 | Y31H, K35R, N71R, Q74P, N88D, C125S | APTSSSTKKT QLQLEHLLLD LQMILNGINN HKNPRLTRML TFKFYMPKKA TELKHLQCLE EELKPLEEVL RLAPSKNFHL RPRDLISDIN VIVLELKGSE TTFMCEYADE TATIVEFLNR WITFSQSIIS TLT |
| 31 | Y31H, K35R, N71R, Q74P, C125S, Q126T | APTSSSTKKT QLQLEHLLLD LQMILNGINN HKNPRLTRML TFKFYMPKKA TELKHLQCLE EELKPLEEVL RLAPSKNFHL RPRDLISNIN VIVLELKGSE TTFMCEYADE TATIVEFLNR WITFSTSIIS TLT |
| 32 | Y31H, K35R, Q74P, N88D, C125S | APTSSSTKKT QLQLEHLLLD LQMILNGINN HKNPRLTRML TFKFYMPKKA TELKHLQCLE EELKPLEEVL NLAPSKNFHL RPRDLISDIN VIVLELKGSE TTFMCEYADE TATIVEFLNR WITFSQSIIS TLT |
| 33 | Y31H, K35R, Q74P, C125S, Q126T | APTSSSTKKT QLQLEHLLLD LQMILNGINN HKNPRLTRML TFKFYMPKKA TELKHLQCLE EELKPLEEVL NLAPSKNFHL RPRDLISNIN VIVLELKGSE TTFMCEYADE TATIVEFLNR WITFSTSIIS TLT |

TABLE 4-continued

| SEQ ID NO/ Identifier | Modifications | Sequence |
|---|---|---|
| 34 | Y31H, V69A, Q74P, N88D, C125S | APTSSSTKKT QLQLEHLLLD LQMILNGINN HKNPKLTRML TFKFYMPKKA TELKHLQCLE EELKPLEEAL NLAPSKNFHL RPRDLISDIN VIVLELKGSE TTFMCEYADE TATIVEFLNR WITFSQSIIS TLT |
| 35 | V69A, Q74P, N88D, C125S | APTSSSTKKT QLQLEHLLLD LQMILNGINN YKNPKLTRML TFKFYMPKKA TELKHLQCLE EELKPLEEAL NLAPSKNFHL RPRDLISDIN VIVLELKGSE TTFMCEYADE TATIVEFLNR WITFSQSIIS TLT |
| 36 | V69A, N88D, C125S | APTSSSTKKT QLQLEHLLLD LQMILNGINN YKNPKLTRML TFKFYMPKKA TELKHLQCLE EELKPLEEAL NLAQSKNFHL RPRDLISDIN VIVLELKGSE TTFMCEYADE TATIVEFLNR WITFSQSIIS TLT |
| 37 | Q74P, N88D, C125S | APTSSSTKKT QLQLEHLLLD LQMILNGINN YKNPKLTRML TFKFYMPKKA TELKHLQCLE EELKPLEEVL NLAPSKNFHL RPRDLISDIN VIVLELKGSE TTFMCEYADE TATIVEFLNR WITFSQSIIS TLT |
| 38 | Y31H, N88D, C125S | APTSSSTKKT QLQLEHLLLD LQMILNGINN HKNPKLTRML TFKFYMPKKA TELKHLQCLE EELKPLEEVL NLAQSKNFHL RPRDLISDIN VIVLELKGSE TTFMCEYADE TATIVEFLNR WITFSQSIIS TLT |
| 39 | Y31H, Q74P, N88D, C125S | APTSSSTKKT QLQLEHLLLD LQMILNGINN HKNPKLTRML TFKFYMPKKA TELKHLQCLE EELKPLEEVL NLAPSKNFHL RPRDLISDIN VIVLELKGSE TTFMCEYADE TATIVEFLNR WITFSQSIIS TLT |
| 40 | Y31H, V69A, N88D, C125S | APTSSSTKKT QLQLEHLLLD LQMILNGINN HKNPKLTRML TFKFYMPKKA TELKHLQCLE EELKPLEEAL NLAQSKNFHL RPRDLISDIN VIVLELKGSE TTFMCEYADE TATIVEFLNR WITFSQSIIS TLT |
| 41 | Y31H, V69A, N71R, Q74P, N88D, C125S | APTSSSTKKT QLQLEHLLLD LQMILNGINN HKNPKLTRML TFKFYMPKKA TELKHLQCLE EELKPLEEAL RLAPSKNFHL RPRDLISDIN VIVLELKGSE TTFMCEYADE TATIVEFLNR WITFSQSIIS TLT |
| 42 | V69A, N71R, Q74P, N88D, C125S | APTSSSTKKT QLQLEHLLLD LQMILNGINN YKNPKLTRML TFKFYMPKKA TELKHLQCLE EELKPLEEAL RLAPSKNFHL RPRDLISDIN VIVLELKGSE TTFMCEYADE TATIVEFLNR WITFSQSIIS TLT |
| 43 | N71R, N88D, C125S | APTSSSTKKT QLQLEHLLLD LQMILNGINN YKNPKLTRML TFKFYMPKKA TELKHLQCLE EELKPLEEVL RLAQSKNFHL RPRDLISDIN VIVLELKGSE TTFMCEYADE TATIVEFLNR WITFSQSIIS TLT |

In Table 4 above, Nle is a norleucine residue and Hse is a homoserine residue. Additionally, Table 4 above refers to several IL-2 variants as containing "N-terminus with glutaric acid and 0.5 kDa azido PEG." For sake of clarity, it is intended that this modification is included when the corresponding molecule is referred to by the Composition identifier associated with the SEQ ID NO, but this modification is not contemplated to be part of the amino acid sequence. For example, SEQ ID NO: 3 does not contain the N-terminus with glutaric acid and 0.5 kDa azido PEG, but Composition AA comprises an amino acid sequence of SEQ ID NO: 3 with the N-terminus with glutaric acid and 0.5 kDa azido PEG.

Although the present disclosure and its advantages have been described in detail, it should be understood that various changes, substitutions and alterations can be made herein without departing from the spirit and scope of the disclosure as defined in the appended claims.

The present disclosure is further illustrated in the following Examples which are given for illustration purposes only and are not intended to limit the disclosure in any way.

EXAMPLES

Example 1. Synthesis of Conjugatable IL-2 variant of SEQ ID NO 3 (Composition AA)

Other synthetic IL-2 polypeptide variants provided herein were synthesized using analogous methods to those provided below for SEQ ID NO 3.

General Procedures

General strategy: A modified IL-2 polypeptide as described herein, such as a modified IL-2 polypeptide having an amino acid sequence of, for example, SEQ ID NO: 3, or any of SEQ ID NOs: 4-12, or a synthetic version of any one of SEQ ID NOs: 13-43, or a modified IL-2 polypeptide otherwise described herein (e.g., an IL-2 polypeptide comprising a modified N-terminal amine as in Composition AA), can be synthesized by ligating individual peptide segments prepared by solid phase peptide synthesis (SPPS). Individual peptides are synthesized on an automated peptide synthesizer using the methods described below.

Materials and solvents: Fmoc-amino acids with suitable side chain protecting groups for Fmoc-SPPS, resins polyethylene glycol derivatives used for peptide functionalization and reagents were commercially available and were used without further purification. HPLC grade CH₃CN from was used for analytical and preparative RP-HPLC purification.

Loading of protected ketoacid derivatives (segment 1-3) on amine-based resin: 5 g of Rink-amide MBHA or ChemMatrix resin (1.8 mmol scale) was swollen in DMF for 30 min. Fmoc-deprotection was performed by treating the resin twice with 20% piperidine in DMF (v/v) at r.t. for 10 min. followed by several washes with DMF. Fmoc-AA-protected-α-ketoacid (1.8 mmol, 1.00 equiv.) was dissolved in 20 mL DMF and pre-activated with HATU (650 mg, 1.71 mmol, 0.95 equiv.) and DIPEA (396 µL, 3.6 mmol, 2.00 equiv.). The reaction mixture was added to the swollen resin. It was let to react for 6 h at r.t. under gentle agitation. The resin was rinsed thoroughly with DMF. Capping of unreacted amines on the resin was performed by addition of a solution of acetic anhydride (1.17 mL) and DIPEA (2.34 mL) in DMF (20 mL). It was let to react at r.t. for 15 min under gentle agitation. The resin was rinsed thoroughly with DCM followed by diethyl ether and dried. The loading of the resin was determined by UV quantification of dibenzofulvene to be 0.25 mmol/g.

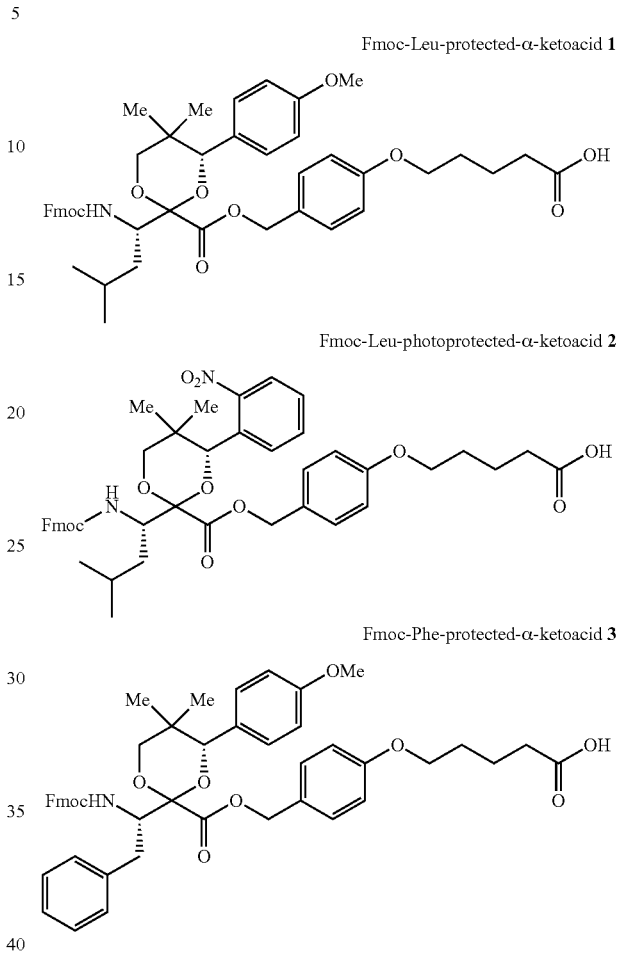

Protected Ketoacid Used

Loading of Fmoc-Thr (tBu)-OH on Wang resin (segment4): Preloading of Fmoc-Thr-OH was performed on a Wang resin. 4 g of resin (loading: 0.56 mmol/g, 2.24 mmol scale) was swollen in DMF for 15 min. The resin was treated with 20% (v/v) piperidine in DMF at r.t. for 20 min. The resin was washed several times with DMF. Fmoc-Thr (tBu)-OH (638 mg, 1.68 mmol, 0.75 equiv.) and HATU (638 mg, 1.68 mmol, 0.75 equiv.) were dissolved in DMF (12 mL). Pre-activation was performed at r.t. for 3 min by addition of DIPEA (585 µL, 3.36 mmol, 1.5 equiv.). The reaction mixture was added to the swollen resin. It was let to react overnight at r.t. under gentle agitation. The resin was rinsed thoroughly with DMF. Capping of unreacted amines on the resin was initiated by addition of a solution of acetic anhydride (1.27 mL) and DIPEA (2.34 mL) in DMF (12 mL). It was let to react at r.t. for 15 min under gentle agitation. The resin was rinsed thoroughly with DCM and dried. The loading of the resin was measured (0.34 mmol/g).

Solid-phase peptide synthesis (SPPS): The peptide segments were synthesized on an automated peptide synthesizer using Fmoc-SPPS chemistry. The following Fmoc-amino acids with side-chain protecting groups were used: Fmoc-Ala-OH, Fmoc-Arg (Pbf)-OH, Fmoc-Asn (Trt)-OH, Fmoc-Asp (OtBu)-OH, Fmoc-Cys (Acm)-OH, Fmoc-Gln (Trt)-OH, Fmoc-Glu (OtBu)-OH, Fmoc-Gly-OH, Fmoc-His (Trt)-

OH, Fmoc-Ile-OH, Fmoc-Leu-OH, Fmoc-Lys (Boc)-OH, Fmoc-Nle-OH, Fmoc-Phe-OH, Fmoc-Pro-OH, Fmoc-Ser (tBu)-OH, Fmoc-Thr (tBu)-OH, Fmoc-Trp (Boc)-OH, Fmoc-Tyr (tBu)-OH, Fmoc-Val-OH, Fmoc or Boc-Opr-OH (Opr=5-(S)-oxaproline). Fmoc-pseudoproline dipeptides were incorporated in the synthesis if necessary. Fmoc deprotections were performed with 20% piperidine in DMF (2×8 min) or 25% piperidine in DMF containing 0.1 M Cl-HOBt (2×8 min) or 20% piperidine in DMF containing 0.1 M Cl-HOBt (2×8 min) and monitored by UV at 304 nm with a feedback loop to ensure complete Fmoc removal. Couplings were performed with Fmoc-amino acid (3.0-5.0 equiv to resin substitution), HCTU or HATU (2.9-4.9 equiv) as coupling reagents and DIPEA or NMM (6-10 equiv) in DMF at r.t. or at 50° C. After pre-activation for 3 min, the solution containing the reagents was added to the resin and allowed to react for 30 min or 2 h depending on the amino acid. In some cases, double couplings were required. In some cases, the resin was treated with 20% acetic anhydride in DMF for capping any unreacted free amine.

Resin cleavage and side chain deprotection of the peptides: Once the peptide synthesis was completed, the peptides were cleaved from the resin using a cleavage cocktail at room temperature for 2 h. The resin was filtered off, and the filtrate was concentrated and treated with cold diethyl ether, triturated and centrifuged. The ether layer was carefully decanted, the residue was suspended again in diethyl ether, triturated and centrifuged. Ether washings were repeated twice. The resulting crude peptide was dried under vacuum and stored at −20° C. An aliquot of the solid obtained was solubilized in 1:1 $CH_3CN/H_2O$ with 0.1% TFA (v/v) and analyzed by analytical RP-HPLC using C18 column (4.6×150 mm) at 60° C. The molecular weight of the product was identified using MALDI-TOF or LC-MS.

Ligation of IL-2 segments 1 and 2 and photodeprotection: IL-2 Seg1 (1.2 equiv) and IL-2 Seg2 (1 equiv) were dissolved in $DMSO/H_2O$ (9:1,v/v) containing 0.1 M oxalic acid (20 mM peptide concentration) and allowed to react at 60° C. for 22 h. The ligation vial was protected from light by wrapping it in aluminum foil. The progress of the KAHA ligation was monitored by HPLC using a C18 column (4.6×150 mm) at 60° C. with $CH_3CN/H_2O$ containing 0.1% TFA as mobile phase, with a gradient of 5 to 95% $CH_3CN$ in 7 min. After completion of the ligation the mixture was diluted with $CH_3CN/H_2O$ (1:1) containing 0.1% TFA and irradiated at a wavelength of 365 nm for 1 h. The completion of photolysis reaction was confirmed by injecting a sample on HPLC using previously described method. The solution was then purified by preparative HPLC.

Ligation of IL-2 segments 3 and 4 and Fmoc deprotection: IL2-Seg3 (1.2 equiv) and IL2-Seg4 (1 equiv) were dissolved in $DMSO/H_2O$ (9.8:0.2) containing 0.1 M oxalic acid (15 mM) and allowed to react for 20 h at 60° C. The progress of the KAHA ligation was monitored by HPLC using a C18 column (4.6×150 mm) at 60° C. using $CH_3CN/H_2O$ containing 0.1% TFA as mobile phase, with a gradient of 30 to 70% $CH_3CN$ in 7 min. After completion of ligation, the reaction mixture was diluted with DMSO (6 mL), 5% of diethylamine (300 µL) was added and the reaction mixture was shaken for 7 min at room temperature. To prepare the sample for purification, it was diluted with DMSO (4 mL) containing TFA (300 µL).

Final ligation: IL2-Seg12 (1.2 equiv) and IL2-Seg34 (1 equiv) were dissolved in $DMSO/H_2O$ (9:1) or (9.8:0.2) containing 0.1 M oxalic acid (15 mM peptide concentration) and the ligation was allowed to proceed for 24 h at 60° C. The progress of the KAHA ligation was monitored by analytical HPLC using a C18 column (4.6×250 mm) at 60° C. and $CH_3CN/H_2O$ containing 0.1% TFA as mobile phase, with a gradient of 30 to 95% $CH_3CN$ in 14 min. After completion of ligation, the reaction mixture was diluted with DMSO followed by further dilution with a mixture of (1:1) $CH_3CN:H_2O$ containing 0.1% TFA (7 mL). The sample was purified by injecting on a preparative HPLC.

Acm deprotection: IL2 linear protein with 2× Acm was dissolved in $AcOH/H_2O$ (1:1) (0.25 mM protein concentration) and AgOAc (1% m/v) was added to the solution. The mixture was shaken for 2.5 h at 50° C. protected from light. After completion of reaction as ascertained by HPLC, the sample was diluted with $CH_3CN:H_2O$ (1:1) containing 0.1% TFA, and purified by preparative HPLC.

Purification of the peptides: Peptide segments, ligated peptides and linear proteins were purified by RP-HPLC. Different gradients were applied for the different peptides. The mobile phase was MilliQ-$H_2O$ with 0.1% TFA (v/v) (Buffer A) and HPLC grade $CH_3CN$ with 0.1% TFA (v/v) (Buffer B). Preparative HPLC was performed on a (50×250 mm) or on a C18 column (50×250 mm) at a flow rate of 40 mL/min at 40° C. or 60° C.

Characterization of the peptides: Peptide segments, ligated peptides and linear proteins were analyzed by RP-HPLC. The mobile phase was MilliQ-$H_2O$ with 0.1% TFA (v/v) (Buffer A) and HPLC grade $CH_3CN$ with 0.1% TFA (v/v) (Buffer B). Analytical HPLC was performed on $C_4$ column (3.6 µm, 150×4.6 mm) at r.t. or C18 column (3.6 µm, 150×4.6 mm) with a flow rate of 1 mL/min at 60° C. Peptides and proteins were characterized by high resolution Fourier-transform mass spectrometry (FTMS) using a SolariX (9.4T magnet) spectrometer (Bruker, Billerica, USA) equipped with a dual ESI/MALDI-FTICR source, using 4-hydroxy-α-cyanocinnamic acid (HCCA) as matrix.

Synthesis of Composition AA (SEQ ID NO: 3 with a Conjugation Handle Attached to the N-Terminal Amine)

Synthesis of IL-2 (1-39)-Leu-α-Ketoacid of SEQ ID NO 3 (Segment 1)

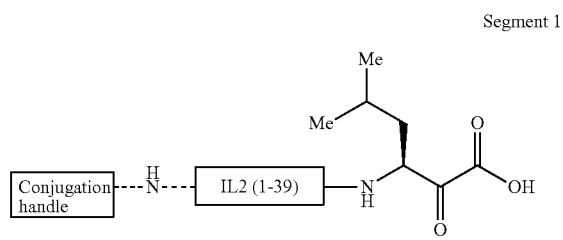

Peptide synthesis: IL2 (1-39)-Leu-α-ketoacid segment 1 (See residues 1-40 of SEQ ID NO: 3) was synthesized on a 0.2 mmol scale on Rink-Amide MBHA resin pre-loaded with Fmoc-Leu-protected-α-ketoacid (0.8 g) with a substitution capacity of ~0.25 mmol/g. Automated Fmoc-SPPS of segment 1 was performed following the general procedure "Solid-phase peptide synthesis (SPPS)". Insertion of the conjugation handle was performed as follow. The first manual coupling reaction was performed at r.t. for 30 min by addition of glutaric anhydride (CAS RN 108-55-4, 114.10 mg, 5 equiv.) and DIPEA (242 µL, 7 equiv.) in DMF to the resin. Secondly, coupling with commercially available O-(2-Aminoethyl)-O'-(2-azidoethyl) nonaethylene glycol (Compound 2, 421 mg, equiv) in DMF was performed at r.t. for 3 hours by addition of DIPEA (276 µL, 8 equiv) and HATU (300 mg, 3.95 equiv) in DMF to the resin. The resin was washed with DCM and dried under vacuum. The mass of the dried peptidyl resin was 1.6 g. The crude peptide was precipitated following the procedure "Resin cleavage and side-chain deprotection of the peptides" using a cocktail of 95:2.5:2.5 TFA/DODT/$H_2O$ v/v/v (10 mL/g resin) at r.t. for 2.0 hours.

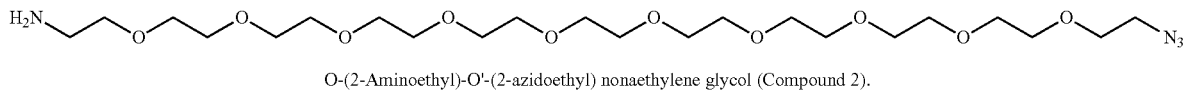 [SMILES: [N-]=[N+]=NCCOCCOCCOCCOCCOCCOCCOCCOCCOCCOCCN]

O-(2-Aminoethyl)-O'-(2-azidoethyl) nonaethylene glycol (Compound 2).

Purification: C18 column (5 μm, 50×250 mm), flow rate 40 mL/min at 60° C., gradient: 30 to 80% B in 25 min. The fractions containing the purified product were pooled and lyophilized to obtain segment 1 as a white solid in 97% purity. The isolated yield based on the resin loading was 260 mg (25%). HRMS (ESI): $C_{228}H_{394}N_{64}O_{72}$; Average isotope calculated 5182.9193 Da $[M+H]^+$; found: 5182.9111 Da $[M+H]^+$.

Synthesis of Opr-IL2 (42-69) Photoprotected-Leu-α-Ketoacid of SEQ ID NO 3 (Segment 2)

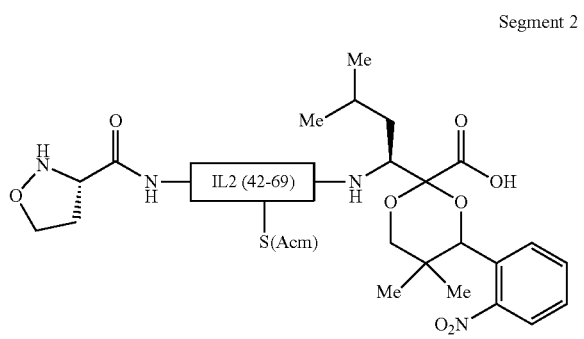

Segment 2

Peptide synthesis: Opr-IL2 (42-69)-Leu-photoprotected-α-ketoacid segment 2 (see 41-70 of SEQ ID NO: 3) was synthesized on a 0.2 mmol scale on Rink-Amide MBHA resin pre-loaded with Fmoc-Leu-photoprotected-α-ketoacid (0.8 g) with a substitution capacity of ~0.25 mmol/g. Automated Fmoc-SPPS of segment 2 was performed following the general procedure "Solid-phase peptide synthesis (SPPS)". The resin was washed with DCM and dried under vacuum. The mass of the dried peptidyl resin was 1.8 g. The crude peptide was precipitated following the procedure "Resin cleavage and side-chain deprotection of the peptides" using a cocktail of 95:2.5:2.5 TFA/DODT/H₂O v/v/v (15 mL/g resin) at r.t. for 2.0 hours.

Purification: C18 column (5 μm, 50×250 mm), flow rate 40 mL/min at 60° C., gradient: 10 to 60% B in 30 min. The fractions containing the purified product were pooled and lyophilized to segment 2 as a white solid in 97% purity. The isolated yield based on the resin loading was 203 mg (20%). MS (ESI): $C_{184}H_{280}N_{40}O_{52}S$; Average isotope calculated: 3922.0742 Da $[M+H]^+$; found: 3922.0680 Da $[M+H]^+$.

Synthesis of Fmoc-Opr IL2 (72-102)-Phe-α-Ketoacid of SEQ ID NO 3 (Segment 3)

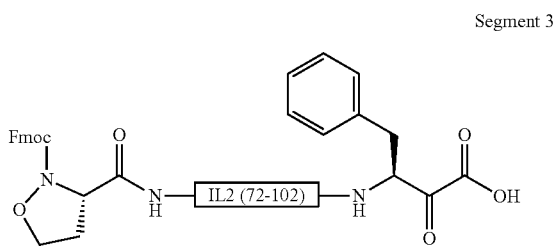

Segment 3

Peptide synthesis: Fmoc-Opr IL2 (72-102)-Phe-α-ketoacid segment 3A (See residues 71-103 of SEQ ID NO: 3) was synthesized on a 0.2 mmol scale on Rink-Amide ChemMatrix resin pre-loaded with Fmoc-Phe-photoprotected-α-ketoacid (0.8 g) with a substitution capacity of ~0.286 mmol/g. Automated Fmoc-SPPS of segment 3 was performed following the general procedure "Solid-phase peptide synthesis (SPPS)". The resin was washed with DCM and dried under vacuum. The mass of the dried peptidyl resin was 2.17 g. The crude peptide was precipitated following the procedure "Resin cleavage and side-chain deprotection of the peptides" using a cocktail of 95:2.5:2.5 TFA/DODT/H₂O v/v/v (10 mL/g resin) at r.t. for 2.0 hours.

Purification: C18 column (5 μm, 50×250 mm), flow rate 40 mL/min at 40° C., 2-step gradient: 10 to 30% B in 10 min followed by 30 to 80% B in 30 min. The fractions containing the purified product were pooled and lyophilized to segment 3 as a white solid in 98% purity. The isolated yield based on the resin loading was 200 mg (17.6%). HRMS (ESI): $C_{184}H_{283}N_{45}O_{53}$; Average isotope calculated 3973.0891 Da $[M+H]^+$; found: 3973.0995 Da $[M+H]^+$.

Synthesis of IL-2 Opr-IL2 (105-133) of SEQ ID NO 3 (Segment 4)

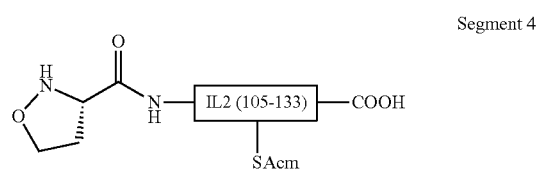

Segment 4

Peptide Synthesis: Opr-IL2 (105-133) Segment 4

Ligation and photodeprotection: The segment 12 was obtained following the general procedure "Ligation of IL-2 segments 1 and 2 and photodeprotection" with 34 mg (6.56 μmol; 1.1 equiv.) of segment 1 and 19 mg (4.9 μmol; 1.0 equiv.) of segment 2 dissolved in 241 μL of 9.5:0.5 v/v DMSO/H₂O solution containing 0.1 M oxalic acid.

Purification: C18 column (5 μm, 50×250 mm), flow rate 40 mL/min at 40° C., 2-step gradient: 10 to 40% B in 5 min followed by 40 to 70% B in 30 min. The fractions containing the purified product were pooled and lyophilized to obtain segment 12 as a white solid in 98% purity. The isolated yield was 55% (25.5 mg). HRMS (ESI): $C_{400}H_{667}N_{103}O_{119}S$; Average isotope calculated: 8855.2806 Da $[M+H]^+$; found: 8855.9008 Da $[M+H]^+$.

KAHA Ligation for the Preparation of IL2-Seg34
of SEQ ID NO 3 (Segment 34)

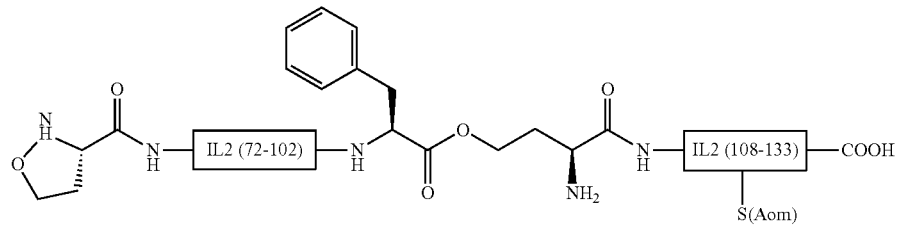

Segment 34

Ligation: The segment 34 was obtained following the general procedure "Ligation of IL-2 segments 3 and 4 and Fmoc deprotection" with 69 mg (17.5 μmol; 1.1 equiv.) of segment 3 and 59 mg (16.6 μmol; 1.0 equiv.) of segment 4 (segment 1234)

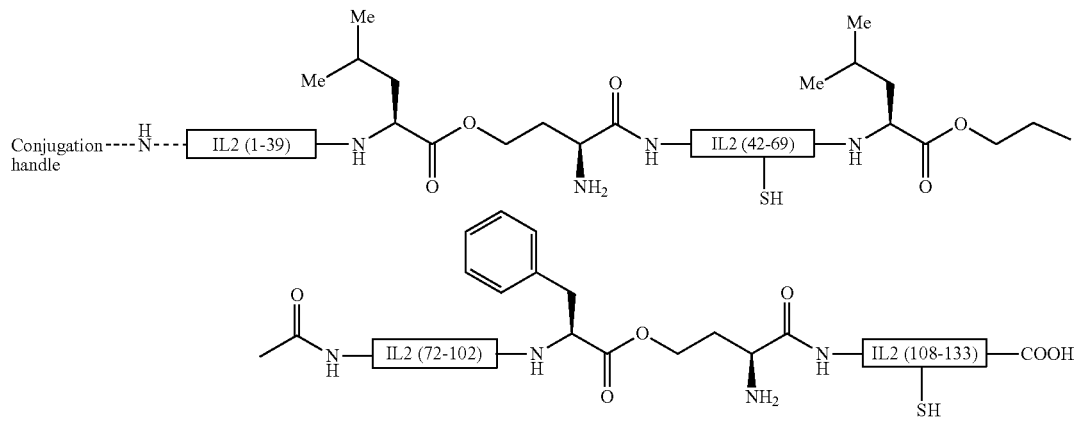

Segment 1234

Ligation: The segment 1234 dissolved in 220 μL of 9.5:0.5 DMSO/H$_2$O v/v containing 0.1 M oxalic acid.

Purification: C18 column (5 μm, 50×250 mm), flow rate 40 mL/min at 40° C., gradient: 30 to 80% B in 30 min. The fractions containing the purified product were pooled and lyophilized to obtain Acm protected segment 1234 as a white solid in 95% purity. The isolated yield was 26% (18 mg).

Acm deprotection: The deprotection of cysteine residues was performed following the general procedure "Acm deprotection" with 18 mg of Acm protected segment 1234 as starting material.

Purification: C18 column (5 μm, 20×250 mm), flow rate 10 mL/min at 40° C., 2-step gradient: 10 to 30% B in 5 min followed by 30 to 95% B in 20 min. The fractions containing the purified product were pooled and lyophilized to obtain segment 1234 as a white solid in 97% purity. The isolated yield was 17% (11.6 mg). HRMS (ESI): $C_{719}H_{1171}N_{183}O_{216}S_2$; Average isotope calculated: 15898.5963 Da [M+H]$^+$; found: 15898.6118 Da [M+H]$^+$.

Folding of IL-2 Linear Protein of SEQ ID NO 3

Rearrangement of linear protein: IL2-Seg1234-A linear protein (11.7 mg, 0.736 μmol) was dissolved in aqueous 6M Gu·HCl containing 0.1 M Tris and 30 mM reduced glutathione (15 μM protein concentration) and the mixture was gently shaken at 50° C. for 2 hours.

Folding of the linear rearranged protein (method 1): After completion of rearrangement reaction, the sample was cooled to room temperature and diluted with 0.1 M Tris and 1.5 mM oxidized glutathione, pH 8.0 (5 μM protein concentration). The folding was allowed to proceed for 20 hours at room temperature. Then, the sample was acidified with TFA to pH 3 and purified by preparative HPLC using a C4 column (20×250 mm) kept at room temperature with a two-step gradient of 5 to 40 to 95% acetonitrile with 0.1% TFA in 60 min, at a flow rate of 10.0 mL/min, using CH$_3$CN/H$_2$O with 0.1% TFA (v/v) as mobile phase. The fractions containing the product were pooled and lyophilized to give pure folded protein Composition AA as a white powder in 98% purity (2.2 mg, 19% yield for folding and purification steps). The purity and identity of the pure protein Composition AA was confirmed by analytical RP-HPLC, MALDI-TOF and analytical size exclusion. HRMS (ESI): $C_{719}H_{1169}N_{183}O_{216}S_2$; Average isotope calculated: 15896.5806 Da [M+H]$^+$; found: 15896.6322 Da [M+H]$^+$.

Example 2. Characterization of Activation of STAT5 by IL-2 Modified Polypeptides Engagement of the IL-2R results in the phosphorylation of STAT5 (signal transducer and activator of transcription 5) and this can be used as a readout to assess selectivity for T cell subsets. Primary pan T-cells were obtained from healthy donor buffy coat by peripheral blood mononuclear cell (PBMC) purification using ficoll gradient centrifugation followed by negative isolation with magnetic beads and then cryopreserved until further use. Pan T-cells were thawed and incubated overnight in T-cell medium (RPMI 10% FCS, 1% Glutamine, 1% NEAA, 25 μM βMeOH, 1% NaPyruvate) followed by two washing steps with PBS. Cells were resuspended in PBS and distributed at 200,000 cells per well followed by incubation for 40 min at 37° C./5% $CO_2$ with aldesleukin, IL-2 modified polypeptides or other controls. After incubation, cells were fixed and permeabilized using the Transcription Factor Phospho Buffer kit followed by a surface and intracellular immunostaining for CD4, CD8, CD25, FoxP3 and phosphorylated STAT5 to enable cell subset identification and measure of levels of P-STAT5 phosphorylation. The FACS measurement was done either with a NovoCyte or a Quanteon Flow Cytometer from Acea. Tregs were classified as CD4+CD25+FoxP3+ cells and $T_{eff}$ as CD8+ T cells. EC50 results of STAT5 phosphorylation assay from the indicated variants in various immune cell types is shown below in Table B.

TABLE B

| Variant | Treg EC50 (nM) | CD4 con EC50 (nM) | CD8 EC50 (nM) | CD8 naïve EC50 (nM) | CD8 memory EC50 (nM) |
|---|---|---|---|---|---|
| Aldesleukin | 0.019 | | 9.069 | 477 | |
| Composition AD (SEQ ID NO 6 + 0.5 kDa azidoPEG) | 0.70 | 32.95 | 69.16 | 795.40 | |
| Composition AE (SEQ ID NO 7 + 0.5 kDa azidoPEG) | 0.90 | 59.06 | 188.92 | 306.10 | |
| Composition AC (SEQ ID NO 5 + 0.5 kDa azidoPEG) | 1.28 | 2296.20 | 2472.92 | 5646.83 | |
| Composition AA (SEQ ID NO 3 + 0.5 kDa azidoPEG) | 2.03 | 1067.90 | 4095.72 | 3867.39 | 424.18 |
| Composition C | 14.77 | 346.04 | 474.68 | 507.91 | 533.62 |
| Composition D | 0.66 | 905.95 | 720.27 | 1000.00 | 1000.00 |

Example 3. Preparation of an Anti-TNFα-IL-2 Immunocytokine

Figure 2A:
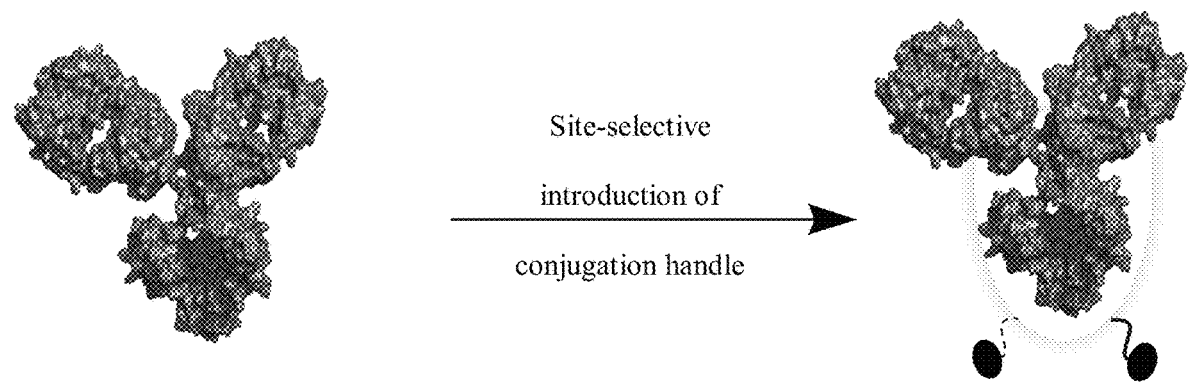
FIG. 2A shows site-selective modification of anti-TNFα antibody by AJICAP™ technology to introduce one or two conjugation handles.

An anti-TNFα antibody (e.g., biosimilar Adalimumab or biosimilar Infliximab) and SEQ ID NO 3 is utilized to prepare an immunocytokine with the following exemplary methods. FIG. 2A illustrates site selective introduction of a conjugation handle on each Fc domain.

Figure 2B:
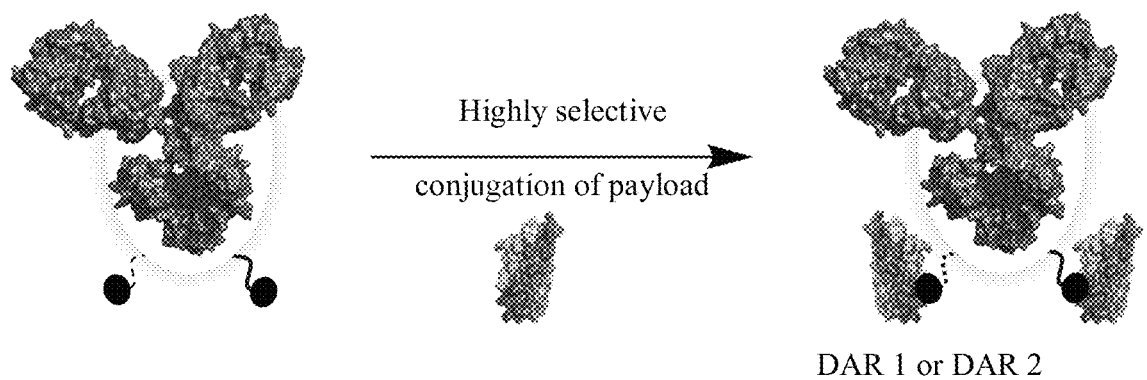
FIG. 2B shows site-selective conjugation reaction of IL-2 cytokine to generate anti-TNFα-IL-2 with a drug antibody ratio of 1 (DAR1), a drug antibody ratio of 2 (DAR2) or mixed DAR between 1 and 2.

A conjugatable variant of biosimilar Adalimumab or biosimilar Infliximab is prepared using an AJICAP™ method. This method allows production of >50 mg of conjugatable anti-TNFα antibody within weeks. The conjugatable product harbors one or two chemical handles for further modifications (FIG. 2B). General protocols for the AJICAP™ methodology are found at least in PCT Publication No. WO2018199337A1, PCT Publication No. WO2019240288A1, PCT Publication No. WO2019240287A1, PCT Publication No. WO2020090979A1, Matsuda et al., Mol. Pharmaceutics 2021, 18, 4058-4066, and Yamada et al., AJICAP: Affinity Peptide Mediated Regiodivergent Functionalization of Native Antibodies. *Angew. Chem., Int. Ed.* 2019, 58, 5592-5597, and in particular Examples 2-4 of US Patent Publication No. US20200190165A1. A general protocol for this methodology is provided below:

A modified anti-TNFα antibody (e.g., biosimilar Adalimumab or biosimilar Infliximab) comprising a DBCO conjugation handle is prepared using a protocol modified from Examples 2-4 of US Patent Publication No. US20200190165A1. Briefly, the anti-TNFα antibody with a free sulfhydryl group attached to a lysine residue side chain in the Fc region is prepared by contacting the antibody with an affinity peptide configured to deliver a protected version of the sulfhydryl group (e.g., a thioester or disulfide) to the lysine residue. An exemplary peptide capable of performing this reaction is shown below, as reported in Matsuda et al., Mol. Pharmaceutics 2021, 18, 4058-4066, which selectively attached the sulfhydryl group via the NHS ester at residue K248 of the Fc region of the antibody (SEQ ID NO: 148)

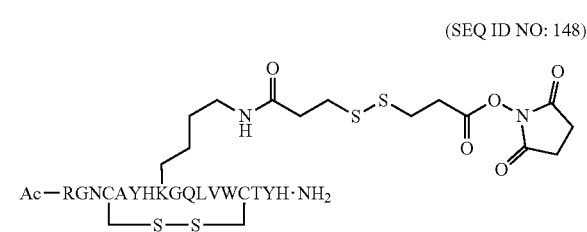

Alternative affinity peptides targeting alternative residues of the Fc region are described in the references cited above for AJICAP™ technology, and such affinity peptides can be used to attach the desired functionality to an alternative residue of the Fc region (e.g., K246, K288, etc.). For example, the disulfide group of the above affinity peptide could instead be replaced with a thioester to provide a sulfhydryl protecting group (e.g., the relevant portion of the affinity peptide would have a structure of

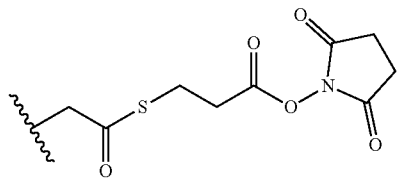

The protecting group (e.g., disulfide or thioester) is then removed to reveal the free sulfhydryl (e.g., by reduction of a disulfide with TCEP or hydrolysis of thioester). The free sulfhydryl is then reacted with a bifunctional reagent comprising a bromoacetamide group connected to the DBCO conjugation handle through a linking group (e.g., bromoacetamido-dPEG®4-amido-DBCO). The method can be used to produce an antibody with one DBCO group present (DAR1) and/or two DBCO groups attached to the antibody (DAR2, one DBCO group linked to each Fc of the antibody).

In another embodiment, antibody comprising a single DBCO conjugation handle is prepared by first reacting excess anti-TNFα antibody with appropriately loaded affinity peptide to introduce a single sulfhydryl after appropriate removal of protecting group (e.g., disulfide reduction or thioester cleavage). A bifunctional linking group with a sulfhydryl reactive conjugation handle and DBCO conjugation handle (e.g., bromoacetamido-dPEG®4-amido-DBCO) is then reacted with the single sulfhydryl to produce the single DBCO containing antibody. The single DBCO containing antibody is then conjugated with a suitable azide containing IL-2 (e.g., Composition AA) to achieve an anti-TNFα-IL-2 immunoconjugate with a DAR of 1.

The purity and identity of the conjugatable variant is confirmed by analytical reverse phase high pressure liquid chromatography (RP-HPLC) and mass spectrometry (Q-TOF). The mass spec profile (Q-TOF) profiles of unmodified anti-TNFα antibody and anti-TNFα antibody+ conjugation handle is determined.

Conjugatable variants of anti-TNFα antibody with one (DAR1) or two (DAR2) reactive handles are reacted with 2-10 equivalents of Composition AA (pH 5.2 buffer, 5% trehalose, rt, 24 hours). The resulting conjugate is purified by cation-exchange chromatography and/or size exclusion chromatography approximately 50-60% yield.

Figure 2C:
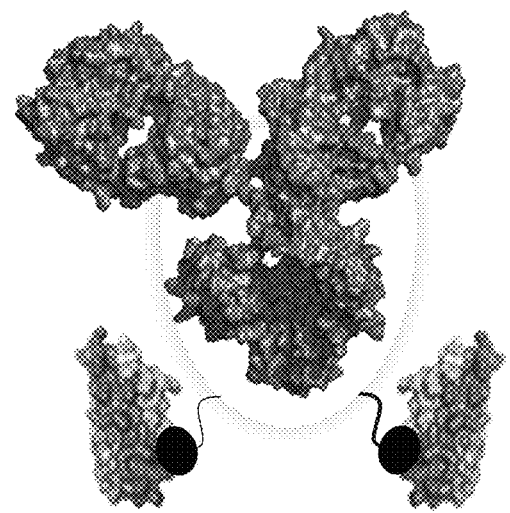
FIG. 2C shows anti-TNFα-IL-2 immunocytokine [DAR2].

A three-dimensional representation of an immunocytokine with two conjugation handles and two payloads is shown in FIG. 2C.

Figure 2D:
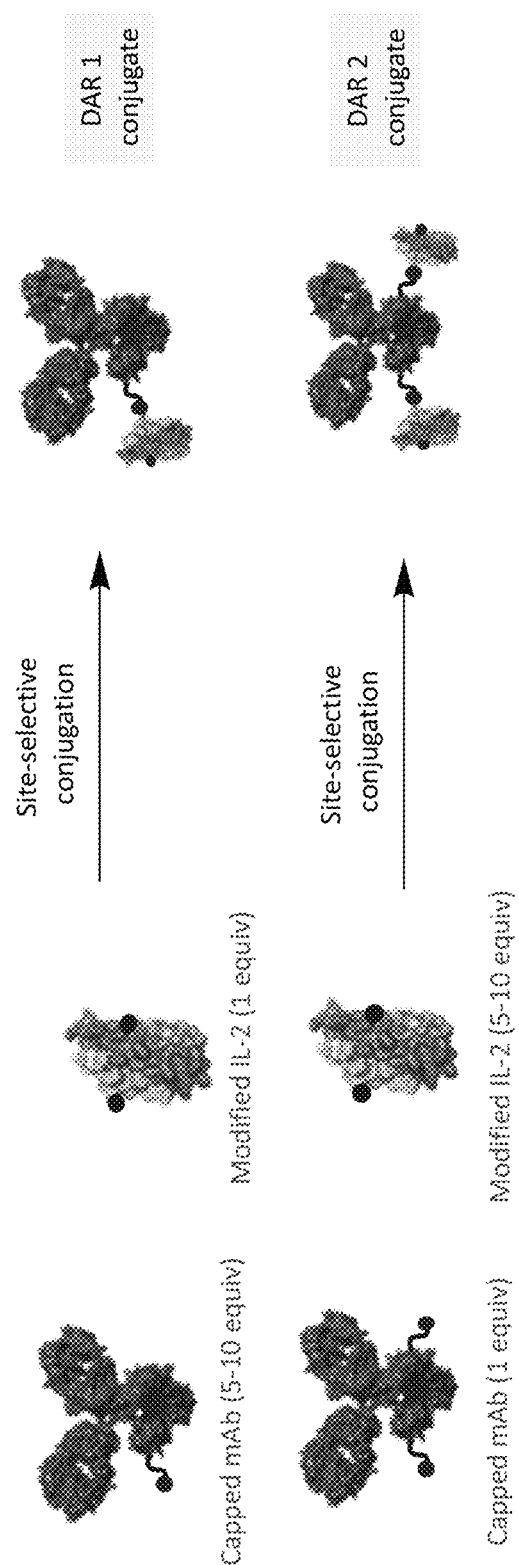
FIG. 2D (top) shows the DAR selective preparation of DAR1 anti-TNFα-IL-2 immunoconjugate by using excess monoclonal antibody with a conjugation handle; (bottom) shows the preparation of clean DAR2 anti-TNFα-IL-2 immunoconjugate by using excess cytokine with a conjugation handle.
Figure 2E:
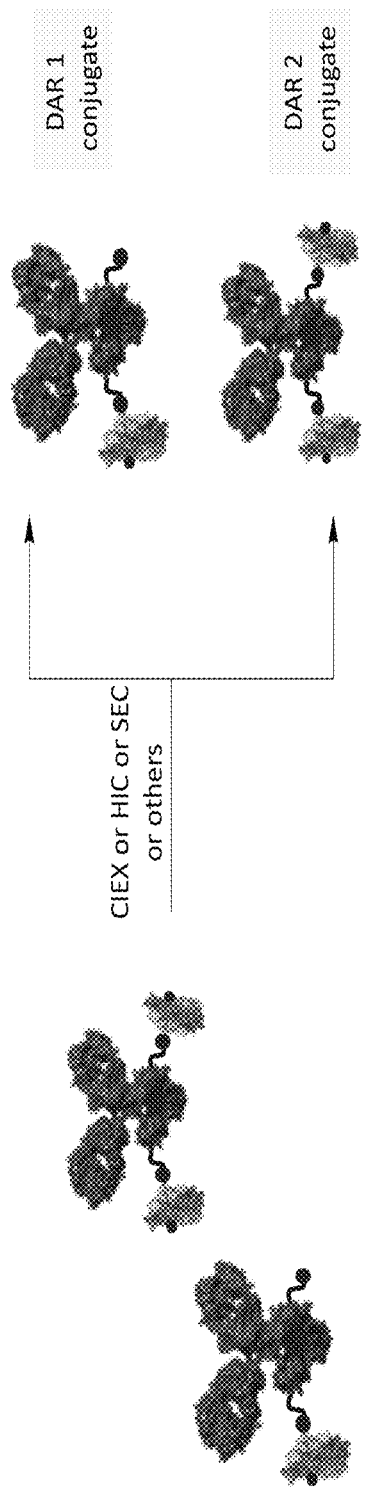
FIG. 2E shows the process for selectively obtaining DAR1 or DAR2 anti-TNFα-IL-2 immunoconjugate by purifying from a crude reaction mixture containing mixed DAR using CIEX, HIC, SEC or other methods.

FIG. 2D (top) shows the preparation of clean DAR1 anti-TNFα-IL-2 immunoconjugate by using excess mAB with a conjugation handle; (bottom) shows the preparation of clean DAR 2 anti-TNFα-IL-2 immunoconjugate by using excess cytokine with a conjugation handle. FIG. 2E shows the process for obtaining clean DAR1 and DAR2 anti-TNFα-IL-2 immunoconjugate by purifying from a crude reaction mixture containing mixed DAR using CIEX, HIC, SEC or other methods.

The anti-TNFα antibody-IL-2 conjugate is purified from unreacted starting product and aggregates using a desalting column, CIEX and SEC (GE Healthcare Life Sciences AKTA pure, mobile phase: Histidine 5.2/150 mM NaCl/5% Trehalose, column: GE Healthcare Life Sciences SUPERDEX™ 200 increase 3.2/300, flow rate: 0.5 mL/min).

The purity and identity of the conjugate is confirmed by RP-HPLC (HPLC: ThermoFisher Scientific UHPLC Ultimate 3000, column: Waters BEH C-4 300A, 3.0 µm, 4.6 mm, 250 mm, mobile phase A: 0.05% TFA in Water, mobile phase B: 0.05% TFA in mixture of ACN:IPA:ETOH:H2O (5:1.5:2:1.5), flow rate: 0.5 mL/min, injection amount: 10 µg (10 µL Injection of 1 mg/mL), gradient: 0% to 20% mobile phase B in 50 min) and SDS-PAGE.

The processes outlined above or analogous methods were used to prepare a variety of the immunocytokine constructs (e.g., anti-TNFα antibodies conjugated to IL-2 polypeptides) provided herein, including those shown in the table below.

TABLE X

| Composition ID | Cytokine | Antibody | DAR | Linker Attachment to Antibody (Fc Eu numbering) |
|---|---|---|---|---|
| A | Composition AA | biosimilar Infliximab | DAR1 | K248 |
| B | Composition AA | biosimilar Infliximab | DAR2 | K248 |
| C | Composition AA | biosimilar Adalimumab | DAR1 | K248 |
| D | Composition AA | biosimilar Adalimumab | DAR2 | K248 |
| E | Composition AA | Trastuzumab | DAR1 | K248 |

Example 4A: TNFα Binding ELISA Assay

The interaction of the unmodified and of conjugated anti-TNFα antibodies with TNFα were measured by ELISA assay. For these studies, Corning high-binding half-area plates (Fisher Scientific, Reinach, Switzerland) were coated overnight at 4° C. with 25 µL of unmodified anti-TNFα antibody or anti-TNFα antibody conjugated to IL-2 polypeptides at 5 µg/mL in PBS. Plates were then washed four times with 100 µL of PBS-0.02% Tween20. Plates surfaces were blocked with 25 µL of PBS-0.02% Tween20-1% BSA at 37° C. during 1 hours. Plates were then washed four times with 100 µL of PBS-0.02% Tween20. Twenty-five 25 µL of recombinant biotinylated TNFα were added in seven-fold serial dilutions starting at 18 nM down to 10 pM into PBS-0.02% Tween20-0.1% BSA and incubated at 37° C. during 2 hours. Plates were then washed four times with 100 µL of PBS-0.02% Tween20. Twenty-five µL of Streptavidin-Horseradish peroxidase (#RABHRP3, Merck, Buchs, Switzerland) diluted at 1:500 into PBS-0.02% Tween20-0.1% BSA were added to each well and incubated at Room Temperature during 30 min. Plates were then washed four times with 100 µL of PBS-0.02% Tween20. Fifty µL of TMB substrate reagent (#CL07, Merck, Buchs, Switzerland) were added to each well and incubated at 37° C. during 5 min. After 5 min at 37° C., Horseradish peroxidase reaction was stopped by adding 50 µL/well of 0.5 M H$_2$SO$_4$ stop solution. ELISA signal was then measured at 450 nm on an ENSPIRE® plate reader from Perkin Elmer (Schwerzenbach, Switzerland).

Figure 3A:
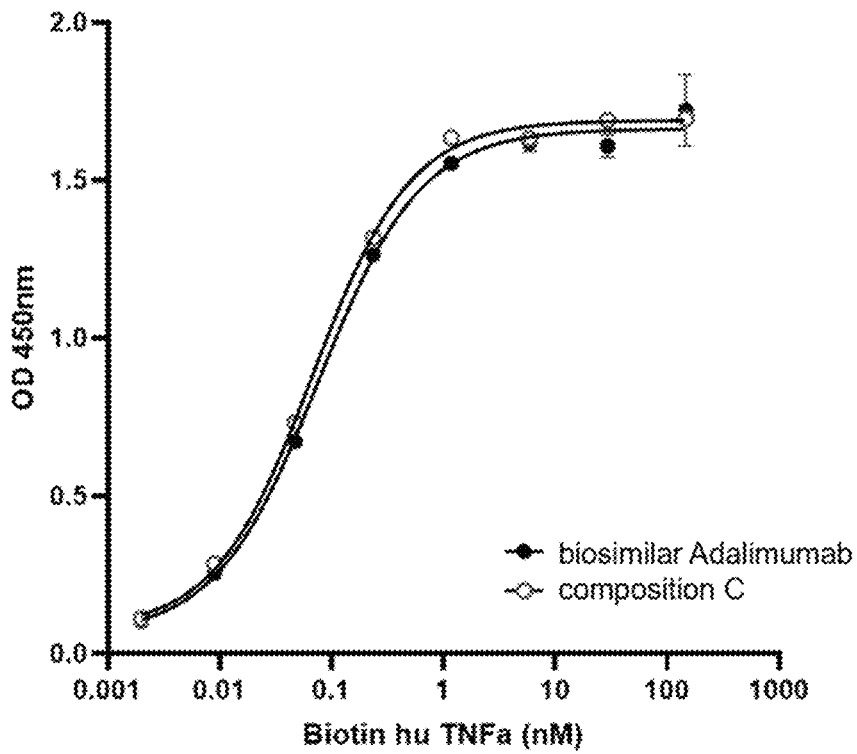
FIG. 3A shows binding to human TNFα by biosimilar Adalimumab and Composition C as provided herein.

There was no difference observed in the binding of biotinylated TNFα to immobilized Composition C compared to biosimilar Adalimumab (FIG. 3A). This result suggests conjugation using the methods discussed supra results in a conjugate which retains the antigen binding capability of the parental antibody.

Figure 3B:
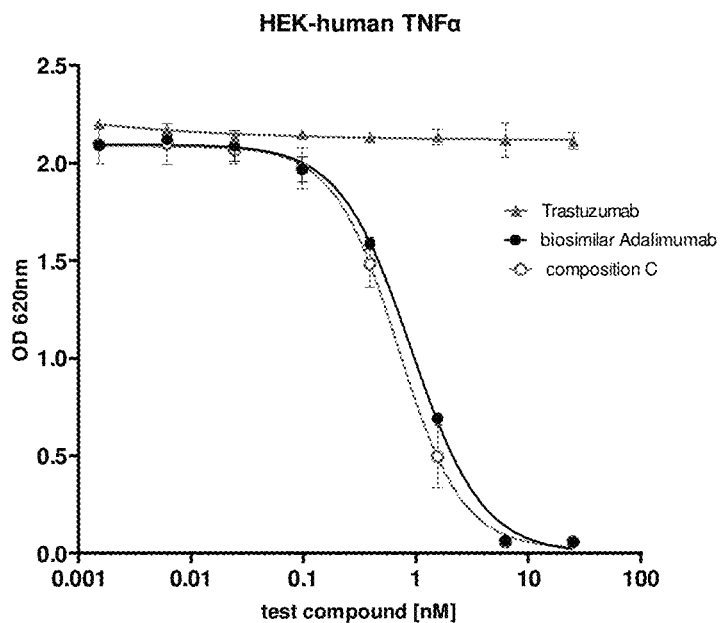
FIG. 3B shows inhibition of TNFα activity by biosimilar Adalimumab and Composition C.

Example 4B: Inhibition of TNFα Activity by Anti-TNFα Conjugated to IL-2 Polypeptides HEK-Blue TNFα reporter cells (Invivogen, hkb-tnfdmyd) were generated by stable transfection of HEK293 cell lines with a secreted alkaline phosphatase (SEAP) reporter gene fused to NF-κB binding sites. Stimulation of HEK-Blue TNFα cells with TNFα triggers the activation of the NF-κB-inducible promoter and the production of SEAP. 50000 cells/well were incubated for 24 hours at 37° C. with a fixed concentration of TNFα at 5 ng/ml (Biolegend, cat 570106) and a 4-fold serial dilution from 25 to 0.0015 nM of unmodified anti-TNFα antibody or anti-TNFα antibody conjugated to IL-2 polypeptides. The anti-HER2 antibody Trastuzumab was used as a non-binding control. Twenty µL of supernatant were mixed with 180 µL of Quanti-blue solution (Invivogen, rep-qbs) and after a 30 min incubation the OD at 620 nm was measured using an EnSpire plate reader from Perkin Elmer (Schwerzenbach, Switzerland). As shown in FIG. 3B, Composition C dose-dependently inhibited TNFα activity with identical potency compared to biosimilar Adalimumab whereas Trastuzumab had no effect. This example, along with example A (FIG. 3A), demonstrate that the anti-TNFα function was preserved in the immunoconjugate.

Figure 4:
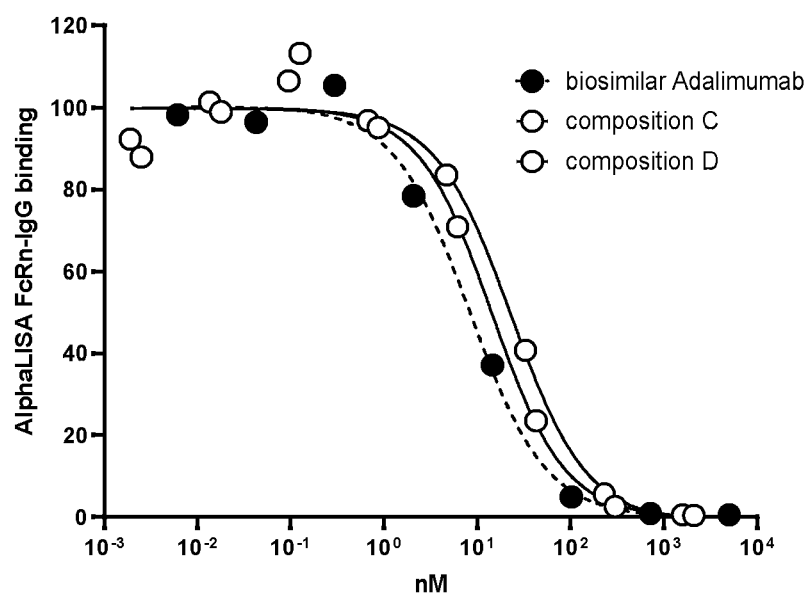
FIG. 4 shows binding to FcRn by biosimilar Adalimumab and Compositions C and D as provided herein
Figure 5A:
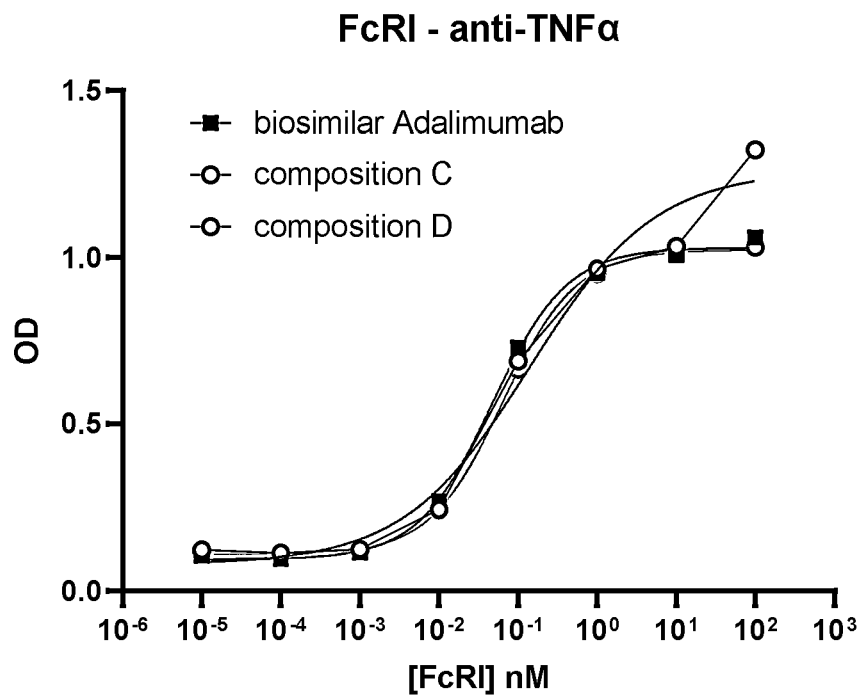
FIG. 5A shows binding to FcRI by biosimilar Adalimumab and Compositions C and D.
Figure 5B:
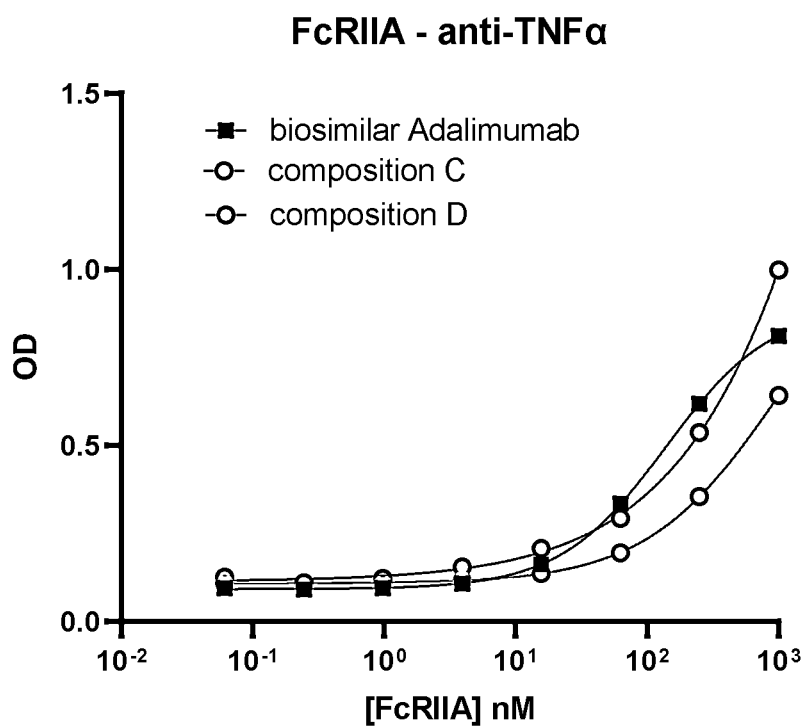
FIG. 5B shows binding to FcRIIα by biosimilar Adalimumab and Compositions C and D.
Figure 5C:
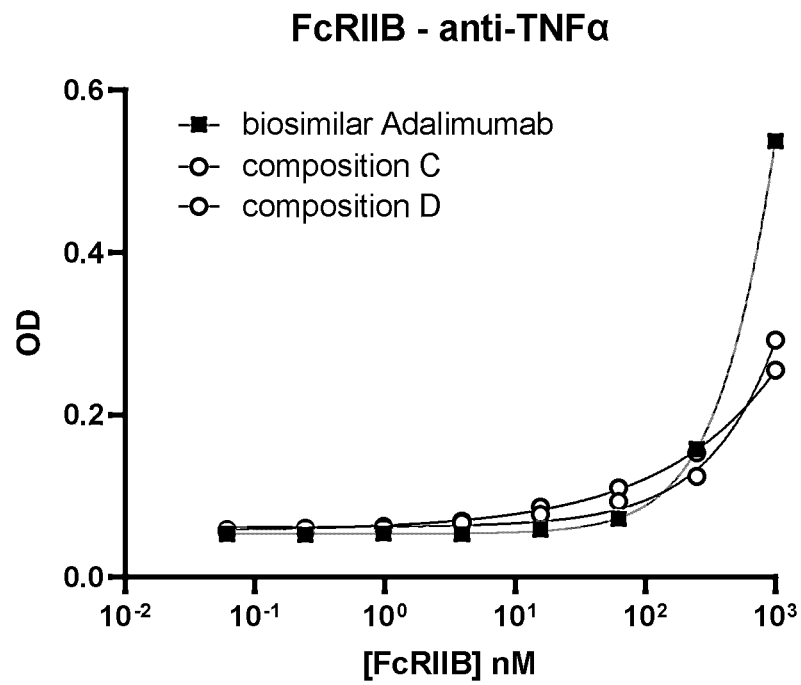
FIG. 5C shows binding to FcRIIβ by biosimilar Adalimumab and Compositions C and D.
Figure 5D:
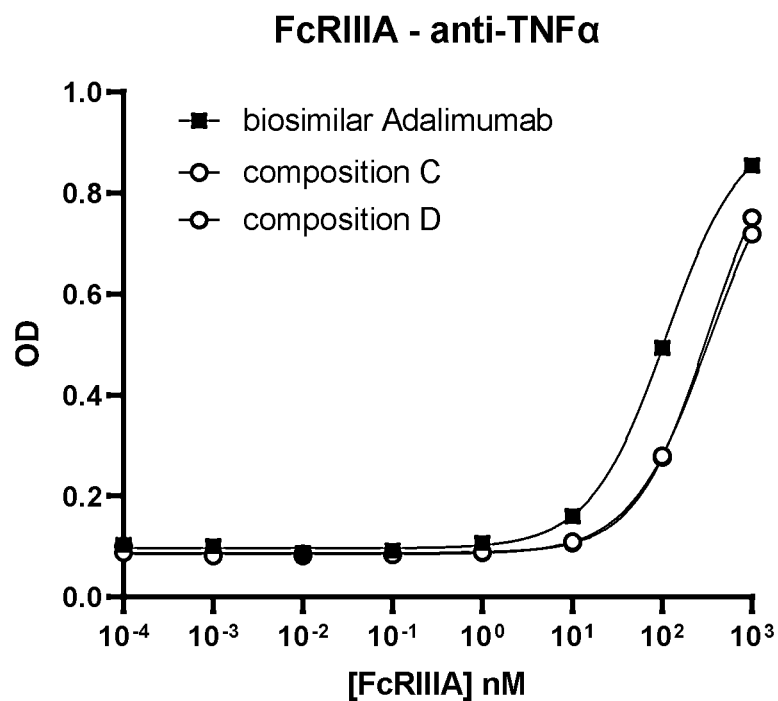
FIG. 5D shows binding to FcRIIIα by biosimilar Adalimumab and Compositions C and D.
Figure 6A:
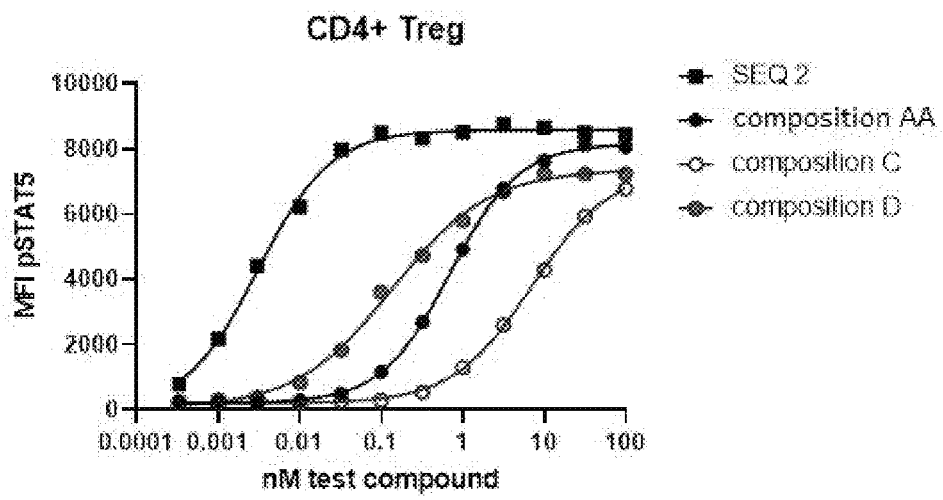
FIG. 6A shows the induction of STAT5 phosphorylation in CD4+ $T_{reg}$ cells following dosing of IL-2 polypeptides or IL-2 immunocytokines as provided herein.
Figure 6B:
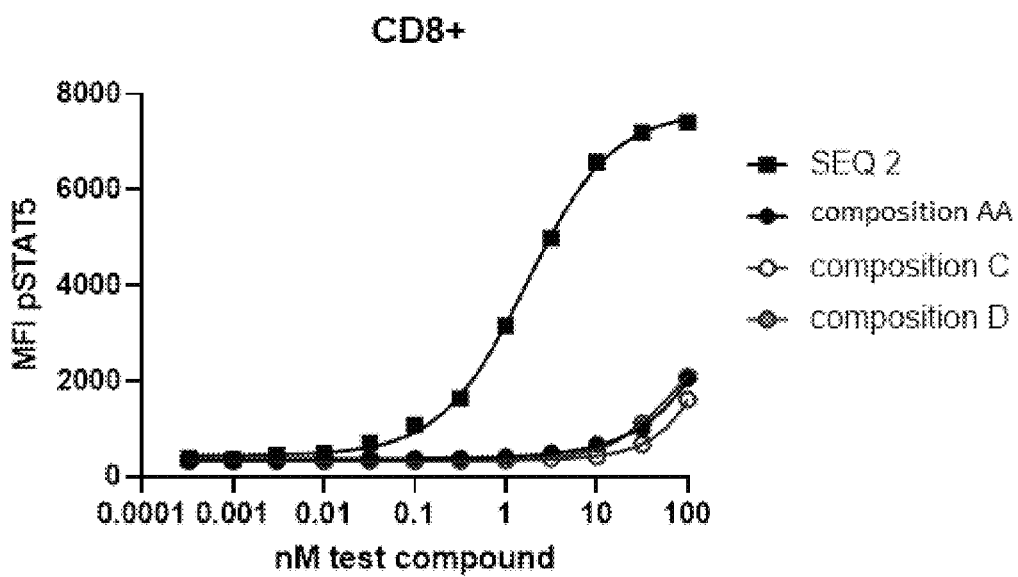
FIG. 6B shows the induction of STAT5 phosphorylation in CD8+ T cells following dosing of IL-2 polypeptides or IL-2 immunocytokines as provided herein.
Figure 6C:
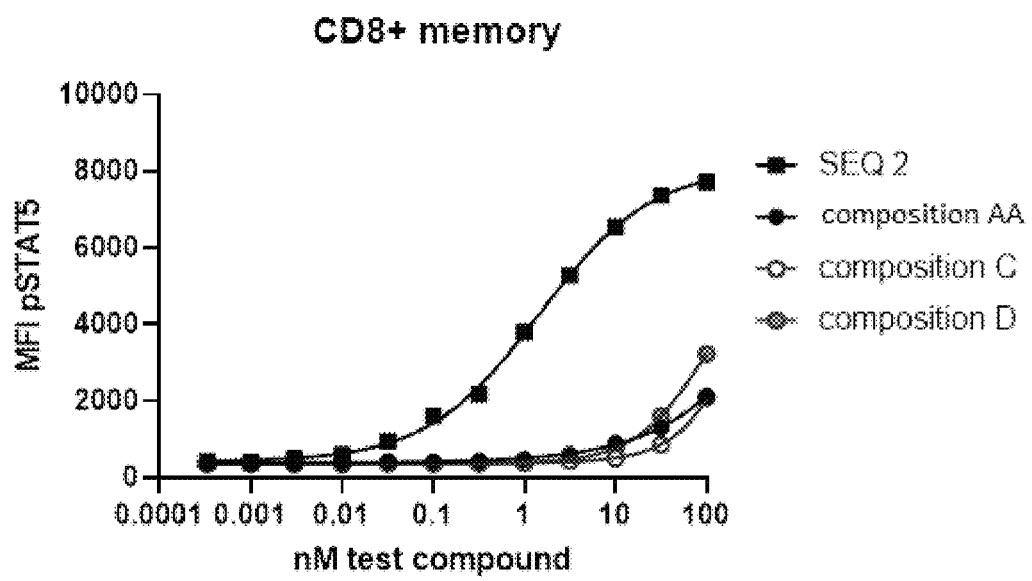
FIG. 6C shows the induction of STAT5 phosphorylation in CD8+ T memory cells following dosing of IL-2 polypeptides or IL-2 immunocytokines as provided herein.
Figure 6D:
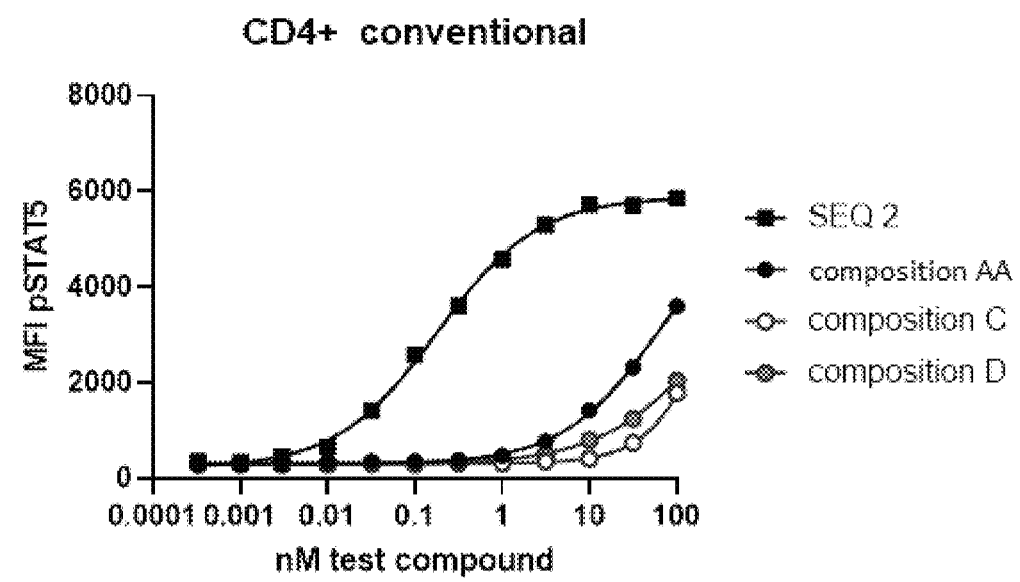
FIG. 6D shows the induction of STAT5 phosphorylation in CD4+ conventional T cells following dosing of IL-2 polypeptides or IL-2 immunocytokines as provided herein.
Figure 6E:
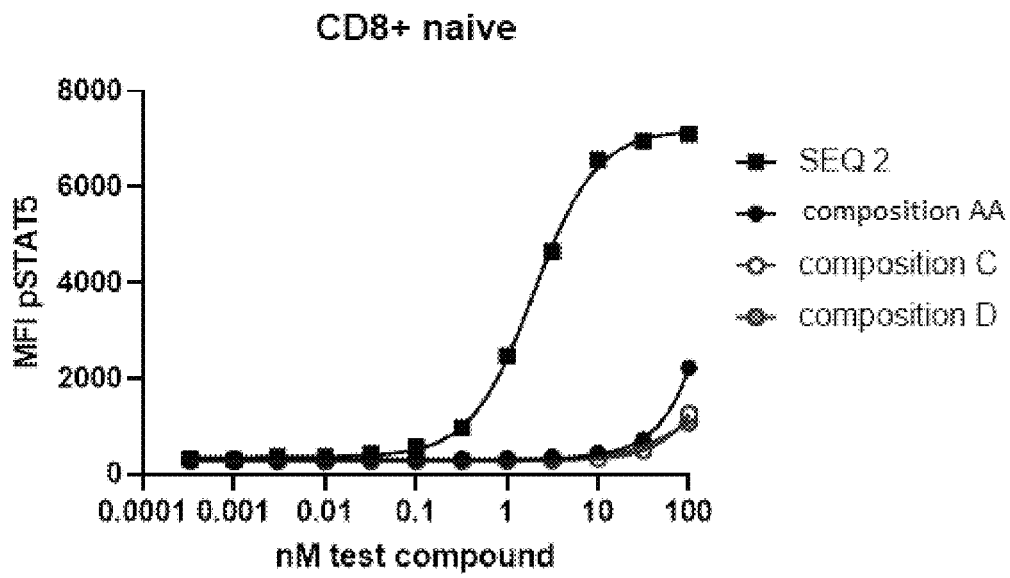
FIG. 6E shows the induction of STAT5 phosphorylation in CD8+ naive T cells following dosing of IL-2 polypeptides or IL-2 immunocytokines as provided herein.
Figure 7A:
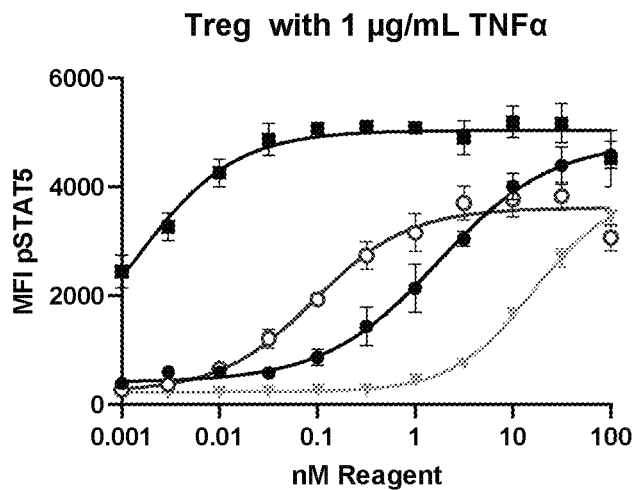
FIG. 7A shows a dose-response curve for the induction of STAT5 phosphorylation in CD4+ $T_{reg}$ cells in the presence of TNFα. For each of FIGS. 7A-7E, half-maximal effective concentrations (EC50, nM) are indicated.
Figure 7B:
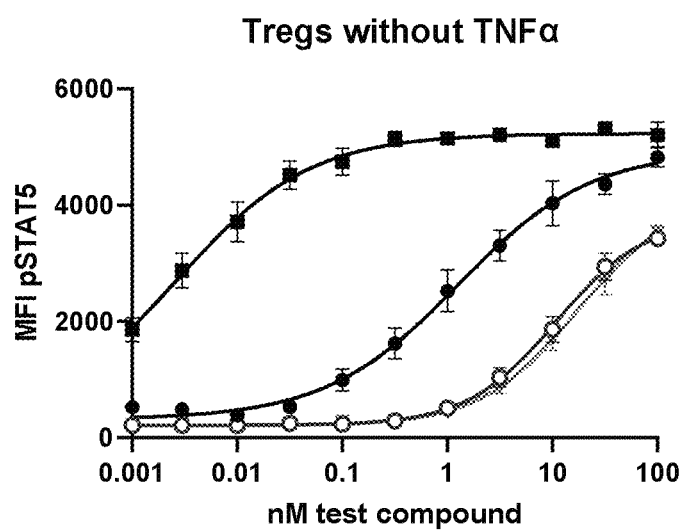
FIG. 7B shows a dose-response curve for the induction of STAT5 phosphorylation in CD4+ $T_{reg}$ cells in the absence of TNFα.
Figure 7C:
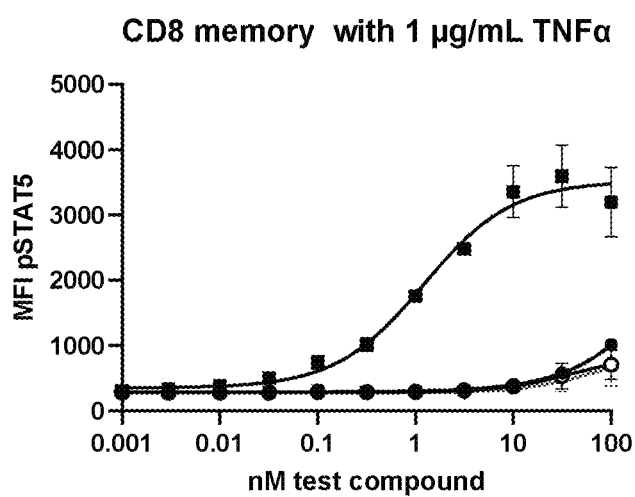
FIG. 7C shows a dose-response curve for the induction of STAT5 phosphorylation in CD8+ T memory cells in the presence of TNFα.
Figure 7D:
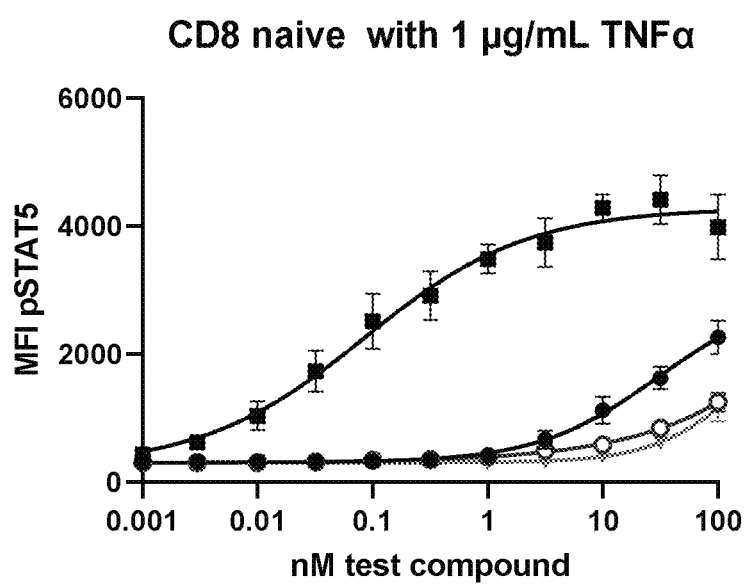
FIG. 7D shows a dose-response curve for the induction of STAT5 phosphorylation in CD8+ naïve T cells in the presence of TNFα.
Figure 7E:
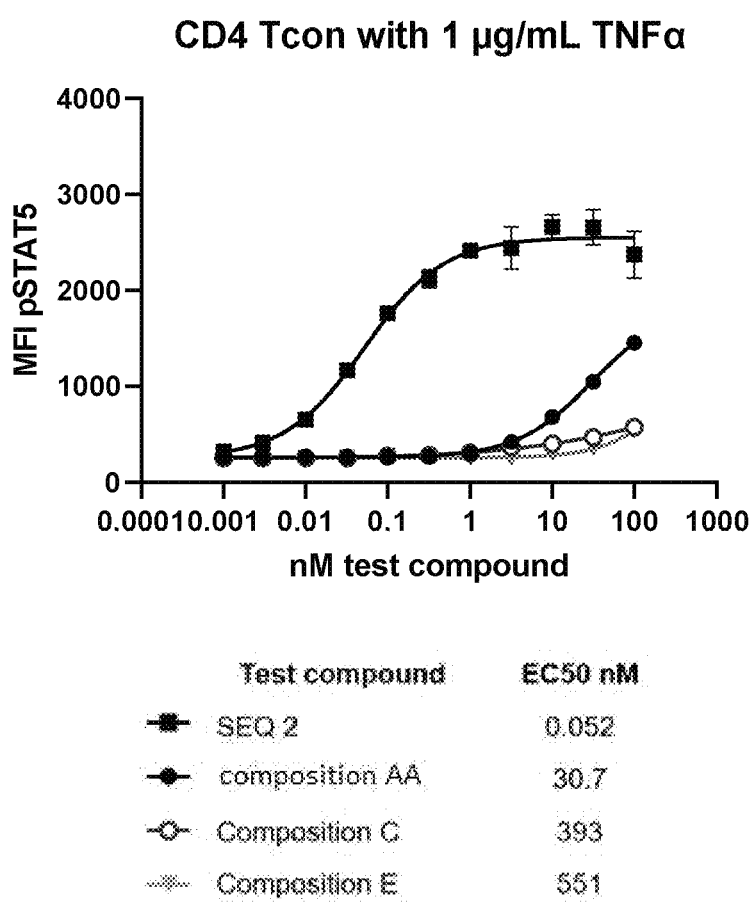
FIG. 7E shows a dose-response curve for the induction of STAT5 phosphorylation in CD4+ T conventional (CD4+ Tcon) cells in the presence of TNFα.

Example 5: Binding of Anti-TNFα Antibody Conjugated to IL-2 Polypeptides to FcRn The interaction of unmodified anti-TNFα antibody or anti-TNFα antibody conjugated to IL-2 polypeptides with the human neonatal Fc receptor (FcRn) at pH 6 was measured using the AlphaLISA® Human FcRn Binding Kit (AL3095C) from Perkin Elmer (Schwerzenbach, Switzerland). The AlphaLISAR detection of FcRn and IgG binding uses IgG coated AlphaLISA® acceptor beads to interact with biotinylated human FcRn captured on Streptavidin-coated donor beads. When reference IgG binds to FcRn, donor and acceptor beads come into proximity enabling the transfer of singlet oxygen that trigger a cascade of energy transfer reactions in the acceptor beads, resulting in a sharp peak of light emission at 615 nm. Addition of a free IgG antibodies into the AlphaLISA® mixture creates a competition for the binding of FcRn to the reference antibody resulting in a loss of signal. Briefly, unmodified anti-TNFα antibody or anti-TNFα antibody conjugated to IL-2 polypeptides were serially diluted and incubated with AlphaLISA® reaction mixture consisting of 800 nM of recombinant biotinylated human FcRn, 40 μg/mL of human IgG conjugated Acceptor beads and 40 μg/mL of Streptavidin coated Donor beads in pH 6 MES buffer. After 90 min at 23° C. in the dark, AlphaLISA® signal was measured on an EnSpire plate reader (Excitation at 680 nm, Emission at 615 nm) from Perkin Elmer (Schwerzenbach, Switzerland). As shown in FIG. 4, conjugation of anti-TNFα antibody to one (Composition C) or two (Composition D) IL-2 polypeptides had little effect on the ability of the molecule to inhibit IgG binding to FcRn, indicating that FcRn binding was only minimally affected by the conjugation Example 6: Binding of Anti-TNFα Antibody Conjugated to IL-2 Polypeptides to FcγR The interaction of the unmodified anti-TNFα antibody or anti-TNFα antibody conjugated to IL-2 polypeptides with human Fc gamma receptor I (FcγRI/CD64), human Fc gamma receptor II (FcγRIIa/CD32) and low affinity human Fc gamma receptor III (FcγR3a/CD16 V158) was measured by ELISA. Antibodies were coated overnight on Maxisorb 96 well plates from Nunc at 4° C. at 2.5 ug/mL. After washing with PBST, plates are blocked for 1 h at 37° C. with PBS containing 1% BSA. His-tagged FcγRI (R&D,1257-FC-050) and FcγRIIIA (R&D 4325-FC-050) were diluted 10-fold starting at 100 nM and 1000 nM, respectively. His-tagged FcγRIIA (R&D9595-CD-050) and Avi-tagged FcγRIIB (R&D, AVI1875-050) were diluted 4-fold starting at 1000 nM. After a 2 hours incubation at 37° C., plates were washed with PBST. Bound FcγRs were detected with biotin anti-His antibody followed by Streptavidin-HRP (SIGMA, RABHRP3), except for FcγRIIB which was detected directly with Streptavidin-HRP. After an incubation for 1 hours at 37° C., plates were washed and incubated with TMB buffer (Sigma CL07) for 5 min at RT. 0.5M $H_2SO_4$ stop solution is added to stop the reaction and the OD at 450 nm measured using an EnSpire plate reader from Perkin Elmer (Schwerzenbach, Switzerland). As shown in FIGS. 5A-D, conjugation of anti-TNFα antibody to one or two IL-2 polypeptides (Compositions C and D) had little effect on the ability of the molecule to bind FcγRs, indicating that the FcγR interaction was only minimally affected by the conjugation.

Example 7: Selective Induction of STAT5 Phosphorylation by Anti-TNFα Antibody Conjugated to IL-2 Polypeptides The phosphorylation of STAT5 was assessed as described in Example 2. Briefly, pan T-cells were resuspended in PBS and distributed at 200,000 cells per well followed by incubation for 40 min at 37° C./5% $CO_2$ with 3.16-fold serial dilutions from 316 nM to 3 pM of aldesleukin (SEQ ID NO: 2), unconjugated IL-2 polypeptide (Composition AA) or anti-TNFα antibody conjugated to IL-2 polypeptide DAR1 (Composition C) or DAR2 (Composition D). After incubation, cells were fixed and permeabilized using the Transcription Factor Phospho Buffer kit followed by a surface and intracellular immunostaining for CD4, CD8, CD25, FoxP3, CD45RA and P-STAT5 (signal transducer and activator of transcription 5) to enable cell subset identification and measure of levels of STAT5 phosphorylation. The FACS measurement was done either with a NovoCyte or a Quanteon Flow Cytometer from Acea. The gating strategy was as follows:

| | |
|---|---|
| T-reg | CD4+, CD25$^{Hi}$, FoxP3+ |
| CD8 Teff | CD8+ |
| Naïve CD8 Teff | CD8+, CD45RA+ |
| Memory CD8 Teff | CD8+, CD45RA− |
| CD4 con | CD4+, FoxP3− |

Like the unconjugated IL-2 polypeptide (Composition AA), anti-TNFα antibody conjugated to IL-2 polypeptide as DAR1 or DAR2 (Compositions C and D) induced STAT5 phosphorylation selectively in Tregs with little effect on STAT5 phosphorylation levels in CD4+ Tcon and CD8+ T cell subsets (FIGS. 6A-6E). On the other hand, aldesleukin non-selectively triggered STAT5 phosphorylation in all the T cell subsets. Composition C was less potent in inducing STAT5 phosphorylation compared to Composition AA, suggesting that antibody conjugation reduces the potency of the IL-2 polypeptide. Compared to Composition C, the DAR2 format (Composition D) was more potent in inducingSTAT5 phosphorylation in Tregs, which may be due to an avidity effect whereby binding of one of the conjugated IL-2 polypeptides to an IL-2R on the cell surface facilitates the binding of the second IL-2 to another IL-2R on the same cell.

Example 8: TNFα Potentiates the Activity of Anti-TNFα Antibody Conjugated to IL-2 Polypeptides Given that TNFα exists as a trimer, the possibility exists that the binding of anti-TNFα antibody conjugated to IL-2 polypeptides to trimeric TNFα will lead to the multimerization of the immunoconjugate and hence increase the avidity of the conjugated IL-2 polypeptide for IL-2R on the cell surface, leading to increased stimulation of STAT5 phosphorylation. The STAT5 phosphorylation assay described above in example G was performed where soluble recombinant TNFα (Biolegend, cat 570106) at 1 μg/mL was preincubated for 30 min with a concentration range of anti-TNFα antibody conjugated to IL-2 polypeptide DAR1 (Composition C). An anti-HER2 antibody conjugated to IL-2 polypeptide DAR1 (Composition E) was used as a non-TNFα binding immunocytokine control and the unconjugated IL-2 polypeptide (SEQ ID NO:3) was used as a positive control. Pre-incubation with TNFα increased the level of STAT5 phosphorylation in Tregs by Composition C whilst maintaining selectivity over activation in other T cell subsets, but had no effect on the potency of the Composition E nor SEQ ID NO:3 (FIGS. 7A-E), thus indicating that the engagement of the Composition C with its multimeric ligand most likely increased its avidity for and activation of IL-2Rα.

Example 9: TNFα Augments Ex Vivo $T_{reg}$ Cell Expansion by Anti-TNFα Antibody Conjugated to IL-2 Polypeptides To determine if the TNFα-mediated increase in STAT5 phosphorylation translates into an effect on $T_{reg}$ expansion ex vivo, parental anti-TNFα antibody (biosimilar Adalimumab) and anti-TNFα:IL-2 IC DAR1 (Composition C) were pre-incubated for 30 min with and without recombinant TNFα (Biolegend, cat 570106) at 1 µg/mL and then incubated with human pan T cells from healthy donors for 5 days in T cell medium (RPMI, 10% FCS, 1× Glutamine, 1% NEAA, 25 uM bMeoH). Anti-HER2:IL-2 IC DAR1 (Composition E) was used as a non-TNFα binding IC control and an unconjugated IL-2 polypeptide (Composition AA) was used as a positive control. Cells were first stained with a viability dye (ZombieNIR, Biolegend 423106) followed by staining for extracellular markers and then fixed, permeabilized and stained using a FOXP3 staining kit (Invitrogen 00-5523-00). After a final wash with PBS containing 2% FBS, cells were resuspended in FACS buffer and acquired with an ACEA Quanteon flow cytometer. Antibodies used for T cell phenotyping were as follows:

| CD8-AF700 | Biolegend | 344724 |
| CD4-BV650 | Biolegend | 317436 |
| CD120B-PE | R&D | FAB226P |
| CD25-BV421 | Biolegend | 356114 |
| FoxP3-AF647 | Biolegend | 320214 |
| Ki67-PE-Dazzle 594 | Biolegend | 350534 |

Figure 8A:
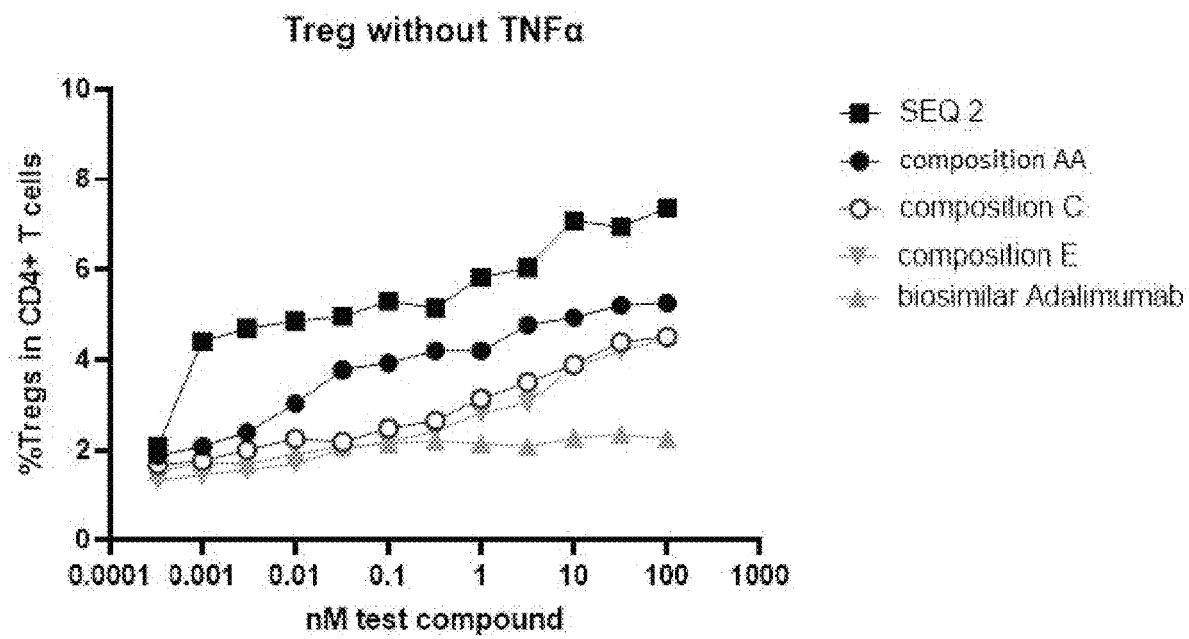
FIG. 8A shows a dose-response curve for the increase in percentage of Tregs among the CD4+ T cell population in the absence of TNFα.
Figure 8B:
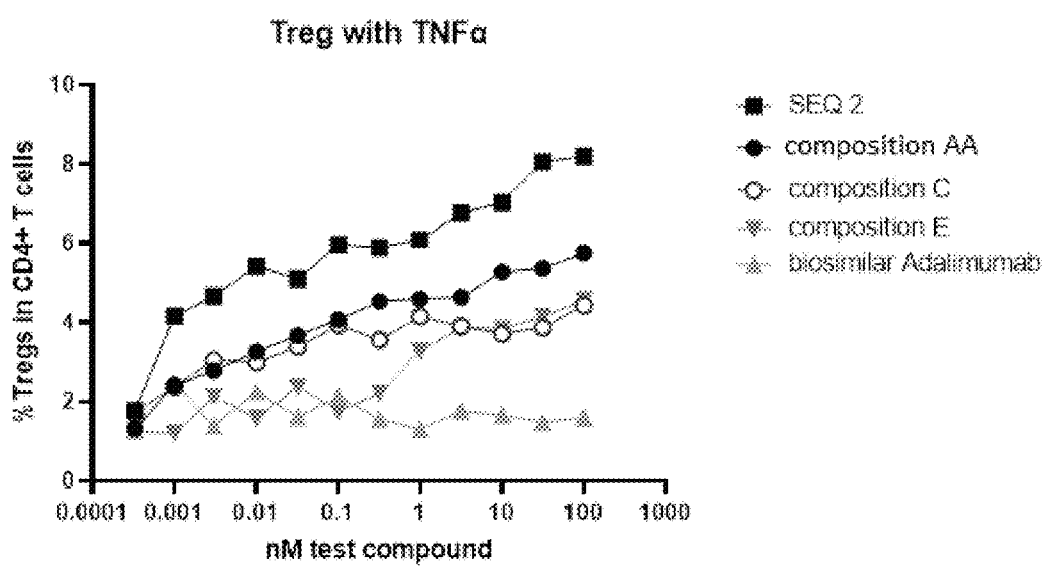
FIG. 8B shows a dose-response curve for the increase in percentage of $T_{reg}$ among the CD4+ T cell population in the presence of TNFα.

In the absence of a TNFα pre-incubation, $T_{reg}$ expansion, as measured by the proportion of Tregs in the CD4+ T cell population, increased in a dose-dependent manner with the unconjugated IL-2 polypeptide and with a similar potency for anti-TNFα:IL-2 IC DAR1 and anti-HER2:IL-2 IC DAR1, whereas the parental anti-TNFα antibody had no effect. In the presence of TNFα, the potency of $T_{reg}$ expansion was increased for anti-TNFα:IL-2 IC DAR1 but not for anti-HER2:IL-2 IC DAR1 nor the unconjugated IL-2 polypeptide (FIGS. 8A and 8B), demonstrating that the TNFα-mediated increase in potency of STAT5 activation observed in example 9 translated into an increased ex vivo expansion of Tregs by anti-TNFα:IL-2 IC DAR 1. This TNFα-mediated increase in potency may facilitate augmented activity of anti-TNFα:IL-2 IC DAR 1 in inflamed tissues where TNFα is produced at high levels.

Example 10: Pharmacokinetic/Pharmacodynamic Studies in Mice for Compositions A and B Single-dose pharmacokinetic/pharmacodynamic (PK/PD) studies were performed in C57/BL6J Tg1278TNFKO mice receiving a single subcutaneous (sc) injection of Compositions A or B at a dose of 1 mg/kg. Blood was sampled at various timepoints in K₂EDTA, plasma was generated by centrifugation and stored at −80° C. until PK analysis and cell pellets were freshly subjected to staining for flow cytometry analysis.

Cell pellets were treated with red blood cell lysis buffer during 5 min. After washing, cells were permeabilized using cold BD Perm Buffer III and stained with antibodies against CD25, FoxP3, CD3, CD4, CD8a, TNFα, Ly6c, CD49d, TNFR2 and pSTAT5. The FACS (fluorescence activated cell sorting) measurement was done with a BD FACSAria from BD and analysis was performed with FlowJo™ (BD Biosciences) software.

Figure 9C:
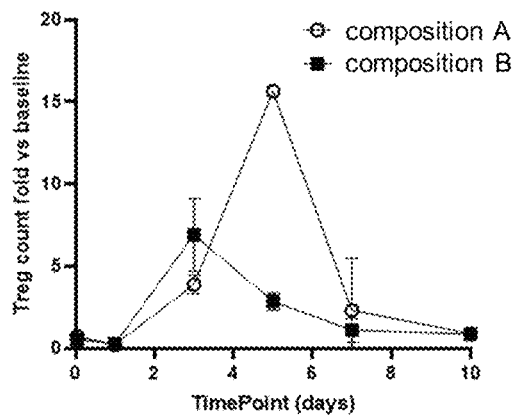
FIG. 9C shows a time-profile of CD4+ Tcon count (as fold change vs baseline) in mice after subcutaneous administration of Composition A or Composition B at 1 mg/kg.
Figure 9C:
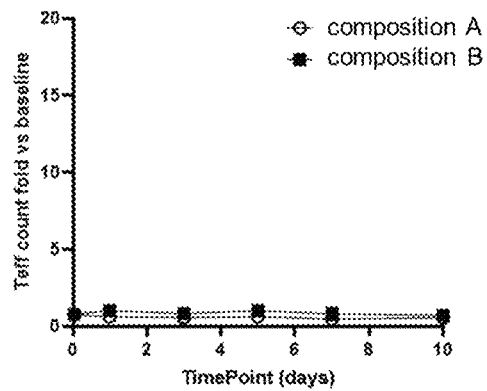
Figure 9C:
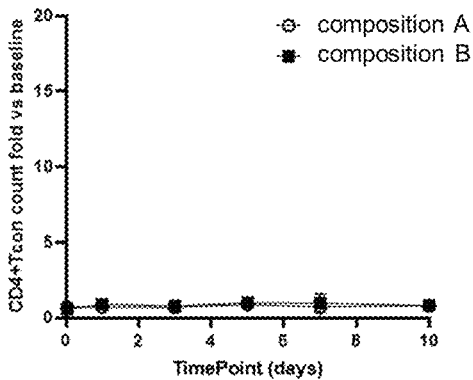

The immuno PD profiles of Compositions A and B were assessed concurrently in the same study and monitored for 10 days. A single dose treatment led to a very pronounced and long lasting increase in $T_{reg}$ cell numbers compared to baseline. Cell expansion was selective to the Treg subpopulation (FIG. 9A) and CD8+ T effector (FIG. 9B) and NK cells (FIG. 9C) remained comparably unchanged.

Figure 10:
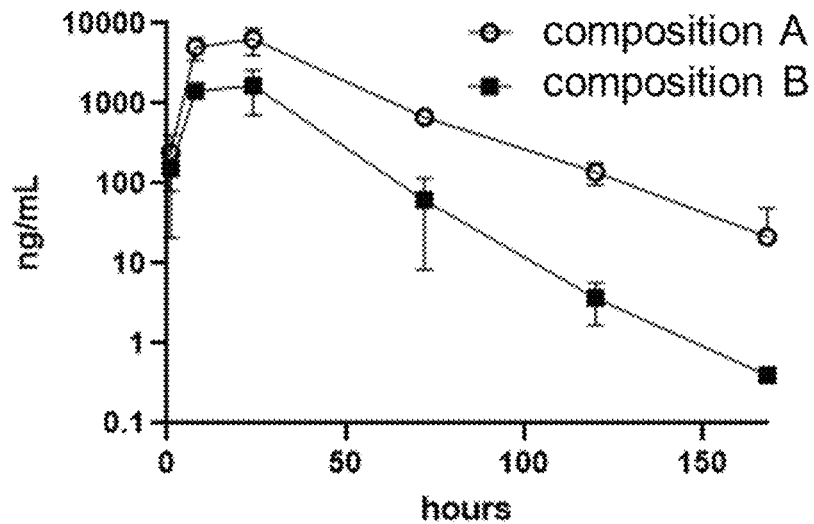
FIG. 10 shows the pharmacokinetic (PK) profile of Compositions A and B administered subcutaneously to mice at 1 mg/kg.

Plasma samples were analyzed for immunocytokine concentration using a colorimetric ELISA (enzyme-linked immunosorbent assay) and anti-IL-2 and anti-human-IgG1 antibodies as capture and detection reagents, respectively. PK data were subjected to a non-compartmental PK analysis by using the PKanalix software. The linear/log trapezoidal rule was applied in obtaining the PK parameters. The subcutaneous PK profile of the immunocytokines (FIG. 10) showed a time to reach maximal concentration of 24 hours and half-lives of 16 and 12 hours for Compositions A and B respectively. Table 5 below shows the calculated PK.

TABLE 5

| Test compound | Composition A | Composition B |
|---|---|---|
| Dosing route | SC | SC |
| Dose (mg/kg) | 1 | 1 |
| Cmax (ng/mL) | 6371 | 1665 |
| Tmax (h) | 24 | 24 |
| T1/2 (h) | 15.9 | 12.0 |
| AUC0-inf (ng · h/mL) | 252100 | 54800 |

Example 11: Composition a Attenuates Collagen Antibody-Induced Arthritic Inflammation Tg1278/TNFKO mice contain ~50 copies of a transgene encoding the complete human TNF gene with flanking regions coupled with a knock-out of the endogenous mouse TNF gene and thus express normally regulated human TNF in the absence of mouse TNF (Moore, A. R. et al. Collagen II antibody-induced arthritis in Tg1278TNFko mice: optimization of a novel model to assess treatments targeting human TNFα in rheumatoid arthritis. J Transl Med 12, 285, 2014).

As human TNF does not activate mouse TNFR2, hTNF/hTNFR2 mice were generated on a C57BL/6 background where the targeted mouse TNF whole genomic sequence was replaced by human TNF whole genomic sequence and, in addition, exons 2-6 of the mouse TNFR2 gene that encode the extracellular domain of the receptor were replaced by human TNFR2 exons 2-6. Expression of human TNF was confirmed by ELISA of serum from LPS-challenged mice and surface humanTNFR2 expression was confirmed by FACS analysis of splenocytes from mice treated with anti-CD3 (data not shown).

To demonstrate that the anti-TNF functionality of Composition A is active in vivo, the efficacy of the molecule was assessed in a collagen antibody-induced arthritis (CAIA) model in comparison to Infliximab. Here, mice are passively immunized with anti-collagen II antibodies that cause joint inflammation. Pathogenesis shares several pathological features with human rheumatoid arthritis including synovial hyperplasia, mononuclear cell infiltration and cartilage degradation. Although TNF has been shown to play a role in the model, direct T cell involvement is almost non-existent due to the passive nature of the immunization and hence this model is not expected to illustrate the effects of Treg expansion. CAIA was induced in male Tg1278/TNFKO mice by i.p. administration of 8 mg Arthritomab™ (arthritogenic cocktail) on day 0. On day 3, animals received 10 µg LPS i.p. to induce robust arthritic symptoms and subsequently mice were assigned to five body weight and arthritis score-matched groups (n=6-7 mice/group). Mice were treated with vehicle, Infliximab or Composition A at 1.5 mg/kg s.c. on days 3, 6, 9 and 12 post-induction. Arthritis pathology was scored daily (except on days 9, 15 and 16)

until day 17 when the mice were sacrificed and the limbs fixed, decalcified and paraffin-embedded to be processed for arthritis histopathological evaluation. An experimental overview is provided in FIG. 11A. In vivo arthritis was evaluated on the front and hind limbs on a scale of 0-4 per mouse limb (maximal score 16) as described below. FIG. 11B shows detailed results of individual animals at day 17.

| ARTHRITIS SCORE[1] | CHARACTERISTICS |
|---|---|
| 0 | Normal |
| 1 | Mild redness, slight swelling of ankle or wrist, including some digits |
| 2 | Moderate swelling of ankle or wrist, including some digits |
| 3 | Severe swelling, including some digits, ankle/wrist and knuckles |
| 4 | Maximally inflamed |

[1]The addition of an extra 0.25 or 0.5 on the scoring of some assessments signifies a tendency towards the next more severe phenotype.

For histopathological analysis, the elbow/carpal of the front limbs and ankle joints of the hind limbs were collected, fixed in 4% aqueous formaldehyde solution overnight at room temperature, demineralized in EDTA decalcification solution (13% EDTA in 0.1M sodium phosphate buffer) at room temperature for 20 days and further placed in PBS at 4° C. until further processing. Samples were paraffin embedded in the transverse plane and paraffin blocks were sectioned using a microtome. After trimming the blocks (to a comparable tissue level), 4 μm-thick sections were cut at 3 different depths, on the surface after trimming, at ~30 μm and at ~70 μm, so in total 3 slides were generated from 3 depths approximating the edge, proximally near the middle and distally close after the middle of the joint. The sections were then haematoxylin/eosin stained and evaluated by light microscopy for histopathological hallmarks of arthritis. The evaluation process was performed in a blinded fashion. Histopathology was assessed according to the histopathology scoring system as described in the following table. In the front limbs, 6 carpal and in the hind limbs at least 6 tarsal bones were evaluated and the final score value arises from the highest score after examination of all 3 slides. Group means are calculated from the individual highest scores per joint in each mouse in the specific group. Results from histopathology scoring at day 17 after sacrifice is shown in FIG. 11C.

CUMULATIVE HISTOPATHOLOGICAL CRITERIA
FOR SCORING ARTHRITIC PHENOTYPE

| SCORE[1] | DISEASE | CRITERIA |
|---|---|---|
| 0 | Normal | no detectable pathology |
| 1 | Mild | hyperplasia of the synovial membrane and presence of polymorphonuclear infiltrates. Mild tendonitis may be present. |
| 2 | Moderate | pannus and fibrous tissue formation and focal subchondral bone erosion |
| 3 | Moderate-Severe | cartilage destruction and bone erosion |
| 4 | Severe | extensive cartilage destruction and bone erosion. Bone outline structure is lost |

[1]Half marks are given when some but not all of the features from the next higher score are present. Hence, a score of "2.5" means pannus and fibrous tissue formation and focal subchondral bone erosion (score 2), with more bone erosion spread outside and around subchondral foci, but not as broad and with cartilage destruction, as to justify a score "3".

Compared to vehicle, Composition A and Infliximab attenuated the arthritic score over the course of the study leading to a significantly reduced histopathology of the joints at the end of the study (FIG. 11C), thus demonstrating the anti-TNF activity of Composition A in vivo.

Example 13: Composition (Suppresses KLH-Induced Delayed Type Hypersensitivity

The ability of Composition C to suppress antigen-driven ear inflammation was tested in a mouse delayed type hypersensitivity (DTH) model. DTH represents a local T effector recall response to a previously encountered antigen. Here, mice are first sensitized to keyhole limpet hemocyanin (KLH) by immunization s.c. with KLH and then rechallenged several days later with an intradermal injection of the same antigen into the ear resulting in local tissue inflammation and swelling.

Figure 12A:
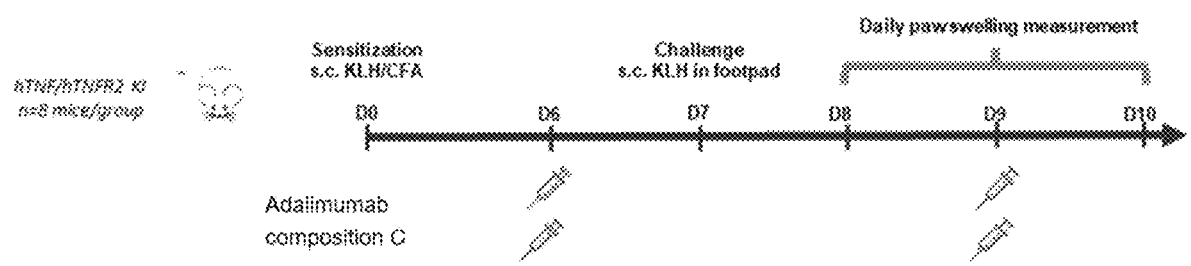
FIG. 12A shows a schematic of an experimental design testing the therapeutic effect of Composition C in a keyhole limpet hemocyanin (KLH)-induced delayed type hypersensitivity mouse model.
Figures 12B, 12C, 12D:
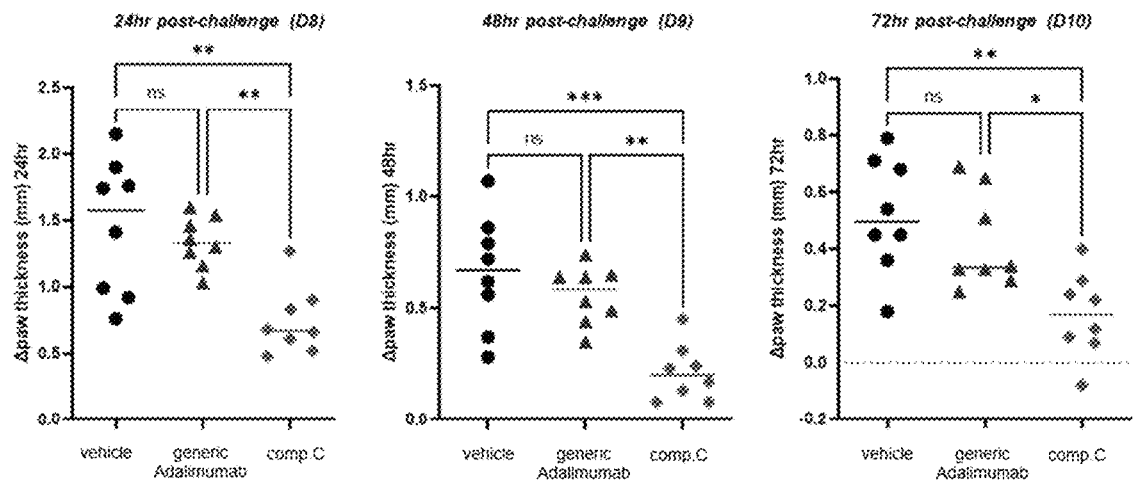
FIG. 12B shows paw thickness difference between the left paw challenged with KLH compared to baseline reported in mm as a measure of swelling at 24 hours post-challenge.
FIG. 12C shows paw thickness difference between the left paw challenged with KLH compared to baseline reported in mm as a measure of swelling at 48 hours post-challenge.
FIG. 12D shows paw thickness difference between the left paw challenged with KLH compared to baseline reported in mm as a measure of swelling at 72 hours post-challenge.

To demonstrate that Composition C can suppress antigen-driven ear inflammation in this model, hTNF/hTNFR2 KI mice (12-13 weeks old) were randomly allocated to experimental groups (n=8/group). On Day 0, animals were administered with an emulsion of 100 μg KLH in CFA by s.c. injection at the two flanks near the base of the tail. Vehicle, Adalimumab or Composition C were administered at 3 mg/kg s.c. on days 6 and 9. Following baseline measurements of paw thickness (right and left paw) on day 7, all animals were challenged with an intra-dermal injection of 20 μg/20 μL KLH in saline in the left footpad, while the right footpad was injected subcutaneously with 20 μL saline to serve as control. Paw thickness measurements of left and right paws were performed 24h (d8), 48h (d9) and 72h (d10) post-challenge. A schematic of the experimental protocol is shown in FIG. 12A. Composition C significantly suppressed paw inflammation at all time points compared to vehicle, whereas Adalimumab had no significant effect (see FIG. 12B, FIG. 12C, and FIG. 12D for change in paw thickness data at 24, 48 and 72 hours post-challenge), thus demonstrating that Composition C was functional in vivo in suppressing DTH.

What is claimed is:

1. A composition comprising:
   an anti-tumor necrosis factor α (TNFα) antibody or antigen binding fragment;
   a modified IL-2 polypeptide comprising amino acid substitutions Y31H, K35R, and Q74P, wherein residue position numbering is based on SEQ ID NO: 1 as a reference sequence; and
   a linker, wherein the linker comprises:
   a first point of attachment covalently attached to the modified IL-2 polypeptide; and
   a second point of attachment covalently attached to the anti-TNFα antibody or antigen binding fragment.

2. The composition of claim 1, wherein the modified IL-2 polypeptide exhibits an affinity for an IL-2 receptor α subunit which is at least about 100-fold greater than an IL-2 receptor β subunit.

3. The composition of claim 1, wherein the modified IL-2 polypeptide further comprises an N88D amino acid substitution.

4. The composition of claim 1, wherein the first point of attachment is at a N-terminal amino acid residue of the modified IL-2 polypeptide.

5. The composition of claim 1, wherein the anti-TNFα antibody or antigen binding fragment is a full-length antibody.

6. The composition of claim 1, wherein the anti-TNFα antibody or antigen binding fragment comprises an Fc region.

7. The composition of claim 6, wherein the second point of attachment is at an amino acid residue in the Fc region.

8. The composition claim 6, wherein the second point of position attachment is at the Fc region at a position of a K246 amino acid residue, a K248 amino acid residue, a K288 amino acid residue, a K317 amino acid residue, or a combination thereof (Eu numbering).

9. The composition of claim 8, wherein the second point of attachment is at the K248 amino acid residue.

10. The composition of claim 1, wherein the anti-TNFα antibody or antigen binding fragment is a monoclonal antibody.

11. The composition of claim 5, wherein the full-length antibody comprises an IgG.

12. The composition of claim 11, wherein the IgG is an IgG1, an IgG4, or is derived therefrom.

13. The composition of claim 1, wherein the anti-TNFα antibody or antigen binding fragment comprises Adalimumab.

14. The composition of claim 1, wherein the anti-TNFα antibody or antigen binding fragment comprises Infliximab.

15. The composition of claim 1, wherein the second point of attachment is to a lysine residue of the anti-TNFα antibody or antigen binding fragment.

16. The composition of claim 1, wherein the linker comprises a polymer.

17. The composition of claim 1, wherein the linker comprises a structure:

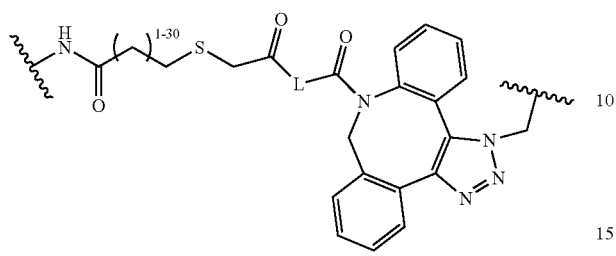

wherein

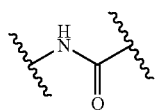

is the first point of attachment to a lysine residue of the anti-TNFα antibody or antigen binding fragment;

L is a linking group; and

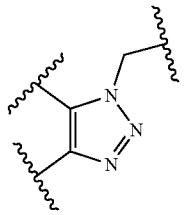 [SMILES: *Cn1nnc(*)c1*]

is a point of attachment to a linking group which connects to the first point of attachment.

18. The composition claim 1, wherein the modified IL-2 polypeptide comprises an amino acid sequence of SEQ ID NO: 3.

* * * * *

SEQUENCE LISTING

```
Sequence total quantity: 148
SEQ ID NO: 1            moltype = AA  length = 133
FEATURE                 Location/Qualifiers
source                  1..133
                        mol_type = protein
                        organism = unidentified
SEQUENCE: 1
```

```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 2            moltype = AA   length = 132
FEATURE                 Location/Qualifiers
source                  1..132
                        mol_type = protein
                        organism = synthetic construct
SEQUENCE: 2
PTSSSTKKTQ LQLEHLLLDL QMILNGINNY KNPKLTRMLT FKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                      132

SEQ ID NO: 3            moltype = AA   length = 133
FEATURE                 Location/Qualifiers
source                  1..133
                        mol_type = protein
                        organism = synthetic construct
SITE                    23
                        note = Norleucine
SITE                    39
                        note = Norleucine
SITE                    41
                        note = Homoserine
SITE                    46
                        note = Norleucine
SITE                    71
                        note = Homoserine
SITE                    104
                        note = Homoserine
SEQUENCE: 3
APTSSSTKKT QLQLEHLLLD LQXILNGINN HKNPRLTRXL XFKFYXPKKA TELKHLQCLE    60
EELKPLEEVL XLAPSKNFHL RPRDLISDIN VIVLELKGSE TTFXCEYADE TATIVEFLNR   120
WITFSQSIIS TLT                                                     133

SEQ ID NO: 4            moltype = AA   length = 133
FEATURE                 Location/Qualifiers
source                  1..133
                        mol_type = protein
                        organism = synthetic construct
SITE                    23
                        note = Norleucine
SITE                    39
                        note = Norleucine
SITE                    41
                        note = Homoserine
SITE                    46
                        note = Norleucine
SITE                    71
                        note = Homoserine
SITE                    104
                        note = Homoserine
SEQUENCE: 4
APTSSSTKKT QLQLEHLLLD LQXILNGINN HKNPRLTRXL XFKFYXPKKA TELKHLQCLE    60
EELKPLEEVL XLAPSKNFHL RPRDLISNIN VIVLELKGSE TTFXCEYADE TATIVEFLNR   120
WITFSQSIIS TLT                                                     133

SEQ ID NO: 5            moltype = AA   length = 133
FEATURE                 Location/Qualifiers
source                  1..133
                        mol_type = protein
                        organism = synthetic construct
SITE                    23
                        note = Norleucine
SITE                    39
                        note = Norleucine
SITE                    41
                        note = Homoserine
SITE                    46
                        note = Norleucine
SITE                    71
                        note = Homoserine
SITE                    104
                        note = Homoserine
SEQUENCE: 5
APTSSSTKKT QLQLEHLLLD LQXILNGINN HKNPRLTRXL XFKFYXPKKA TELKHLQCLE    60
EELKPLEEAL XLAPSKNFHL RPRDLISDIN VIVLELKGSE TTFXCEYADE TATIVEFLNR   120
WITFSQSIIS TLT                                                     133
```

```
SEQ ID NO: 6              moltype = AA   length = 133
FEATURE                   Location/Qualifiers
source                    1..133
                          mol_type = protein
                          organism = synthetic construct
SITE                      23
                          note = Norleucine
SITE                      41
                          note = Homoserine
SITE                      46
                          note = Norleucine
SITE                      71
                          note = Homoserine
SITE                      104
                          note = Homoserine
SEQUENCE: 6
APTSSSTKKT QLQLEHLLLD LQXILNGINN HKNPRLTRAL XFKFYXPKKA TELKHLQCLE   60
EELKPLEEVL XLAPSKNFHL RPRDLISNIN VIVLELKGSE TTFXCEYADE TATIVEFLNR  120
WITFSQSIIS TLT                                                    133

SEQ ID NO: 7              moltype = AA   length = 133
FEATURE                   Location/Qualifiers
source                    1..133
                          mol_type = protein
                          organism = synthetic construct
SITE                      39
                          note = Norleucine
SITE                      41
                          note = Homoserine
SITE                      46
                          note = Norleucine
SITE                      71
                          note = Homoserine
SITE                      104
                          note = Homoserine
SEQUENCE: 7
APTSSSTKKT QLQLEHLLLD LQAILNGINN HKNPRLTRXL XFKFYXPKKA TELKHLQCLE   60
EELKPLEEVL XLAPSKNFHL RPRDLISDIN VIVLELKGSE TTFXCEYADE TATIVEFLNR  120
WITFSQSIIS TLT                                                    133

SEQ ID NO: 8              moltype = AA   length = 133
FEATURE                   Location/Qualifiers
source                    1..133
                          mol_type = protein
                          organism = synthetic construct
SITE                      23
                          note = Norleucine
SITE                      39
                          note = Norleucine
SITE                      41
                          note = Homoserine
SITE                      71
                          note = Homoserine
SITE                      104
                          note = Homoserine
SEQUENCE: 8
APTSSSTKKT QLQLEHLLLD LQXILNGINN HKNPRLTRXL XFKFYAPKKA TELKHLQCLE   60
EELKPLEEVL XLAPSKNFHL RPRDLISNIN VIVLELKGSE TTFXCEYADE TATIVEFLNR  120
WITFSQSIIS TLT                                                    133

SEQ ID NO: 9              moltype = AA   length = 133
FEATURE                   Location/Qualifiers
source                    1..133
                          mol_type = protein
                          organism = synthetic construct
SITE                      23
                          note = Norleucine
SITE                      39
                          note = Norleucine
SITE                      41
                          note = Homoserine
SITE                      46
                          note = Norleucine
SITE                      71
                          note = Homoserine
SITE                      104
                          note = Homoserine
SEQUENCE: 9
```

```
APTSSSTKKT QLQLEHLLLD LQXILNGINN YKNPRLTRXL XFKFYXPKKA TELKHLQCLE   60
EELKPLEEAL XLAPSKNFHL RPRDLISDIN VIVLELKGSE TTFXCEYADE TATIVEFLNR  120
WITFSQSIIS TLT                                                    133

SEQ ID NO: 10              moltype = AA   length = 133
FEATURE                    Location/Qualifiers
source                     1..133
                           mol_type = protein
                           organism = synthetic construct
SITE                       23
                           note = Norleucine
SITE                       39
                           note = Norleucine
SITE                       41
                           note = Homoserine
SITE                       42
                           note = (4-amide)-phenylalanine
SITE                       46
                           note = Norleucine
SITE                       71
                           note = Homoserine
SITE                       104
                           note = Homoserine
SEQUENCE: 10
APTSSSTKKT QLQLEHLLLD LQXILNGINN YKNPKLTRXL XFKFYXPKKA TELKHLQCLE   60
EELKPLEEVL XLAQSKNFHL RPRDLISDIN VIVLELKGSE TTFXCEYADE TATIVEFLNR  120
WITFSQSIIS TLT                                                    133

SEQ ID NO: 11              moltype = AA   length = 133
FEATURE                    Location/Qualifiers
source                     1..133
                           mol_type = protein
                           organism = synthetic construct
SITE                       23
                           note = Norleucine
SITE                       39
                           note = Norleucine
SITE                       41
                           note = Homoserine
SITE                       46
                           note = Norleucine
SITE                       71
                           note = Homoserine
SITE                       104
                           note = Homoserine
SEQUENCE: 11
APTSSSTKKT QLQLEHLLLD LQXILNGINN YKNPKLTRXL XFKFYXPKKA TELKHLQCLE   60
EELKPLEEVL XLAQSKNFHL RPRDLISDIN VIVLELKGSE TTFXCEYADE TATIVEFLNR  120
WITFSQSIIS TLT                                                    133

SEQ ID NO: 12              moltype = AA   length = 133
FEATURE                    Location/Qualifiers
source                     1..133
                           mol_type = protein
                           organism = synthetic construct
SITE                       23
                           note = Norleucine
SITE                       39
                           note = Norleucine
SITE                       41
                           note = Homoserine
SITE                       46
                           note = Norleucine
SITE                       71
                           note = Homoserine
SITE                       88
                           note = O-(2-aminoethyl)-O'-(2-aminoethyl)octaethylene
                             glycol aspartic acid
SITE                       104
                           note = Homoserine
SEQUENCE: 12
APTSSSTKKT QLQLEHLLLD LQXILNGINN YKNPKLTRXL XFKFYXPKKA TELKHLQCLE   60
EELKPLEEVL XLAQSKNFHL RPRDLISDIN VIVLELKGSE TTFXCEYADE TATIVEFLNR  120
WITFSQSIIS TLT                                                    133

SEQ ID NO: 13              moltype = AA   length = 133
FEATURE                    Location/Qualifiers
source                     1..133
                           mol_type = protein
```

```
                        organism = synthetic construct
SEQUENCE: 13
APTSSSTKKT QLQLEHLLLD LQMILNGINN HKNPRLTRML TFKFYMPKKA TELKHLQCLE    60
EELKPLEEAL RLAPSKNFHL RPRDLISNIN VIVLELKGSE TTFMCEYADE TATIVEFLNR   120
WITFSQSIIS TLT                                                     133

SEQ ID NO: 14           moltype = AA   length = 133
FEATURE                 Location/Qualifiers
source                  1..133
                        mol_type = protein
                        organism = synthetic construct
SEQUENCE: 14
APTSSSTKKT QLQLEHLLLD LQMILNGISN HKNPRLARML TFKFYMPEKA TELKHLQCLE    60
EELKPLEEAL RLAPSKNFHL RPRDLISDVN VIVLELKGSE TTFMCEYADE TATIVEFLNR   120
WITFSTSIIS TLT                                                     133

SEQ ID NO: 15           moltype = AA   length = 133
FEATURE                 Location/Qualifiers
source                  1..133
                        mol_type = protein
                        organism = synthetic construct
SEQUENCE: 15
APTSSSTKKT QLQLEHLRLD LEMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSTSIIS TLT                                                     133

SEQ ID NO: 16           moltype = AA   length = 133
FEATURE                 Location/Qualifiers
source                  1..133
                        mol_type = protein
                        organism = synthetic construct
SEQUENCE: 16
APTSSSTKKT QLQLEHLRLD LEMILNGINN YKNPKLTRML TFKFYMPKKA TELKHLQCLE    60
EELKPLEEVL NLAQSKNFHF DPRDVVSDIN VFVLELKGSE TTFMCEYADE TATIVEFLNR   120
WITFSTSIIS TLT                                                     133

SEQ ID NO: 17           moltype = AA   length = 133
FEATURE                 Location/Qualifiers
source                  1..133
                        mol_type = protein
                        organism = synthetic construct
SEQUENCE: 17
APTSSSTKKT QLQLEHLLLD LQMILNGINN HKNPRLTRML TFKFYMPKKA TELKHLQCLE    60
EELKPLEEAL RLAPSKNFHL RPRDLISDIN VIVLELKGSE TTFMCEYADE TATIVEFLNR   120
WITFSQSIIS TLT                                                     133

SEQ ID NO: 18           moltype = AA   length = 133
FEATURE                 Location/Qualifiers
source                  1..133
                        mol_type = protein
                        organism = synthetic construct
SEQUENCE: 18
APTSSSTKKT QLQLEHLLLD LQMILNGINN HKNPRLTRML TFKFYMPKKA TELKHLQCLE    60
EELKPLEEVL NLAPSKNFHL RPRDLISNIN VIVLELKGSE TTFMCEYADE TATIVEFLNR   120
WITFSQSIIS TLT                                                     133

SEQ ID NO: 19           moltype = AA   length = 133
FEATURE                 Location/Qualifiers
source                  1..133
                        mol_type = protein
                        organism = synthetic construct
SEQUENCE: 19
APTSSSTKKT QLQLEHLLLD LQMILNGINN HKNPRLTRML TFKFYMPKKA TELKHLQCLE    60
EELKPLEEVL RLAPSKNFHL RPRDLISNIN VIVLELKGSE TTFMCEYADE TATIVEFLNR   120
WITFSQSIIS TLT                                                     133

SEQ ID NO: 20           moltype = AA   length = 133
FEATURE                 Location/Qualifiers
source                  1..133
                        mol_type = protein
                        organism = synthetic construct
SEQUENCE: 20
APTSSSTKKT QLQLEHLRLD LEMILNGINN YKNPKLTRML TFKFYMPKKA TELKHLQCLE    60
EELKPLEEVL NLAQSKNFHF DPRDVVSNIN VFVLELKGSE TTFMCEYADE TATIVEFLNR   120
WITFSQSIIS TLT                                                     133

SEQ ID NO: 21           moltype = AA   length = 133
FEATURE                 Location/Qualifiers
source                  1..133
```

```
                        mol_type = protein
                        organism = synthetic construct
SEQUENCE: 21
APTSSSTKKT QLQLEHLRLD LQMILNGINN YKNPKLTRML TFKFYMPKKA TELKHLQCLE    60
EELKPLEEVL NLAQSKNFHF DPRDVVSNIN VFVLELKGSE TTFMCEYADE TATIVEFLNR   120
WITFSTSIIS TLT                                                     133

SEQ ID NO: 22           moltype = AA length = 133
FEATURE                 Location/Qualifiers
source                  1..133
                        mol_type = protein
                        organism = synthetic construct
SEQUENCE: 22
APTSSSTKKT QLQLEHLLLD LQMILNGINN YKNPKLTRML TFKFYMPKKA TELKHLQCLE    60
EELKPLEEVL NLAQSKNFHF DPRDVVSNIN VFVLELKGSE TTFMCEYADE TATIVEFLNR   120
WITFSQSIIS TLT                                                     133

SEQ ID NO: 23           moltype = AA length = 133
FEATURE                 Location/Qualifiers
source                  1..133
                        mol_type = protein
                        organism = synthetic construct
SEQUENCE: 23
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSTSIIS TLT                                                     133

SEQ ID NO: 24           moltype = AA length = 133
FEATURE                 Location/Qualifiers
source                  1..133
                        mol_type = protein
                        organism = synthetic construct
SEQUENCE: 24
APTSSSTKKT QLQLEHLLLD LQMILNGINN HKNPKLTRML TFKFYMPKKA TELKHLQCLE    60
EELKPLEEAL RLAPSKNFHL RPRDLISNIN VIVLELKGSE TTFMCEYADE TATIVEFLNR   120
WITFSQSIIS TLT                                                     133

SEQ ID NO: 25           moltype = AA length = 133
FEATURE                 Location/Qualifiers
source                  1..133
                        mol_type = protein
                        organism = synthetic construct
SEQUENCE: 25
APTSSSTKKT QLQLEHLLLD LQMILNGINN HKNPKLTRML TFKFYMPKKA TELKHLQCLE    60
EELKPLEEAL NLAPSKNFHL RPRDLISNIN VIVLELKGSE TTFMCEYADE TATIVEFLNR   120
WITFSQSIIS TLT                                                     133

SEQ ID NO: 26           moltype = AA length = 133
FEATURE                 Location/Qualifiers
source                  1..133
                        mol_type = protein
                        organism = synthetic construct
SEQUENCE: 26
APTSSSTKKT QLQLEHLLLD LQMILNGINN YKNPKLTRML TFKFYMPKKA TELKHLQCLE    60
EELKPLEEVL NLAQSKNFHL RPRDLISDIN VIVLELKGSE TTFMCEYADE TATIVEFLNR   120
WITFSQSIIS TLT                                                     133

SEQ ID NO: 27           moltype = AA length = 133
FEATURE                 Location/Qualifiers
source                  1..133
                        mol_type = protein
                        organism = synthetic construct
SEQUENCE: 27
APTSSSTKKT QLQLEHLLLD LQMILNGINN HKNPKLTRML TFKFYMPKKA TELKHLQCLE    60
EELKPLEEVL RLAQSKNFHL RPRDLISDIN VIVLELKGSE TTFMCEYADE TATIVEFLNR   120
WITFSQSIIS TLT                                                     133

SEQ ID NO: 28           moltype = AA length = 133
FEATURE                 Location/Qualifiers
source                  1..133
                        mol_type = protein
                        organism = synthetic construct
SEQUENCE: 28
APTSSSTKKT QLQLEHLLLD LQMILNGINN HKNPKLTRML TFKFYMPKKA TELKHLQCLE    60
EELKPLEEVL RLAQSKNFHL RPRDLISDIN VIVLELKGSE TTFMCEYADE TATIVEFLNR   120
WITFSTSIIS TLT                                                     133

SEQ ID NO: 29           moltype = AA length = 133
FEATURE                 Location/Qualifiers
```

```
source                  1..133
                        mol_type = protein
                        organism = synthetic construct
SEQUENCE: 29
APTSSSTKKT QLQLEHLLLD LQMILNGINN HKNPRLTRML TFKFYMPKKA TELKHLQCLE    60
EELKPLEEAL RLAPSKNFHL RPRDLISNIN VIVLELKGSE TTFMCEYADE TATIVEFLNR   120
WITFSTSIIS TLT                                                     133

SEQ ID NO: 30           moltype = AA  length = 133
FEATURE                 Location/Qualifiers
source                  1..133
                        mol_type = protein
                        organism = synthetic construct
SEQUENCE: 30
APTSSSTKKT QLQLEHLLLD LQMILNGINN HKNPRLTRML TFKFYMPKKA TELKHLQCLE    60
EELKPLEEVL RLAPSKNFHL RPRDLISDIN VIVLELKGSE TTFMCEYADE TATIVEFLNR   120
WITFSQSIIS TLT                                                     133

SEQ ID NO: 31           moltype = AA  length = 133
FEATURE                 Location/Qualifiers
source                  1..133
                        mol_type = protein
                        organism = synthetic construct
SEQUENCE: 31
APTSSSTKKT QLQLEHLLLD LQMILNGINN HKNPRLTRML TFKFYMPKKA TELKHLQCLE    60
EELKPLEEVL RLAPSKNFHL RPRDLISNIN VIVLELKGSE TTFMCEYADE TATIVEFLNR   120
WITFSTSIIS TLT                                                     133

SEQ ID NO: 32           moltype = AA  length = 133
FEATURE                 Location/Qualifiers
source                  1..133
                        mol_type = protein
                        organism = synthetic construct
SEQUENCE: 32
APTSSSTKKT QLQLEHLLLD LQMILNGINN HKNPRLTRML TFKFYMPKKA TELKHLQCLE    60
EELKPLEEVL NLAPSKNFHL RPRDLISDIN VIVLELKGSE TTFMCEYADE TATIVEFLNR   120
WITFSQSIIS TLT                                                     133

SEQ ID NO: 33           moltype = AA  length = 133
FEATURE                 Location/Qualifiers
source                  1..133
                        mol_type = protein
                        organism = synthetic construct
SEQUENCE: 33
APTSSSTKKT QLQLEHLLLD LQMILNGINN HKNPRLTRML TFKFYMPKKA TELKHLQCLE    60
EELKPLEEVL NLAPSKNFHL RPRDLISNIN VIVLELKGSE TTFMCEYADE TATIVEFLNR   120
WITFSTSIIS TLT                                                     133

SEQ ID NO: 34           moltype = AA  length = 133
FEATURE                 Location/Qualifiers
source                  1..133
                        mol_type = protein
                        organism = synthetic construct
SEQUENCE: 34
APTSSSTKKT QLQLEHLLLD LQMILNGINN HKNPKLTRML TFKFYMPKKA TELKHLQCLE    60
EELKPLEEAL NLAPSKNFHL RPRDLISDIN VIVLELKGSE TTFMCEYADE TATIVEFLNR   120
WITFSQSIIS TLT                                                     133

SEQ ID NO: 35           moltype = AA  length = 133
FEATURE                 Location/Qualifiers
source                  1..133
                        mol_type = protein
                        organism = synthetic construct
SEQUENCE: 35
APTSSSTKKT QLQLEHLLLD LQMILNGINN YKNPKLTRML TFKFYMPKKA TELKHLQCLE    60
EELKPLEEAL NLAPSKNFHL RPRDLISDIN VIVLELKGSE TTFMCEYADE TATIVEFLNR   120
WITFSQSIIS TLT                                                     133

SEQ ID NO: 36           moltype = AA  length = 133
FEATURE                 Location/Qualifiers
source                  1..133
                        mol_type = protein
                        organism = synthetic construct
SEQUENCE: 36
APTSSSTKKT QLQLEHLLLD LQMILNGINN YKNPKLTRML TFKFYMPKKA TELKHLQCLE    60
EELKPLEEAL NLAQSKNFHL RPRDLISDIN VIVLELKGSE TTFMCEYADE TATIVEFLNR   120
WITFSQSIIS TLT                                                     133

SEQ ID NO: 37           moltype = AA  length = 133
```

```
FEATURE                 Location/Qualifiers
source                  1..133
                        mol_type = protein
                        organism = synthetic construct
SEQUENCE: 37
APTSSSTKKT QLQLEHLLLD LQMILNGINN YKNPKLTRML TFKFYMPKKA TELKHLQCLE    60
EELKPLEEVL NLAPSKNFHL RPRDLISDIN VIVLELKGSE TTFMCEYADE TATIVEFLNR   120
WITFSQSIIS TLT                                                      133

SEQ ID NO: 38           moltype = AA  length = 133
FEATURE                 Location/Qualifiers
source                  1..133
                        mol_type = protein
                        organism = synthetic construct
SEQUENCE: 38
APTSSSTKKT QLQLEHLLLD LQMILNGINN HKNPKLTRML TFKFYMPKKA TELKHLQCLE    60
EELKPLEEVL NLAQSKNFHL RPRDLISDIN VIVLELKGSE TTFMCEYADE TATIVEFLNR   120
WITFSQSIIS TLT                                                      133

SEQ ID NO: 39           moltype = AA  length = 133
FEATURE                 Location/Qualifiers
source                  1..133
                        mol_type = protein
                        organism = synthetic construct
SEQUENCE: 39
APTSSSTKKT QLQLEHLLLD LQMILNGINN HKNPKLTRML TFKFYMPKKA TELKHLQCLE    60
EELKPLEEVL NLAPSKNFHL RPRDLISDIN VIVLELKGSE TTFMCEYADE TATIVEFLNR   120
WITFSQSIIS TLT                                                      133

SEQ ID NO: 40           moltype = AA  length = 133
FEATURE                 Location/Qualifiers
source                  1..133
                        mol_type = protein
                        organism = synthetic construct
SEQUENCE: 40
APTSSSTKKT QLQLEHLLLD LQMILNGINN HKNPKLTRML TFKFYMPKKA TELKHLQCLE    60
EELKPLEEAL NLAQSKNFHL RPRDLISDIN VIVLELKGSE TTFMCEYADE TATIVEFLNR   120
WITFSQSIIS TLT                                                      133

SEQ ID NO: 41           moltype = AA  length = 133
FEATURE                 Location/Qualifiers
source                  1..133
                        mol_type = protein
                        organism = synthetic construct
SEQUENCE: 41
APTSSSTKKT QLQLEHLLLD LQMILNGINN HKNPKLTRML TFKFYMPKKA TELKHLQCLE    60
EELKPLEEAL RLAPSKNFHL RPRDLISDIN VIVLELKGSE TTFMCEYADE TATIVEFLNR   120
WITFSQSIIS TLT                                                      133

SEQ ID NO: 42           moltype = AA  length = 133
FEATURE                 Location/Qualifiers
source                  1..133
                        mol_type = protein
                        organism = synthetic construct
SEQUENCE: 42
APTSSSTKKT QLQLEHLLLD LQMILNGINN YKNPKLTRML TFKFYMPKKA TELKHLQCLE    60
EELKPLEEAL RLAPSKNFHL RPRDLISDIN VIVLELKGSE TTFMCEYADE TATIVEFLNR   120
WITFSQSIIS TLT                                                      133

SEQ ID NO: 43           moltype = AA  length = 133
FEATURE                 Location/Qualifiers
source                  1..133
                        mol_type = protein
                        organism = synthetic construct
SEQUENCE: 43
APTSSSTKKT QLQLEHLLLD LQMILNGINN YKNPKLTRML TFKFYMPKKA TELKHLQCLE    60
EELKPLEEVL RLAQSKNFHL RPRDLISDIN VIVLELKGSE TTFMCEYADE TATIVEFLNR   120
WITFSQSIIS TLT                                                      133

SEQ ID NO: 44           moltype =     length =
SEQUENCE: 44
000

SEQ ID NO: 45           moltype =     length =
SEQUENCE: 45
000

SEQ ID NO: 46           moltype =     length =
SEQUENCE: 46
```

```
000

SEQ ID NO: 47            moltype =    length =
SEQUENCE: 47
000

SEQ ID NO: 48            moltype = AA  length = 233
FEATURE                  Location/Qualifiers
source                   1..233
                         mol_type = protein
                         organism = Homo sapiens
SEQUENCE: 48
MSTESMIRDV ELAEEALPKK TGGPQGSRRC LFLSLFSFLI VAGATTLFCL LHFGVIGPQR   60
EEFPRDLSLI SPLAQAVRSS SRTPSDKPVA HVVANPQAEG QLQWLNRRAN ALLANGVELR  120
DNQLVVPSEG LYLIYSQVLF KGQGCPSTHV LLTHTISRIA VSYQTKVNLL SAIKSPCQRE  180
TPEGAEAKPW YEPIYLGGVF QLEKGDRLSA EINRPDYLDF AESGQVYFGI IAL         233

SEQ ID NO: 49            moltype = AA  length = 157
FEATURE                  Location/Qualifiers
source                   1..157
                         mol_type = protein
                         organism = synthetic construct
SEQUENCE: 49
VRSSSRTPSD KPVAHVVANP QAEGQLQWLN RRANALLANG VELRDNQLVV PSEGLYLIYS   60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIAL                           157

SEQ ID NO: 50            moltype =    length =
SEQUENCE: 50
000

SEQ ID NO: 51            moltype =    length =
SEQUENCE: 51
000

SEQ ID NO: 52            moltype =    length =
SEQUENCE: 52
000

SEQ ID NO: 53            moltype =    length =
SEQUENCE: 53
000

SEQ ID NO: 54            moltype =    length =
SEQUENCE: 54
000

SEQ ID NO: 55            moltype =    length =
SEQUENCE: 55
000

SEQ ID NO: 56            moltype =    length =
SEQUENCE: 56
000

SEQ ID NO: 57            moltype =    length =
SEQUENCE: 57
000

SEQ ID NO: 58            moltype =    length =
SEQUENCE: 58
000

SEQ ID NO: 59            moltype =    length =
SEQUENCE: 59
000

SEQ ID NO: 60            moltype =    length =
SEQUENCE: 60
000

SEQ ID NO: 61            moltype =    length =
SEQUENCE: 61
000

SEQ ID NO: 62            moltype =    length =
SEQUENCE: 62
000
```

| | | |
|---|---|---|
| SEQ ID NO: 63
SEQUENCE: 63
000 | moltype = | length = |
| SEQ ID NO: 64
SEQUENCE: 64
000 | moltype = | length = |
| SEQ ID NO: 65
SEQUENCE: 65
000 | moltype = | length = |
| SEQ ID NO: 66
SEQUENCE: 66
000 | moltype = | length = |
| SEQ ID NO: 67
SEQUENCE: 67
000 | moltype = | length = |
| SEQ ID NO: 68
SEQUENCE: 68
000 | moltype = | length = |
| SEQ ID NO: 69
SEQUENCE: 69
000 | moltype = | length = |
| SEQ ID NO: 70
SEQUENCE: 70
000 | moltype = | length = |
| SEQ ID NO: 71
SEQUENCE: 71
000 | moltype = | length = |
| SEQ ID NO: 72
SEQUENCE: 72
000 | moltype = | length = |
| SEQ ID NO: 73
SEQUENCE: 73
000 | moltype = | length = |
| SEQ ID NO: 74
SEQUENCE: 74
000 | moltype = | length = |
| SEQ ID NO: 75
SEQUENCE: 75
000 | moltype = | length = |
| SEQ ID NO: 76
SEQUENCE: 76
000 | moltype = | length = |
| SEQ ID NO: 77
SEQUENCE: 77
000 | moltype = | length = |
| SEQ ID NO: 78
SEQUENCE: 78
000 | moltype = | length = |
| SEQ ID NO: 79
SEQUENCE: 79
000 | moltype = | length = |
| SEQ ID NO: 80
SEQUENCE: 80
000 | moltype = | length = |
| SEQ ID NO: 81
SEQUENCE: 81
000 | moltype = | length = |
| SEQ ID NO: 82
SEQUENCE: 82
000 | moltype = | length = |

| | | |
|---|---|---|
| SEQ ID NO: 83<br>SEQUENCE: 83<br>000 | moltype = | length = |
| SEQ ID NO: 84<br>SEQUENCE: 84<br>000 | moltype = | length = |
| SEQ ID NO: 85<br>SEQUENCE: 85<br>000 | moltype = | length = |
| SEQ ID NO: 86<br>SEQUENCE: 86<br>000 | moltype = | length = |
| SEQ ID NO: 87<br>SEQUENCE: 87<br>000 | moltype = | length = |
| SEQ ID NO: 88<br>SEQUENCE: 88<br>000 | moltype = | length = |
| SEQ ID NO: 89<br>SEQUENCE: 89<br>000 | moltype = | length = |
| SEQ ID NO: 90<br>SEQUENCE: 90<br>000 | moltype = | length = |
| SEQ ID NO: 91<br>SEQUENCE: 91<br>000 | moltype = | length = |
| SEQ ID NO: 92<br>SEQUENCE: 92<br>000 | moltype = | length = |
| SEQ ID NO: 93<br>SEQUENCE: 93<br>000 | moltype = | length = |
| SEQ ID NO: 94<br>SEQUENCE: 94<br>000 | moltype = | length = |
| SEQ ID NO: 95<br>SEQUENCE: 95<br>000 | moltype = | length = |
| SEQ ID NO: 96<br>SEQUENCE: 96<br>000 | moltype = | length = |
| SEQ ID NO: 97<br>SEQUENCE: 97<br>000 | moltype = | length = |
| SEQ ID NO: 98<br>SEQUENCE: 98<br>000 | moltype = | length = |
| SEQ ID NO: 99<br>SEQUENCE: 99<br>000 | moltype = | length = |
| SEQ ID NO: 100<br>FEATURE<br>source<br><br>VARIANT<br><br>SEQUENCE: 100<br>LLQGPX | moltype = AA  length = 6<br>Location/Qualifiers<br>1..6<br>mol_type = protein<br>organism = synthetic construct<br>6<br>note = Alanine or Proline<br><br>6 | |

```
SEQ ID NO: 101          moltype = AA  length = 8
FEATURE                 Location/Qualifiers
source                  1..8
                        mol_type = protein
                        organism = synthetic construct
SEQUENCE: 101
GGLLQGPP                                                                 8

SEQ ID NO: 102          moltype =     length =
SEQUENCE: 102
000

SEQ ID NO: 103          moltype =     length =
SEQUENCE: 103
000

SEQ ID NO: 104          moltype =     length =
SEQUENCE: 104
000

SEQ ID NO: 105          moltype =     length =
SEQUENCE: 105
000

SEQ ID NO: 106          moltype =     length =
SEQUENCE: 106
000

SEQ ID NO: 107          moltype =     length =
SEQUENCE: 107
000

SEQ ID NO: 108          moltype =     length =
SEQUENCE: 108
000

SEQ ID NO: 109          moltype =     length =
SEQUENCE: 109
000

SEQ ID NO: 110          moltype =     length =
SEQUENCE: 110
000

SEQ ID NO: 111          moltype =     length =
SEQUENCE: 111
000

SEQ ID NO: 112          moltype =     length =
SEQUENCE: 112
000

SEQ ID NO: 113          moltype =     length =
SEQUENCE: 113
000

SEQ ID NO: 114          moltype =     length =
SEQUENCE: 114
000

SEQ ID NO: 115          moltype =     length =
SEQUENCE: 115
000

SEQ ID NO: 116          moltype =     length =
SEQUENCE: 116
000

SEQ ID NO: 117          moltype =     length =
SEQUENCE: 117
000

SEQ ID NO: 118          moltype =     length =
SEQUENCE: 118
000

SEQ ID NO: 119          moltype =     length =
SEQUENCE: 119
000
```

```
SEQ ID NO: 120          moltype =   length =
SEQUENCE: 120
000

SEQ ID NO: 121          moltype =   length =
SEQUENCE: 121
000

SEQ ID NO: 122          moltype =   length =
SEQUENCE: 122
000

SEQ ID NO: 123          moltype =   length =
SEQUENCE: 123
000

SEQ ID NO: 124          moltype = AA   length = 20
FEATURE                 Location/Qualifiers
source                  1..20
                        mol_type = protein
                        organism = synthetic construct
VARIANT                 1..20
                        note = This sequence may encompass 1-10 GS repeating units
SEQUENCE: 124
GSGSGSGSGS GSGSGSGSGS                                                      20

SEQ ID NO: 125          moltype = AA   length = 30
FEATURE                 Location/Qualifiers
source                  1..30
                        mol_type = protein
                        organism = synthetic construct
VARIANT                 1..30
                        note = This sequence may encompass 1-10 GGS repeating units
SEQUENCE: 125
GGSGGSGGSG GGGSGGSGG SGGSGGSGGS                                            30

SEQ ID NO: 126          moltype = AA   length = 40
FEATURE                 Location/Qualifiers
source                  1..40
                        mol_type = protein
                        organism = synthetic construct
VARIANT                 1..40
                        note = This sequence may encompass 1-10 GGGS repeating units
SEQUENCE: 126
GGGSGGGSGG GSGGGSGGGS GGGSGGGSGG GSGGGSGGGS                                40

SEQ ID NO: 127          moltype = AA   length = 40
FEATURE                 Location/Qualifiers
source                  1..40
                        mol_type = protein
                        organism = synthetic construct
VARIANT                 1..40
                        note = This sequence may encompass 1-10 GGSG repeating units
SEQUENCE: 127
GGSGGGSGGG SGGGSGGGSG GGSGGGSGGG SGGGSGGGSG                                40

SEQ ID NO: 128          moltype = AA   length = 50
FEATURE                 Location/Qualifiers
source                  1..50
                        mol_type = protein
                        organism = synthetic construct
VARIANT                 1..50
                        note = This sequence may encompass 1-10 GGSGG repeating
                         units
SEQUENCE: 128
GGSGGGSGG GGSGGGSGG GGSGGGSGG GGSGGGSGG GGSGGGSGG                          50

SEQ ID NO: 129          moltype = AA   length = 50
FEATURE                 Location/Qualifiers
source                  1..50
                        mol_type = protein
                        organism = synthetic construct
VARIANT                 1..50
                        note = This sequence may encompass 1-10 GGGGS repeating
                         units
SEQUENCE: 129
GGGGSGGGGS GGGGSGGGGS GGGGSGGGGS GGGGSGGGGS GGGGSGGGGS                     50
```

```
SEQ ID NO: 130           moltype = AA   length = 15
FEATURE                  Location/Qualifiers
source                   1..15
                         mol_type = protein
                         organism = synthetic construct
SEQUENCE: 130
GGGGSGGGGS GGGGS                                                          15

SEQ ID NO: 131           moltype = AA   length = 20
FEATURE                  Location/Qualifiers
source                   1..20
                         mol_type = protein
                         organism = synthetic construct
SEQUENCE: 131
GGGGSGGGGS GGGGSGGGGS                                                     20

SEQ ID NO: 132           moltype = AA   length = 451
FEATURE                  Location/Qualifiers
source                   1..451
                         mol_type = protein
                         organism = synthetic construct
SEQUENCE: 132
EVQLVESGGG LVQPGRSLRL SCAASGFTFD DYAMHWVRQA PGKGLEWVSA ITWNSGHIDY          60
ADSVEGRFTI SRDNAKNSLY LQMNSLRAED TAVYYCAKVS YLSTASSLDY WGQGTLVTVS         120
SASTKGPSVF PLAPSSKSTS GGTAALGCLV KDYFPEPVTV SWNSGALTSG VHTFPAVLQS         180
SGLYSLSSVV TVPSSSLGTQ TYICNVNHKP SNTKVDKKVE PKSCDKTHTC PPCPAPELLG         240
GPSVFLFPPK PKDTLMISRT PEVTCVVVDV SHEDPEVKFN WYVDGVEVHN AKTKPREEQY         300
NSTYRVVSVL TVLHQDWLNG KEYKCKVSNK ALPAPIEKTI SKAKGQPREP QVYTLPPSRD         360
ELTKNQVSLT CLVKGFYPSD IAVEWESNGQ PENNYKTTPP VLDSDGSFFL YSKLTVDKSR         420
WQQGNVFSCS VMHEALHNHY TQKSLSLSPG K                                        451

SEQ ID NO: 133           moltype = AA   length = 214
FEATURE                  Location/Qualifiers
source                   1..214
                         mol_type = protein
                         organism = synthetic construct
SEQUENCE: 133
DIQMTQSPSS LSASVGDRVT ITCRASQGIR NYLAWYQQKP GKAPKLLIYA ASTLQSGVPS          60
RFSGSGSGTD FTLTISSLQP EDVATYYCQR YNRAPYTFGQ GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                     214

SEQ ID NO: 134           moltype = AA   length = 226
FEATURE                  Location/Qualifiers
source                   1..226
                         mol_type = protein
                         organism = synthetic construct
SEQUENCE: 134
EVKLEESGGG LVQPGGSMKL SCVASGFIFS NHWMNWVRQS PEKGLEWVAE IRSKSINSAT          60
HYAESVKGRF TISRDDSKSA VYLQMTDLRT EDTGVYYCSR NYYGSTYDYW GQGTTLTVSS         120
ASTKGPSVFP LAPSSKSTSG GTAALGCLVK DYFPEPVTVS WNSGALTSGV HTFPAVLQSS         180
GLYSLSSVVT VPSSSLGTQT YICNVNHKPS NTKVDKKVEP KSCDKT                        226

SEQ ID NO: 135           moltype = AA   length = 214
FEATURE                  Location/Qualifiers
source                   1..214
                         mol_type = protein
                         organism = synthetic construct
SEQUENCE: 135
DILLTQSPAI LSVSPGERVS FSCRASQFVG SSIHWYQQRT NGSPRLLIKY ASESMSGIPS          60
RFSGSGSGTD FTLSINTVES EDIADYYCQQ SHSWPFTFGS GTNLEVKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                     214

SEQ ID NO: 136           moltype = AA   length = 230
FEATURE                  Location/Qualifiers
source                   1..230
                         mol_type = protein
                         organism = synthetic construct
VARIANT                  18
                         note = Any naturally occurring amino acid
VARIANT                  19
                         note = Any naturally occurring amino acid
VARIANT                  21
                         note = Any naturally occurring amino acid
VARIANT                  140
                         note = Any naturally occurring amino acid
VARIANT                  142
                         note = Any naturally occurring amino acid
```

```
VARIANT                 177
                        note = Any naturally occurring amino acid
SEQUENCE: 136
PKSCDKTHTC PPCPAPEXXG XPSVFLFPPK PKDTLMISRT PEVTCVVVDV SHEDPEVKFN    60
WYVDGVEVHN AKTKPREEQY DSTYRVVSVL TVLHQDWLNG KEYKCKVSNK ALPAPIEKTI   120
SKAKGQPREP QVYTLPPSRX EXTKNQVSLT CLVKGFYPSD IAVEWESNGQ PENNYKXTPP   180
VLDSDGSFFL YSKLTVDKSR WQQGNVFSCS VMHEALHNHY TQKSLSLSPG              230

SEQ ID NO: 137          moltype = AA   length = 48
FEATURE                 Location/Qualifiers
source                  1..48
                        mol_type = protein
                        organism = synthetic construct
SEQUENCE: 137
QETNPTENLY FQQKNMQCQR RFYEALHDPN LNEEQRNARI RSIRDDDC                 48

SEQ ID NO: 138          moltype = AA   length = 61
FEATURE                 Location/Qualifiers
source                  1..61
                        mol_type = protein
                        organism = synthetic construct
SEQUENCE: 138
QTADNQKNMQ CQRRFYEALH DPNLNEEQRN ARIRSIRDDC SQSANLLAEA QQLNDAQAPQ    60
A                                                                   61

SEQ ID NO: 139          moltype = AA   length = 38
FEATURE                 Location/Qualifiers
source                  1..38
                        mol_type = protein
                        organism = synthetic construct
SEQUENCE: 139
QETKNMQCQR RFYEALHDPN LNEEQRNARI RSIRDDDC                            38

SEQ ID NO: 140          moltype = AA   length = 38
FEATURE                 Location/Qualifiers
source                  1..38
                        mol_type = protein
                        organism = synthetic construct
SEQUENCE: 140
QETFNKQCQR RFYEALHDPN LNEEQRNARI RSIRDDDC                            38

SEQ ID NO: 141          moltype = AA   length = 38
FEATURE                 Location/Qualifiers
source                  1..38
                        mol_type = protein
                        organism = synthetic construct
SEQUENCE: 141
QETFNMQCQR RFYEALHDPN LNKEQRNARI RSIRDDDC                            38

SEQ ID NO: 142          moltype = AA   length = 37
FEATURE                 Location/Qualifiers
source                  1..37
                        mol_type = protein
                        organism = synthetic construct
SEQUENCE: 142
QETFNMQCQR RFYEALHDPN LNEEQRNARI RSIKDDC                             37

SEQ ID NO: 143          moltype = AA   length = 35
FEATURE                 Location/Qualifiers
source                  1..35
                        mol_type = protein
                        organism = synthetic construct
SEQUENCE: 143
QETMQCQRRF YEALHDPNLN EEQRNARIRS IKDDC                               35

SEQ ID NO: 144          moltype = AA   length = 34
FEATURE                 Location/Qualifiers
source                  1..34
                        mol_type = protein
                        organism = synthetic construct
```

```
SEQUENCE: 144
QETQCQRRFY EALHDPNLNE EQRNARIRSI KDDC                                    34

SEQ ID NO: 145          moltype = AA  length = 33
FEATURE                 Location/Qualifiers
source                  1..33
                        mol_type = protein
                        organism = synthetic construct
SEQUENCE: 145
QETCQRRFYE ALHDPNLNEE QRNARIRSIK DDC                                     33

SEQ ID NO: 146          moltype = AA  length = 20
FEATURE                 Location/Qualifiers
source                  1..20
                        mol_type = protein
                        organism = synthetic construct
SEQUENCE: 146
QETRGNCAYH KGQLVWCTYH                                                    20

SEQ ID NO: 147          moltype = AA  length = 20
FEATURE                 Location/Qualifiers
source                  1..20
                        mol_type = protein
                        organism = synthetic construct
SEQUENCE: 147
QETRGNCAYH KGQIIWCTYH                                                    20

SEQ ID NO: 148          moltype = AA  length = 17
FEATURE                 Location/Qualifiers
source                  1..17
                        mol_type = protein
                        organism = synthetic construct
SITE                    1
                        note = Acetyl arginine
DISULFID                4..14
                        note = Intrachain disulfide bond
SITE                    8
                        note =
                        Lysine-3-((3-((2,5-dioxopyrrolidin-1-yl)oxy)-3-oxopropyl)di
                        sulfaneyl)propanoate
SITE                    17
                        note = Histidine amide
SEQUENCE: 148
RGNCAYHKGQ LVWCTYH                                                       17
```